(12) United States Patent
Zwaal

(10) Patent No.: US 9,121,014 B2
(45) Date of Patent: Sep. 1, 2015

(54) PLASMINOGEN AND PLASMIN VARIANTS

(75) Inventor: Richard Reinier Zwaal, Heverlee (BE)

(73) Assignee: ThromboGenies NV, Heverlee/Leuven (BE)

( * ) Notice: Subject to any disclaimer, the term of this patent is extended or adjusted under 35 U.S.C. 154(b) by 0 days.

(21) Appl. No.: 13/977,836

(22) PCT Filed: Jan. 4, 2012

(86) PCT No.: PCT/EP2012/050074
§ 371 (c)(1),
(2), (4) Date: Jul. 1, 2013

(87) PCT Pub. No.: WO2012/093132
PCT Pub. Date: Jul. 12, 2012

(65) Prior Publication Data
US 2013/0273028 A1   Oct. 17, 2013

Related U.S. Application Data

(60) Provisional application No. 61/429,868, filed on Jan. 5, 2011.

(30) Foreign Application Priority Data

Jan. 5, 2011   (EP) ..................................... 11150246

(51) Int. Cl.
*A61K 38/48*   (2006.01)
*C12N 9/68*   (2006.01)
*A61K 45/06*   (2006.01)
*C12Q 1/37*   (2006.01)

(52) U.S. Cl.
CPC ............ *C12N 9/6435* (2013.01); *A61K 38/484* (2013.01); *A61K 45/06* (2013.01); *C12Q 1/37* (2013.01); *C12Y 304/21007* (2013.01)

(58) Field of Classification Search
None
See application file for complete search history.

(56) References Cited

U.S. PATENT DOCUMENTS

| | | | |
|---|---|---|---|
| 3,208,908 A | 9/1965 | Maxwell et al. | |
| 4,122,158 A | 10/1978 | Schmitt | |
| 4,462,980 A | 7/1984 | Diedrichsen et al. | |
| 4,774,087 A | 9/1988 | Wu et al. | |
| 5,087,572 A | 2/1992 | Castellino et al. | |
| 5,288,489 A | 2/1994 | Reich et al. | |
| 5,304,118 A | 4/1994 | Trese et al. | |
| 5,304,383 A | 4/1994 | Eibl et al. | |
| 5,407,673 A | 4/1995 | Reich et al. | |
| 5,520,912 A | 5/1996 | Eibl et al. | |
| 5,597,800 A | 1/1997 | Eibl et al. | |
| 5,776,452 A | 7/1998 | Eibl et al. | |
| 5,879,923 A | 3/1999 | Yago et al. | |
| 6,057,122 A | 5/2000 | Davidson | |
| 6,355,243 B1 | 3/2002 | Novokhatny et al. | |
| 6,585,972 B2 | 7/2003 | Peyman | |
| 6,733,750 B1 | 5/2004 | Peyman | |
| 6,787,135 B2 | 9/2004 | Trese et al. | |
| 6,899,877 B2 | 5/2005 | Peyman | |
| 6,946,438 B1 | 9/2005 | Nagai et al. | |
| 6,964,764 B2 | 11/2005 | Zimmerman et al. | |
| 6,969,515 B2 | 11/2005 | Jesmok et al. | |
| 7,445,775 B2 | 11/2008 | Collen et al. | |
| 7,544,500 B2 | 6/2009 | Bradley et al. | |
| 7,547,435 B2 | 6/2009 | Pakola et al. | |
| 7,776,026 B2 | 8/2010 | Trese et al. | |
| 7,803,368 B2 | 9/2010 | Pakola et al. | |
| 7,867,489 B2 | 1/2011 | Pakola et al. | |
| 7,871,608 B2 | 1/2011 | Zimmerman et al. | |
| 7,914,783 B2 | 3/2011 | Pakola et al. | |
| 8,034,913 B2 | 10/2011 | Hunt et al. | |
| 8,101,394 B2 | 1/2012 | Novokhatny | |
| 8,182,808 B2 | 5/2012 | Novokhatny | |
| 8,231,869 B2 | 7/2012 | Scuderi, Jr. et al. | |
| 8,268,782 B2 | 9/2012 | Rebbeor et al. | |
| 8,383,105 B2 | 2/2013 | Pakola et al. | |
| 8,420,079 B2 | 4/2013 | Hunt et al. | |
| 8,460,655 B2 | 6/2013 | Pakola et al. | |
| 8,512,980 B2 | 8/2013 | Novokhatny | |
| 2003/0147877 A1 | 8/2003 | Trese et al. | |
| 2004/0081643 A1 | 4/2004 | Peyman | |
| 2006/0024349 A1 | 2/2006 | Trese et al. | |
| 2007/0212358 A1 | 9/2007 | Bartels | |
| 2007/0231352 A1 | 10/2007 | Tsai | |
| 2011/0300123 A1 | 12/2011 | Pakola et al. | |
| 2012/0114630 A1 | 5/2012 | Zwaal | |
| 2013/0164273 A1 | 6/2013 | Zimmerman et al. | |
| 2013/0164815 A1 | 6/2013 | Dadd et al. | |
| 2013/0195887 A1 | 8/2013 | Pakola et al. | |
| 2013/0202613 A1 | 8/2013 | Pakola et al. | |
| 2013/0302304 A1 | 11/2013 | Pakola et al. | |
| 2014/0205588 A1 | 7/2014 | Zwaal | |

FOREIGN PATENT DOCUMENTS

| | | |
|---|---|---|
| CN | 1560239 | 1/2005 |
| CN | 101209347 | 7/2008 |
| EP | 0 009 879 | 4/1980 |
| EP | 0 480 906 | 4/1992 |
| EP | 0 631 786 | 6/1998 |

(Continued)

OTHER PUBLICATIONS

Dawson (Biochemistry (1994) 33:40 (12042-12047).*
Jespers (Biochemistry (1998) 37(18): 6380-6386).*
Terzyan (Proteins (Aug. 1, 2004) 56(2): 277-284).*
Grella et al., "Activation of human plasminogen by staphylokinase. Direct evidence that preformed plasmin is necessary for activation to occur," *Blood*, 89:1585-1589 (1997).

(Continued)

*Primary Examiner* — Karlheinz R Skowronek
*Assistant Examiner* — Mindy Newman
(74) *Attorney, Agent, or Firm* — Fish & Richardson P.C.

(57) ABSTRACT

The invention relates to variants of plasminogen and plasmin comprising one or more point mutations in the catalytic domain which reduce or prevent autocatylic destruction of the protease activity plasmin. Compositions, uses and methods of using said variants of plasminogen and plasmin are also disclosed.

45 Claims, 14 Drawing Sheets

(56) References Cited

FOREIGN PATENT DOCUMENTS

Figure 3:
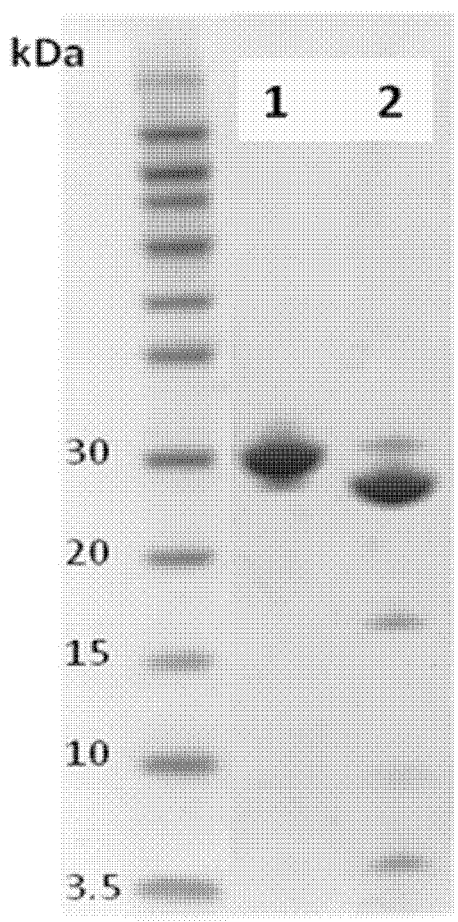

| EP | 1 117 437 | 7/2001 |
|---|---|---|
| EP | 1 232 251 | 8/2002 |
| EP | 1 232 252 | 8/2002 |
| EP | 1 232 254 | 8/2002 |
| EP | 1 343 903 | 9/2003 |
| EP | 1 581 254 | 10/2005 |
| EP | 1 740 698 | 1/2007 |
| EP | 2 327 415 | 6/2011 |
| EP | 2 327 416 | 6/2011 |
| GB | 2 393 121 | 3/2004 |
| WO | WO 89/01336 | 2/1989 |
| WO | WO 90/13640 | 11/1990 |
| WO | WO 91/08297 | 6/1991 |
| WO | WO 93/07893 | 4/1993 |
| WO | WO 93/15189 | 8/1993 |
| WO | WO 97/01631 | 1/1997 |
| WO | WO 00/18436 | 4/2000 |
| WO | WO 01/04269 | 1/2001 |
| WO | WO 01/24817 | 4/2001 |
| WO | WO 01/36608 | 5/2001 |
| WO | WO 01/36609 | 5/2001 |
| WO | WO 01/36611 | 5/2001 |
| WO | WO 01/58921 | 8/2001 |
| WO | WO 02/50290 | 6/2002 |
| WO | WO 02/078564 | 10/2002 |
| WO | WO 03/033019 | 4/2003 |
| WO | WO 03/066842 | 8/2003 |
| WO | WO 2004/045558 | 6/2004 |
| WO | WO 2004/052228 | 6/2004 |
| WO | WO 2005/016455 | 2/2005 |
| WO | WO 2005/078109 | 8/2005 |
| WO | WO 2005/105990 | 11/2005 |
| WO | WO 2006/122249 | 11/2006 |
| WO | WO 2007/047874 | 4/2007 |
| WO | WO 2007/070390 | 6/2007 |
| WO | WO 2007/078761 | 7/2007 |
| WO | WO 2007/101005 | 9/2007 |
| WO | WO 2008/026999 | 3/2008 |
| WO | WO 2008/054592 | 5/2008 |
| WO | WO 2009/073457 | 6/2009 |
| WO | WO 2009/073471 | 6/2009 |
| WO | WO 2011/004011 | 1/2011 |
| WO | WO 2012/093132 | 7/2012 |
| WO | WO 2013/024074 | 2/2013 |

OTHER PUBLICATIONS

International Search Report for App. Ser. No. PCT/EP2012/065832, dated Nov. 19, 2012, 6 pages.
Astrup et al., "The fibrin plate method for estimating fibrinolytic activity," *Arch Biochem. Biophys.*, 346-351 (1952).
Bergmann et al., "Clot-selective coronary thrombolysis with tissue-type plasminogen activator," *Science*, 220:1181-1183 (1983).
Castellino et al., "Rabbit plasminogen and plasmin isozymes," *Methods Enzymol.*, 45:273-286 (1976).
Christensen et al., "Enzymic properties of the neo-plasmin-Val-422 (miniplasmin)," *Biochim. Biophys. Acta*, 567:472-481 (1979).
Christensen et al., "Stopped-flow fluorescence kinetics of bovine alpha 2-antiplasmin inhibition of bovine midiplasmin," *Biochem J.*, 305:97-102 (1995).
Collen et al., "Thrombolysis with human extrinsic (tissue-type) plasminogen activator in rabbits with experimental jugular vein thrombosis. Effect of molecular form and dose of activator, age of the thrombus, and route of administration," *J Clin. Invest.*, 71:368-376 (1983).
Collen et al., Isolation and characterisation of natural and recombinant staphylokinase, *Fibrinolysis*, 6, 203-213 (1992).
Dawson et al., "Substitution of arginine 719 for glutamic acid in human plasminogen substantially reduces its affinity for streptokinase," *Biochemistry*, 33(40):12042-12047 (1994).
Deacon et al., "Technetium 99m-plasmin: a new test for the detection of deep vein thrombosis," *Br. J. Radiol.*, 53:673-677 (1980).

Deutsch et al., "Plasminogen: purification from human plasma by affinity chromatography," *Science*, 170:1095-1096 (1970).
GenBank Accession No. AAA36451, plasminogen [*Homo sapiens*] (Apr. 27, 1993), 3 pages.
Hendrickson et al., "Incorporation of nonnatural amino acids into proteins," *Annu. Rev. Biochem.*, 73:147-176 (2004).
Hotchkiss et al., "A new pan species model for the measurement of in vivo thrombolysis," *Thromb. Haemost.*, 58:107—Abstract 377 (1987).
Hunt et al., "Simplified recombinant plasmin: production and functional comparison of a novel thrombolytic molecule with plasma-derived plasmin," *Throm. Haemost.*, 100(3):413-419 (2008).
Jespers et al., "Arginine 719 in human plasminogen mediates formation of the staphylokinase:plasmin activator complex," *Biochemisty*, 37(18):6380-6386 (1998).
Jespersen et al., "The autodigestion of human plasmin follows a bimolecular mode of reaction subject to product inhibition," 41:395-404 (1986).
Linde et al., "Elimination of the Cys558-Cys566 bond in Lys78-plasminogen—effect on activation and fibrin interaction," *Eur. J Biochem.*, 251:472-479 (1998).
Mhashilkar et al., "Breaching the conformational integrity of the catalytic triad of the serine protease plasmin: localized disruption of a side chain of His-603 strongly inhibits the amidolytic activity of human plasmin," *Proc. Natl. Acad. Sci. USA*, 90:5374-5377 (1993).
Nguyen et al., "Protein composition of plasmin preparation "homolysin"," *Prep. Biochem.*, 11:159-172 (1981).
Ohyama et al., "Nonlysine-analog plasminogen modulators promote autoproteolytic generation of plasmin(ogen) fragments with angiostatin-like activity," *Eur. J. Biochem.*, 271:809-820 (2004).
Papadopoulos et al., "COBALT: constraint-based alignment tool for multiple protein sequences," *Bioinformatics*, 23:1073-79 (2007).
Parry et al., "Molecular mechanisms of plasminogen activation: bacterial cofactors provide clues," *Trends Biochem Sci.*, 25(2):53-59 (2000).
Peisach et al., "Crystal structure of the proenzyme domain of plasminogen," *Biochemistry*, 38:11180-11188 (1999).
Powell et al., "Activation of human neo-plasminogen-Val$_{442}$ by urokinase and streptokinase and a kinetic characterization of neoplasmin-Val$_{442}$," *J Biol. Chem.*, 255:5329-5335 (1980).
Robbins et al., "Human plasminogen and plasmin," *Methods Enzymol.*, 19:184-199 (1970).
Ruyssen et al., Chapter IX—Plasmin, In "Pharmaceutical Enzymes," Story-Scientia, Gent, Belgium, 123-131 (1978).
Salonen et al., "Rapid appearance of plasmin in tear fluid after ocular allergen exposure," *Clin. Exp. Immunol.*, 73(1):146-148 (1988).
Shi et al., "Differential autolysis of human plasmin at various pH levels," *Thromb. Res.*, 51:355-364 (1988).
Takeda-Shitaka et al., "Structural studies of the interactions of normal and abnormal human plasmins with bovine basic pancreatic trypsin inhibitor," *Chem. Pharm. Bull*, 47:322-328 (1999).
Terzyan et al., "Characterization of Lys-698-to-Met substitution in human plasminogen catalytic domain," *Proteins*, 56(2):277-284 (2004).
Ueshima et al., "Stabilization of plasmin by lysine derivatives," *Clin. Chim. Acta*, 245:7-18 (1996).
Verstraete, "Clinical application of inhibitors of fibrinolysis," *Drugs*, 29:236-261 (1985).
Wang et al., "Structure and function of microplasminogen: I. Methionine shuffling, chemical proteolysis, and proenzyme activation," *Protein Sci.*, 4:1758-1767 (1995).
Wang et al., "Structure and function of microplasminogen: II. Determinants of activation by urokinase and by the bacterial activator streptokinase," *Protein Sci.*, 4:1768-1779 (1995).
Wang et al., "Zymogen activation in the streptokinase-plasminogen complex. Ile1 is required for the formation of a functional active site," *Eur. J. Biochem.*, 267:3994-4001 (2000).
Wang et al., "Human plasminogen catalytic domain undergoes an unusual conformational change upon activation," *J. Mol. Biol.*, 295(4):903-914 (2000).
Weinstein et al., "Differential specificities of the thrombin, plasmin and trypsin with regard to synthetic and natural substrates and inhibitors," *Biochim. Biophys. Acta*, 258:577-590 (1972).

(56) References Cited

OTHER PUBLICATIONS

Welsh et al., "Effect of lactacidosis on pyridine nucleotide stability during ischemia in mouse brain," *J. Neurochem.*, 49:846-851 (1987).
International Search Report for App. Ser. No. PCT/EP2010/059902, mailed Aug. 25, 2010, 9 pages.
International Preliminary Report on Patentability for App. Ser. No. PCT/EP2010/059902, dated Jan. 10, 2012, 6 pages.
Wang et al., "Deletion of Ile1 changes the mechanism of streptokinase: evidence for the molecular sexuality hypothesis," *Biochemistry*, 38:5232-5240 (1999).

* cited by examiner

```
1          11         21         31         41         51
|          |          |          |          |          |
EPLDDYVNTQ GASLFSVTKK QLGAGSIEEC AAKCEEDEEF TCRAFQYHSK EQQCVIMAEN
61         71         81         91         101        111
|          |          |          |          |          |
RKSSIIIRMR DVVLFEKKVY ISECKTGNGK NYRGTMSKTK NGITCQKWSS TSPHRPRFSP
121        131        141        151        161        171
|          |          |          |          |          |
ATHPSEGLEE NYCRNPDNDP QGPWCYTTDP EKRYDYCDIL ECEEECMHCS GENYDGKISK
181        191        201        211        221        231
|          |          |          |          |          |
TMSGLECQAW DSQSPHAHGY IPSKFPNKNL KKNYCRNPDR ELRPWCFTTD PNKRWELCDI
241        251        261        271        281        291
|          |          |          |          |          |
PRCTTPPPSS GHTYQCLKGT GENYRGNVAV TVSGHTCQHW SAQTPHTHNR TPENFPCKNL
301        311        321        331        341        351
|          |          |          |          |          |
DENYCRNPDG KRAPWCHTTN SQVRWEYCKI PSCDSSPVST EQLAPTAPPE LTPVVQDCYH
361        371        381        391        401        411
|          |          |          |          |          |
GDGQSYRGTS STTTTGKKCQ SWSSMTPHRH QKTPENYPNA GLTMNYCRNP DADKGPWCFT
421        431        441        451        461        471
|          |          |          |          |          |
TDPSVRWEYC NLKKCSGTEA SVVAPPPVVL LPDVETPSEE DCMFGNGKGY RGKRATTVTG
481        491        501        511        521        531
|          |          |          |          |          |
TPCQDWAAQE PHRHSIFTPE TNPRAGLEKN YCRNPDGDVG GPWCYTTNPR KLYDYCDVPQ
541        551        561        571        581        591
|          |         |1        9|        19|        29|        39
|          |         ||         ||         ||         ||         |
CAAPSFDCGK PQVEPKKCPG RVVGGCVAHP HSWPWQVSLR TRFGMHFCGG TLISPEWVLT
601        611        621        631        641        651
|        49|        59|        69|        79|        89|        99
|          ||         ||         ||         ||         ||        |
AAHCLEKSPR PSSYKVILGA HQEVNLEPHV QEIEVSRLFL EPTRKDIALL KLSSPAVITD
661        671        681        691        701        711
|       109|       119|       129|       139|       149|       159
|          ||         ||         ||         ||         ||        |
KVIPACLPSP NYVVADRTEC FITGWGETQG TFGAGLLKEA QLPVIENKVC NRYEFLNGRV
721        731        741        751        761        771
|       169|       179|       189|       199|       209|       219
|          ||         ||         ||         ||         ||        |
QSTELCAGHL AGGTDSCQGD SGGPLVCFEK DKYILQGVTS WGLGCARPNK PGVYVRVSRF
781        791
|       229|
|          ||
VTWIEGVMRN N (SEQ ID NO:1)
```

FIGURE 1

COBALT (Constraint-based Multiple Alignment Tool) alignment of plasminogen amino acid sequences Line # in sequence alignment
1: Homo sapiens /Genbank AAA36451/ human (SEQ ID NO:1)
2: Canis familiaris /Genbank XP_533468/ dog (SEQ ID NO:2)
3: Pan troglodytes /Genbank XP_001152889/ chimpanzee/ isoform 3 (SEQ ID NO:3)
4: Pan troglodytes /Genbank XP_001152830/ chimpanzee/ isoform 2 (SEQ ID NO:4)
5: Pan troglodytes /Genbank XP_518844/ chimpanzee/ isoform 4 (SEQ ID NO:5)
6: Macaca mulatta /Genbank NP_001036540/ Rhesus monkey (SEQ ID NO:6)
7: Pongo abelii /Genbank NP_001126035/ Sumatran orangutan (SEQ ID NO:7)
8: Sus scrofa /Genbank NP_001038055/ pig (SEQ ID NO:8)
9: Bos Taurus /Genbank DAA25966/ cattle (SEQ ID NO:9)
10: Equus caballus /Genbank XP_001500552/ horse (SEQ ID NO:10)
11: Mus musculus /Genbank EDL02061/ house mouse (SEQ ID NO:11)
12: Rattus norvegicus /Genbank NP_445943/ Norway rat (SEQ ID NO:12)
13: Erinaceus europaeus /Genbank AAC48717/ western European hedgehog (SEQ ID NO:13)
14: Oryctolagus cuniculus /Genbank XP_002715012/ rabbit (SEQ ID NO:14)
15: Pan troglodytes/ Genbank XP_001152435/ chimpanzee/ isoform 1 (SEQ ID NO:15)
16: Ailuropoda melanoleuca/ Genbank EFB19688/panda (SEQ ID NO:16)
17: Papio hamadryas/ Genbank AAB97887/baboon (SEQ ID NO:17)
18: Ovis aries/ Genbank P81286/sheep (SEQ ID NO:18)

FIGURE 2A

```
                           1         11        21        31        41
                           |         |         |         |         |
                       ▶ EPLDDYVNTQGASLFSVTKKQLGAGSIEECAAKCEEDEEFTCR----
 1  1 -----MEHKEVVLLILLFLLFLKSGQG SLLDDYVNTQGASVFSLTKKQLSVGSIEECAAKCEEETGFICR----
 2  1 -----MEHKEVVLLLLLLFLLFLKSGHG EPLDDYVNTQGASLFSVTKKQLGAGSIEECAAKCEEDKEFTCR----
 3  1 -----MEHKEVVLLLLLLFLLLFLKSGQG EPLDDYVNTQGASLFSVTKKQLGAGSIEECAAKCEEDKEFTCR----
 4  1 -----MEHKEVVLLLLLLFLILFLKSGQG EPLDDYVNTQGASLFSVTKKQLGAGSIEECAAKCEEDKEFTCR----
 5  1 ----------MLMDYEGQG EPLDDYVNTKGASLFSITKKQLGAGSIEECAAKCEEBEEFTCR----
 6  1 -----MEHKEVVLLILLFLLFLKSGQG EPLDDYVNTQGASLFSVTKKQLGAGSIEECAAKCEEEKEFTCR----
 7  1 -----MEHKEVVLILLFLILFLKSGLG EPLDDYVNTQGAFLFSLSRKQVAARSVEECAAKCEAETNFICR----
 8  1 -----MDHKEVVLILLFLILFLKSGLG DSLDDYVNTQGASLLSLSRKNLAGRSVEDCAAKCEEETDFVCR----
 9  1 MLPASPKMEHKAVVFLILLFLILFLKSGHG DILDDYVTTQGASLFTFTRKPLSASSIEECEAKCTEETAFICR----
10  1 -----MEHQEVVFLLLFLILFLKSGHG DSLDGYISTQGASLFSLTKKQLAAGGVADCLAKCEGETDFVCR----
11  1 -----MDHKEVILLFLLLLFLKPGQG DSLDGYVSTQGASLHSLTKKQLAAGSIADCLAKCEGETDFICR----
12  1 -----MDHKEILLLFLLFLLFLQPGHG IPLDDYVTTQGASLSSSTKKQLSVGSTEECAVKCEKETSFICR----
13  1 -----MQRKELVLFLLLLFLLLKPGHG EPLDDYVNTQGASLFSVTKKQLGAASTAECAARCEAETEFTCR----
14  1 -----MEQRAVVLLILLLLKPGQA EPLDDYVNTQGASLFSFTKKQLGAASTAECAARCEAETEFTCR----
15  1 -----MEHKEVVLLLLLLFLLFLKSGQG EPLDDYVNTQGASLFSVTKKQLGAGSIEECAAKCEEDKEFTCRYFHCRCTYPEI
16  1 ----------------------------                                  FVRR
```

FIGURE 2B

FIGURE 2C

```
      121         131         141         151         161         171         181         191
       |           |           |           |           |           |           |           |
1  137 FSPATHPSEGLEENYCRNPDNDPQGPWCYTTDPEKRYDYCDILECEEECMHCSGENYDGKISKTMSGLECQAWDSQSPHA
2  137 YTPEKHPLEGLEENYCRNPDNDENGPWCYTTNPDVRFDYCNIPECEEECMHCSGENYEGKISKTKSGLECQAWNSQTPHA
3  137 FSPATHPSEGLEENYCRNPDNDPQGPWCYTTDPEKRYDYCDILECEEECMHCSGENYDGKISKTMSGLECQAWDSQSPHA
4  137 FSPATHPSEGLEENYCRNPDNDPQGPWCYTTDPEKRYDYCDILECEEECMHCSGENYDGKISKTMSGLECQAWDSQSPHA
5  137 FSPATHPSEGLEENYCRNPDNDPQGPWCYTTDPEKRYDYCDILECEEECMHCSGENYDGKISKTMSGLECQAWDSQSPHA
6  127 FSPATHPSEGLEENYCRNPDNDGQGPWCYTTDPEERFDYCDIPECEDECMHCSGENYDGKISKTMSGLECQAWDSQSPHA
7  137 FSPATHPSEGLEENYCRNPDNDAQGPWCYTTDPEHRYDYCDIPECEEACMHCSGENYDGKISKTMSGLECQAWDSQSPHA
8  137 YSPEKFPLAGLEENYCRNPDNDEKGPWCYTTDPETRFDYCDIPECEDECMHCSGEHYEGKISKTMSGLECQSWGSQSPHA
9  144 FSPEKFPLAGLEENYCRNPDNDENGPWCYTTDPDKRYDYCDIPECEDKCMHCSGENYEGKIAKTMSGRDCQAWDSQSPHA
10 137 YSPDKNPSEGLEENYCRNPDNDEKGPWCYTTDPGTRFDYCDIPECEDECMHCSGENYEGKISKTISGLECQPWASQSPHA
11 137 YSPSTHPSEGLEENYCRNPDNDEQGPWCYTTDPDKRYDYCNIPECEEECMYCSGEKYEGKISKTMSGLDCQSWDSQSPHA
12 137 YSPSTHPSEGLEENYCRNPDNDEQGPWCYTTDPDQRYEYCNIPECEEECMYCSGEKYEGKISKTMSGLDCQSWDSQSPHA
13 137 FSPDENPSEGLDQNYCRNPDNDPKGPWCYTMDPEVRYEYCEIIQCEDECMHCSGQNYVGKISRTMSGLECQPMDSQIPHP
14 137 FTPKKYPAEGLEENYCRNPDNDEQGPWCYTTNPDERFDYCDIPECEDECMHCSGENYEGKISKTMSGLECQAWDSQSPHA
15 154 FSPATHPSEGLEENYCRNPDNDPQGPWCYTTDPEKRYDYCDILECEEECMHCSGENYDGKISKTMSGLECQAWDSQSPHA
16  79 YTPEKHPLEGLEENYCRNPDNDEKGPWCYTTDPNQRFDYCSIPQCEDECMHCSGENYEGKVSKTKSGLECQAWNSQTPHA
```

FIGURE 2D

```
      201         211         221         231         241         251         261         271
1  217 HGYIPSKFPNKNLKKNYCRNPDGEPRPWCFTTDPNKRWELCDIPRCTTPPPSSGPTYQCLKGTGENYRGNVAVTVSGHTC
2  217 HGYIPSKFPSKNLKMNYCRNPDGEPRPWCFTMDPNKRWEFCDIPRCTTPPPSSGPTYQCLKGRGESYRGKVSVTVSGHTC
3  217 HGYIPSKFPNKNLKKNYCRNPDGELRPWCFTTDPNKRWELCDIPRCTTPPFPSSGPTYQCLKGTGENYRGNVAVTVSGHTC
4  217 HGYIPSKFPNKNLKKNYCRNPDGELRPWCFTTDPNKRWELCDIPRCTTPPPSSGPTYQCLKGTGENYRGNVAVTVSGHTC
5  207 HGYIPSKFPNKNLKKNYCRNPDGELRPWCFTTDPNKRWELCDIPRCTTPPPSSGPTYQCLKGTGENYRGNVAVTVSGHTC
6  217 HGYIPSKFPNKNLKKNYCRNPDGEPRPWCFTTDPNKRWELCDIPRCTTPPPSSGPTYQCLKGTGENYRGDVAVTVSGHTC
7  217 HGYIPSKFPNKNLKKNYCRNPDGEPRPWCFTTDPNKRWELCDIPRCTTPPPSSGPTYQCLKGTGENYRGNVAVTVSGHTC
8  217 HGYLPSKFPNKNLKMNYCRNPDGEPRPWCFTTDPNKRWEFCDIPRCTTPPPTSGPTYQCLKGRGENYRGTVSVTASGHTC
9  224 HGYIPSKFPSKNLKMNYCRNPDGEPRPWCFTTDPQKRWEFCDIPRCSTPPPSSGPKYQCLKGTGKNYGGTVAVTESGHTC
10 217 HGYIPSKFPNKNLRMNYCRNPDGEPRPWCFTMDPDKRWEFCDIPRCTTPPPPSGPTYQCLKGRGENYRGVSVTQSGLTC
11 217 HGFIPAKFPSKNLKMNYCRNPDGEPRPWCFTTDPTKRWEYCDIPRCTTPPFPGPTYQCLKGRGENYRGTVSVTVSGKTC
12 217 HGYIPAKFPSKNLKMNYCRNPDGEPRPWCFTTDPNKRWEYCDIPRCTTPPFPPSGPTYQCLMGNGEHYQGNVAVTASGKTC
13 217 HGYIPSKFPSKNLKMNYCRNPDGEPRPWCFTMDRNKRWEFCDIPRCTTPPFPPSGPTHQCLKGRGESYRGKVARTKSGLTC
14 217 HGYIPSKFPNKNLKKNYCRNPDGELRPWCFTMDPKKRWELCDIPRCTTPPFPSSGPTYQCLKGTGENYRGNVAVTVSGHTC
15 234 HGYIPSKFPNKNLKKNYCRNPDGELRPWCFTTDPNKRWELCDIPRCTTPPFPSSGPTYQCLKGKGENYRGKVSVTASGHTC
16 159 HGYIPSKFPNKLKMNYCRNPDGEPRPWCFTMDPNKRWEFCDIPRCTTPPFPPSGPTYQCLKGKGENYRGKVSVTASGHTC
```

FIGURE 2E

```
      261         291         301         311         321         331         341         351
       |           |           |           |           |           |           |           |
1  297 QHWSAQTPHTHNRTPENFPCKNLDENYCRNPDGKRAPWCHTTNSQVRWEYCKIPSCDSSPVSTEQLAPTA--PPE-LTPV
2  297 QHWSEQTPHKHNRTPENFPCKNLDENYCRNPDGETAPWCYTTNSEVRWEHCQIPSCESSPITTEYLDAPASVPPE-QTPV
3  297 QHWSAQTPHTHNRTPENFPCKNLDENYCRNPDGKRAPWCHTTNSQVRWEYCKIPSCDSSLVSTEQLAPTA--PPE-LTPV
4  297 QHWSAQTPHTHNRTPENFPCKNLDENYCRNPDGKRAPWCHTTNSQVRWEYCKIPSCDSSLVSTEQLAPTA--PPE-LTPV
5  287 QHWSAQTPHTHNRTPENFPCKNLDENYCRNPDGKRAPWCHTTNSQVRWEYCKIPSCDSSLVSTEQLAPTA--PPE-LTPV
6  297 HGWSAQTPHTHNRTPENFPCKNLDENYCRNPDGEKAPWCYTTNSQVRWEYCKIPSCESSPVSTEPLDPTA--PPE-LTPV
7  297 QRWSAQTPQTHNRTPENFPCKNLDENYCRNPDGEKAPWCYTTNSQVRWEYCKIPSCGSSPVSTEQLDPTA--PPE-LTPV
8  297 QRWSAQSPHKHNRTPENFPCKNLEENYCRNPDGETAPWCYTTDSEVRWDYCKIPSCGSSTTSTEYLDAPV--PPE-QTPV
9  304 QRWSEQTPHKHNRTPENFPCKNLDENYCRNPNGEKAPWCYTTNSKVRWEYCTIPSCESSPLSTERMDVPV--PPE-QTPV
10 297 QRWSEQTPHKHNRTPENFPDNFPCKNLDENYCRNPDGETAPWCYTTSSETRWEYCNIPSCTSSVPTEITDASE--PPE-QTPV
11 297 QRWSEQTPHRHNRTPENFPCKNLDENYCRNPDGETAPWCYTTDSQLRWEYCEIPSCESSASPDQ---SDSSVPPEEQTPV
12 297 QRWSEQTPHRHDRTPENYPCKNLDENYCRNPDGETAPWCYTTDSQLRWEYCEIPSCGSSVSPDQ---SDSSVLPE-QTPV
13 297 QRWGEQSPHRHNRTPENFPCKNLDENYCRNPDGEPAPWCFTTNSSVRWEFCKIPDCVSSASETEHSDAPVIVPPE-QTPV
14 297 QRWSEQTPHLHNRTPENFPCKDLDENYCRNPDGESAPWCYTTDSKVRWEHCDIPSCASSPTSVEPLDAPA--PPE-ETPV
15 314 QHWSEQTPHTHNRTPENFPCKNLDENYCRNPDGKRAPWCHTTNSQVRWEYCKIPSCDSSLVSTEQLAPTA--PPE-LTPV
16 239 QRWSEQTPHKHNRTPENFPCKNLDENYCRNPDGESAPWCYTTDSEVRWEHCSIPSCESSPLTLDSLDTPASIPPE-QTPV
```

FIGURE 2F

```
             361         371         381         391         401         411         421         431
              |           |           |           |           |           |           |           |
 1   374   VQDCYHGDGQSYRGTSSTTTTGKKCQSWSSMTPHRHQKTPENYPNAGLTMNYCRNPDAD-KGPWCFTTDPSVRWEYCNLK
 2   376   VQECYHGNGQSYRGTSSTITGKKCQSWSSMTPHRHEKTPEHFPEAGLTMNYCRNPDAD-KSPWCYTTDPSVRWEFCNLR
 3   374   VQDCYHGDGQSYRGTSSTTTTGKKCQSWSSMTPHRHQKTPENYPNAGLTMNYCRNPDAD-KGPWCFTTDPSVRWEYCNLK
 4   374   VQDCYHGDGQSYRGTSSTTTTGKKCQSWSSMTPHRHQKTPENYPNAGLTMNYCRNPDAD-KGPWCFTTDPSVRWEYCNLK
 5   364   VQDCYHGDGQSYRGTSSTTTTGKKCQSWSSMTPHRHEKTPENFPNAGLTMNYCRNPDAD-KGPWCFTTDPSVRWEYCNLK
 6   374   VQDCYHGDGQSYRGTSSTTTTGKKCQSWSSMTPHWHEKTPENYPNAGLTMNYCRNPDAD-KGPWCFTTDPSVRWEYCNLK
 7   374   VQDCYHGDGQSYRGTSSTTTTGKKCQSWSSMTPHWHQKTPENYPDAGLTMNYCRNPDAD-KGPWCFTTDPSVRWEYCNLK
 8   374   AQDCYRGNGESYRGTSSTTTTGRKCQSWVSMTPHRHEKTPGNFPNAGLTMNYCRNPDAD-KSPWCYTTDPRVRWEYCNLR
 9   381   PQDCYHGNGQSYRGTSSTTITGRKCQSWSSMTPHRHLKTPENYPEKYPNADLTMNYCRNPDGD-KSPWCYTTDPRVRWEFCNLR
10   374   VQDCYQDGDKGESYRGTSSITVTGKKCQSWSSMTPHWHQKTPEKYPNADLTMNYCRNPDGD-KGPWCYTTDPSVRWEFCNLR
11   374   VQECYQSDGQSYRGTSSTTITGKKCQSWAAMFPHRHSKTPENFFDAGLEMNYCRNPDGD-KGPWCYTTDPSVRWEYCNLR
12   373   VQECYQGNGKSYRGTSSTTNTGKKCQSWVSMTPHSHSKTPANFFDAGLEMNYCRNPDNDQRGPWCFTTDPSVRWEYCNLK
13   376   VQECYQGNGQSYRGTSSTTITGKKCQPWTSMRPHRHSKTPENYPDADLTMNYCRNPDGD-KGPWCYTTDPSVRWEYCNLR
14   374   VQECYQGNGQSYRGTSSTTITGRKCQSWLSMTPHRHQRTPQNYPNADLTMNYCRNPDDD-IRPWCYTTDPSVRWEYCNLR
15   391   VQDCYHGDGQSYRGTSSTTITGKKCQSWSSMSPHRHQKTPENYPNAGLTMNYCRNPDAD-KGPWCFTTDPSVRWEYCNLR
16   318   VQECYQGNGQTYRGTSSTTITGKKCQPWSSMSPHRHEKTPERFPNAGLTMNYCRNPDGD-KSPWCYTTDPSVRWEFCNLK
```

FIGURE 2G

```
     441        451        461        471        481        491        501        511
     |         |          |          |          |          |          |          |
1  453 KCSGTEASVVA-PPPVVLLPDVETPSEEDCMFGNGKGYRGKRATTVTGTPCQDWAAQEPHRHSIFTPETNPRA-GLEKNY
2  455 KCLDFEASATN-SPAVPQVPSGQEPSASDCMFGNGKGYRGKRATTVMGIPCQEWAAQEPHRHSIFTPETNPQA-GLEKNY
3  453 KCSGTEASVVA-PPPVVQLPNVETPSEEDCMFGNGKGYRGKRATTVTGTPCQDWAAQEPHRHSIFTPETNPRA-GLEKNY
4  453 KCSGTEASVVA-PPPVVQLPNVETPSEEDCMFGNGKGYRGKRATTVTGTPCQDWAAQEPHRHSIFTPETNPRA-GLEKNY
5  443 KCSGTEGSVAA-PPPVAQLPDAETPSEEDCMFGNGKGYRGKKATTVTGTPCQEWAAQEPHSHRIFTPETNPRA-GLEKNY
6  453 KCSGTEGSVVA-PPPVVQLPNVETPSEEDCMFGNGKGYRGKRATTVTGTPCQEWAAQEPHRHSIFTPETNPRA-GLEKNY
7  453 KCSGTEGSVVA-PPPVVQLPNVETPSEEDCMFGNGKGYRGKRATTVTGTPCQEWAAQEPHRHSIFTPQTNPRA-GLEKNY
8  453 KCSETEQQVTN-FPAIAQVPSVEDLSE-DCMFGNGKRYRGKSYRGKRATTVAGVPCQEWAAQEPHHHSIFTPETNPRA-GLEKNY
9  460 KCSETPEQV----PAAPQAFGVENPPEADCMIGMGKSYRGKGYQGKDYRGKTAVTAAGTPCQAWAAQEPHRHSIFTPETNPQS-GLEKNY
10 453 RCSETQQSFSNSSPTDTQVPSVQEPSEPDCMLGIGKGYQGKDYRGKDYRGKTAVTAAGTPCQGWAAQEPHRHSIFTPEANPWA-NLEKNY
11 453 RCSETGGSVVE-LPTVSQEPSGPSDSETDCMYGNGKDYRGKEYRGKTAVTAAGTPCQAWAAQEPHSHRIFTPQTNPRA-GLEKNY
12 453 RCSETGGGVAE-SAIVPQVPSAPGTSETDCMYGNGKEYRGKNGKYRGKTAVTAAGTPCQAWAAQEPHSHRIFTPQTNPRA-GLEKNY
13 455 KCSGTEMSATN-SSPV-QVSSASESSEQDCIIDNGKGYRGTKATTGAGTPCQAWAAQEPHRHNIFTPETNPRA-DLQENY
14 453 RCSEFAASPAA-TVPTAQLPRPEATFEPDCMFGNGKGYRGKKATTADGTPCQGWAAQEPHRHNIFTPETNPRA-GLEKNY
15 470 KCSGTEASVVA-PPPVVQLPNVETPSGEEPSETDCMFGNGKGYRGKRATTVTGTPCQDWAAQEPHKHSIFTPETNPRA-GLEKNY
16 397 KCLDTEESGTS-SPTVPQVPSGEEPSETDCMFGNGKGYRPGKYRGKKATTVTGTPCQEWTAQEPHKHSIFTPETNPRAEHLLCPT
17 1   ---------------IRLDCMFGNGKRYRGKRYRGKRATTVTGTPCQEWAAKEPHSHLIFTPETYPRA-GLEKNY
18 1   ---------APQAPSVENPPEADCMLGIGKGYRGKKATTVAGVPCQEWAAQEPHRHGIFTPETNPRA-GLEKNY
```

FIGURE 2H

```
                521        531        541        551        561        571
                 |          |          |          |          |          |
 1  531  CRNPDG------------DVGGPWCYTTNPRKLYDYCDVPQCAA-PSFDCGKPQVEPKKCPGRVVGGCVAHPHSWPWQ
 2  533  CRNPDG------------DVNGPWCYTTMNQRKLFDYCDVPQCVS-TSFDCGKPQVEPKKCPGRVVGGCVANPHSWPWQ
 3  531  CRNPDG------------DVGGPWCYTTNPRKLYDYCDVPQCAS-PSFDCGKPQVEPKKCPGRVVGGCVAHPHSWPWQ
 4  531  CRNPDG------------DVGGPWCYTTNPRKLYDYCDVPQCAS-PSFDCGKPQVEPKKCPGRVVGGCVAHPHSWPWQ
 5  521  CRNPDG------------DVGGPWCYTTNPRKLYDYCDVPQCAS-PSFDCGKPQVEPKKCPGRVVGGCVAHPHSWPWQ
 6  531  CRNPDG------------DVGGPWCYTTNPRKLFDYCDVPQCAA-SSFDCGKPQVEPKKCPGRVVGGCVAYPHSWPWQ
 7  531  CRNPDG------------DEGGPWCYTTNPRKLFDYCDVPQCAS-SSFDCGKPQVEPKKCPGRVVGGCVANAHSWPWQ
 8  530  CRNPDG------------DDNGPWCYTTNPQKLFDYCDVPQCVT-SSFDCGKPKVEPKKCPARVVGGCVSIPHSWPWQ
 9  535  CRNPDG------------DVNGPWCYTMNPQKLFDYCDVPQC-E-SSFDCGKPKVEPKKCSGRIVGGCVSKPHSWPWQ
10  532  CRNPDG------------DVNGPWCYTTNPRKLFDYCDVPQCES-SPFDCGKPKVEPKKCSGRIVGGCVAIAHSWPWQ
11  531  CRNPDG------------DVNGPWCYTTNPRKLYDYCDIPLCASASSFECGKPQVEPKKCPGRVVGGCVANPHSWPWQ
12  531  CRNPDG------------DVNGPWCYTTMNPRKLYDYCNIPLCASLSSFECGKPQVEPKKCPGRVVGGCVANPHSWPWQ
13  532  CRNPDG------------DANGPWCYTTNPRKLFDYCDIPHCVSPSSADCGKPKVEPKKCPGRVVGGCVANPHSWPWQ
14  531  CRNPDG------------DTNGPWCYTTNPRKLYDYCDVPQCASSSSYDCGKPKVEPKKCPGRVVGGCVANPHSWPWQ
15  548  CRNPDG------------DVGGPWCYTTNPRKLFDYCDVPQCAS-PSFDCGKPQVEPKKCPGRVVGGCVAHPHSWPWQ
16  476  CLVPSVPTVFFFFFLFLDVNGPWCYTTNPRKLFDYCDIPQCAS-GSFDCGKPQVEPKKCPGRVVGGCVANPHSWPWQ
17   55  CRNPDG------------DVGGPWCYTTNPRKLYDYCDVPQCAS-SSFDCGKPQVEPKKCPGRVVGGCVAHAHSWPWQ
18   65  CRNPDG------------DVNGPWCYTTNPRKLFDYCDIPQC-E-SSFDCGKPKVEPKKCPARVVGGCVATPHSWPWQ
```

FIGURE 2I

```
          581             591          601          611          621          631          641
          |               |            |            |            |            |            |
 1  596   VSLRTRF-GM-----HFCGGTLISPEWVLTAAHCLEKSPRPSSYKVILGAHQEVNLEPHVQEIEVSRLFLEPTRKDIALL
 2  598   ISLRTRY-GK-----HFCGGTLISPEWVLTAAHCLERSSRPASYKVILGAHKEVNLESDVQEIEVYKLFLEPTRADIALL
 3  596   VSLRTRL-GM-----HFCGGTLISPEWVLTAAHCLEKSPRPSSYKVILGAHQEVKLEPHVQEIEVSRLFLEPTRTDIALL
 4  596   VSLRTSS-NIAGKYWHFCGGTLISPEWVLTAAHCLEKSPRPSSYKVILGAHQEVKLEPHVQEIEVSRLFLEPTRTDIALL
 5  586   VSLRTRL-GM-----HFCGGTLISPEWVLTAAHCLEKSPRPSSYKVILGAHQEVKLEPHVQEIEVSRLFLEPTRTDIALL
 6  596   VSLRTRL-GM-----HFCGGTLISPEWVLTAAHCLERSSRPSFYKVILGAHREVHLEPHVQEIEVSKMFSEPARADIALL
 7  596   VSLRTRF-GT-----HFCGGTLISPEWVLTAAHCLEKSPRPSSYKVILGAHQEVNLEPHVQEIEVSRLFLEPTRADIALL
 8  595   ISLRHRY-GG-----HFCGGTLISPEWVLTAKHCLEKSSPSSYKVILGAHEEYHLGEGVQEIDVSKLFKEPSEADIALL
 9  599   VSLR-RS-SR-----HFCGGTLISPKWVLTAAHCLDNILALSFYKVILGAHNEKVREQSVQEIPVSRLFREPSQADIALL
10  597   ISLRTRF-GR-----HFCGGTLIAPEWVLTAAHCLERSSRPSTYKVVVLGTHHELRLAAGAQQIDVSKLFLEPSRADIALL
11  597   ISLRTRFTGQ-----HFCGGTLISPEWVLTAAHCLEKSSRPEFYKVILGAHEEYIRGSDVQEISVAKLIEPNNRDIALL
12  597   ISLRTRFSGQ-----HFCGGTLISPEWVLTAAHCLEKSSRPEFYKVILGAHEERILGSDVQQIAVTKLVLEPNDADIALL
13  598   VSLR-RF-GQ-----HFCGGTLISPEWVVTAAHCLEKFSNPAIYKVVLGAHQETRLERDVQIKGVTKMFLEPYRADIALL
14  597   ISLRTRF-GQ-----HFCGGTLIAPEWVLTAAHCLEKYPRPSAYRVILGAHKEVNLEDVQDIDVAKLFLEPSRADIALM
15  613   VSLRTRL-GM-----HFCGGTLISPEWVLTAAHCLEKSPRPSSYKVILGAHQEVKLEPHVQEIEVSRLFLEPTRTDIALL
16  555   ISLRTRF-GQ-----HFCGGTLISPEWVLTAAHCLERSPRPSFYKVILGAHREFNLESDVQEIEVRLEPHVQEIEVSKLFLEPTHADIALI
17  120   VSLRTRF-GM-----HFCGGTLISPEWVLTAAHCLEKSPRPSFYKVILGAHQEVRLEPHVQEIEVSKMFSEPAGADIALL
18  129   VSLRRRS-RE-----HFCGGTLISPEWVLTAAHCLDSILGPSFYTVILGAHYEMAREASVQEIPVSRLFLEPSRADIALL
```

FIGURE 2J

```
      651         661         671         681         691         701         711         721
        |           |           |           |           |           |           |           |
1  670  KLSSPAVITDKVIPACLPSPNYVVADRTECFITGWGETQGTFGAGLLKEAQLPVIENKVCNRYEFLNGRVQSTEL
2  672  KLSSPAVITSKVIPACLPPPNYVVADRTLCYITGWGETQGTYGAGLLKEAQLPVIENKVCNRYEYLNGRVKSTEL
3  670  KLSSPAIITDKVIPACLPSPNYVVADRTECFITGWGETQGTFGAGLLKEAQLPVIENKVCNREFLNGRVKSTEL
4  675  KLSSPAIITDKVIPACLPSPNYVVADRTECFITGWGETQGTFGAGLLKEAQLPVIENKVCNRNEFLNGRVKSTEL
5  660  KLSSPAIITDKVIPACLPSPNYVVADRTECFITGWGETQGTFGAGLLKEAQLPVIENKVCNRNEFLNGRVKSTEL
6  670  KLSSPAIITDKVIPACLPSPNYVVADRTECFITGWGETQGTYGAGLLKEARLPVIENKVCNRYEFLNGRVKSTEL
7  670  KLSSPAVITDKVIPACLPSPNYVVAGRTECFITGWGETQGTFGAGLLKEAQLPVIENKVCNRYEFLNGTVKTTEL
8  669  KLSSPAIITDKVIPACLPTPNYVVADRTACYITGWGETQGTFGAGLLKEAQLPVIENKVCNRYEFLNGRVKSTEL
9  672  KLSRPAIITKEVIPACLPPPNYMVAARTECVITGWGETQGTFGEGLLKEAHLPVIENKVCNREYLDGRVKPTEL
10 671  KLSRPAIITQNVIPACLPPADYVVANWAECFVTCWGETQDSSNAGVLKEAQLPVIENKVCNRVEYLNNRVKSTEL
11 672  KLSRPATITDKVIPACLPSPNYVVADRTLCYITGWGETQGTFGEAGRLKEAGRLKEAQLPVIENKVCNRAEYLNNRVKSTEL
12 672  KLSRPATITDNVIPACLPSPNYVVADRTLCYITGWGETQGTPGAGRLKEAQLPVIENKVCNRAEYLNNRVKSTEL
13 671  KLSSPAIIIPACLPNSNYMVADRSLCYITGWGETQGTYGAGLLKEAQLPVIENKVCNRQELLNGRVRSTEL
14 671  KLSSL----------------------------------------EWAWTYGAGLLKEAQLPVIENKVCNRFEYLNGRVKSTEL
15 687  KLSSPAIITDKVIPACLPSPNYVVADRTECFITGWGETQGTFGAGLLKEAQLPVIENKVCNREFLNGRVKSTEL
16 629  KLQSPAVLTSKVIPACLPSPNYVVADRTLCYITGWGETQGTFGVGLLKEAQLPVIENKVCNRYEYLNGKVKSTEL
17 194  KLSSPAIITDKVIPACLPSPNYVVADRTECFITGWGETQGTYGAGLLKEARLPVIENKVCNRYEFLNGRVKSTEL
18 203  KLSSPAVITDEVIPACLPSPNYVVADKTVCYITGWGETQGTFGVGRLKEARLPVIENKVCNRYEYLNGRVKSTEL
```

FIGURE 2K

```
         731        741        751        761        771        781        791
          |          |          |          |          |          |          |
 1   745  CAGHLAGGTDSCQGDSGGPLVCFEKDKYILQGVTSWGLGCARPNKPGVYYVRVSRFVTWIEGVMRNN  810
 2   747  CAGNLAGGTDSCQGDSGGPLVCFEKDKYILQGVTSWGLGCARPNKPGVYYVRVSRFVTWIEGIMRNN  812
 3   745  CAGHLAGGTDSCQGDSGGPLVCFEKDKYILQGVTSWGLGCARPNKPGVYYVRVSRFVTWIEGVMRNN  810
 4   750  CAGHLAGGTDSCQGDSGGPLVCFEKDKYILQGVTSWGLGCARPNKPGVYYVRVSRFVTWIEGVMRNN  815
 5   735  CAGHLAGGTDSCQGDSGGPLVCFEKDKYILQGVTSWGLGCARPNKPGVYYVRVSRFVTWIEGVMRNN  800
 6   745  CAGHLAGGTDSCQGDSGGPLVCFEKDKYILQGVTSWGLGCARPNKPGVYYVRVSRFVTWIEGVMRNN  810
 7   745  CAGHLAGGTDSCQGDSGGPLVCFEKDKYILQGVTSWGLGCARPNKPGVYYVRVSRFVTWIEGVMRNN  810
 8   744  CAGHLAGGTDSCQGDSGGPLVCFEKDRYILQGVTSWGLGCAIPNKPGVYYVRVSRFVTWIEEIMRNN  809
 9   747  CAGHLIGGTDSCQGDSGGPLVCFEKDKYILQGVTSWGLGCARPNKPGVYYVRVSPYVPWIEETMRRN  812
10   746  CAGQLAGGVDSCQGDSGGPLVCFEKDKYILQGVTSWGLGCARPNKPGVYYVRVSSFINWIERIMQSN  811
11   747  CAGHLAGGIDSCQGDSGGPLVCFEKDKYILQGVTSWGLGCARPNKPGVYYVRVSRFVDWIEREMRNN  812
12   747  CAGHLAGGVDSCQGDSGGPLVCFEKDKYILQGVTSWGLGCARPNKPGVYYVRVSRYVNWIEREMRND  812
13   746  CAGHLAGGVDSCQGDSGGPLVCFEKDKYILQGVTSWGLGCARPNKPGVYYVRVSRYVSMLQDVMRNN  811
14   715  CAGHLAGGTDSCQGDSGGPLVCFEKDKYILQGVTSWGLGCARPNKPGVYYVRVSRFVDWIERTMRNN  780
15   762  CAGNLAGGTDSCQGDSGGPLVCFEKDKYILQGVTSWGLGCARPNKPGVYYVRVSRFVTWIEGVMRNN  827
16   704  CAGHLAGGTDSCQGDSGGPLVCFEKDKYILQGVTSWGLGCARPNKPGVYYVRVSRFVTWIEEIMRNN  769
17   269  CAGHLAGGTDSCQGDSGGPLVCFEKDKYILQGVTSWGLGCARPNKPGVYYVRVSRFVTWIEGVMRNN  334
18   278  CAGDLAGGTDSCQGDSGGPLVCFEKDKYILQGVTSWGLGCARPNKPGVYYVRVSTYVPWIEETMRRY  343
```

FIGURE 2L

SEQUENCE LISTING

<160> NUMBER OF SEQ ID NOS: 27

<210> SEQ ID NO 1
<211> LENGTH: 791
<212> TYPE: PRT
<213> ORGANISM: Homo sapiens

<400> SEQUENCE: 1

```
Glu Pro Leu Asp Asp Tyr Val Asn Thr Gln Gly Ala Ser Leu Phe Ser
1               5                   10                  15

Val Thr Lys Lys Gln Leu Gly Ala Gly Ser Ile Glu Glu Cys Ala Ala
            20                  25                  30

Lys Cys Glu Glu Asp Glu Glu Phe Thr Cys Arg Ala Phe Gln Tyr His
        35                  40                  45

Ser Lys Glu Gln Gln Cys Val Ile Met Ala Glu Asn Arg Lys Ser Ser
    50                  55                  60

Ile Ile Ile Arg Met Arg Asp Val Val Leu Phe Glu Lys Lys Val Tyr
65                  70                  75                  80

Leu Ser Glu Cys Lys Thr Gly Asn Gly Lys Asn Tyr Arg Gly Thr Met
                85                  90                  95

Ser Lys Thr Lys Asn Gly Ile Thr Cys Gln Lys Trp Ser Ser Thr Ser
            100                 105                 110

Pro His Arg Pro Arg Phe Ser Pro Ala Thr His Pro Ser Glu Gly Leu
        115                 120                 125

Glu Glu Asn Tyr Cys Arg Asn Pro Asp Asn Asp Pro Gln Gly Pro Trp
    130                 135                 140

Cys Tyr Thr Thr Asp Pro Glu Lys Arg Tyr Asp Tyr Cys Asp Ile Leu
145                 150                 155                 160

Glu Cys Glu Glu Glu Cys Met His Cys Ser Gly Glu Asn Tyr Asp Gly
                165                 170                 175

Lys Ile Ser Lys Thr Met Ser Gly Leu Glu Cys Gln Ala Trp Asp Ser
            180                 185                 190

Gln Ser Pro His Ala His Gly Tyr Ile Pro Ser Lys Phe Pro Asn Lys
        195                 200                 205

Asn Leu Lys Lys Asn Tyr Cys Arg Asn Pro Asp Arg Glu Leu Arg Pro
    210                 215                 220

Trp Cys Phe Thr Thr Asp Pro Asn Lys Arg Trp Glu Leu Cys Asp Ile
225                 230                 235                 240

Pro Arg Cys Thr Thr Pro Pro Pro Ser Ser Gly Pro Thr Tyr Gln Cys
                245                 250                 255

Leu Lys Gly Thr Gly Glu Asn Tyr Arg Gly Asn Val Ala Val Thr Val
            260                 265                 270

Ser Gly His Thr Cys Gln His Trp Ser Ala Gln Thr Pro His Thr His
        275                 280                 285

Asn Arg Thr Pro Glu Asn Phe Pro Cys Lys Asn Leu Asp Glu Asn Tyr
    290                 295                 300

Cys Arg Asn Pro Asp Gly Lys Arg Ala Pro Trp Cys His Thr Thr Asn
305                 310                 315                 320

Ser Gln Val Arg Trp Glu Tyr Cys Lys Ile Pro Ser Cys Asp Ser Ser
                325                 330                 335

Pro Val Ser Thr Glu Gln Leu Ala Pro Thr Ala Pro Pro Glu Leu Thr
            340                 345                 350

Pro Val Val Gln Asp Cys Tyr His Gly Asp Gly Gln Ser Tyr Arg Gly
        355                 360                 365
```

```
Thr Ser Ser Thr Thr Thr Thr Gly Lys Lys Cys Gln Ser Trp Ser Ser
    370                 375                 380

Met Thr Pro His Arg His Gln Lys Thr Pro Glu Asn Tyr Pro Asn Ala
385                 390                 395                 400

Gly Leu Thr Met Asn Tyr Cys Arg Asn Pro Asp Ala Asp Lys Gly Pro
                405                 410                 415

Trp Cys Phe Thr Thr Asp Pro Ser Val Arg Trp Glu Tyr Cys Asn Leu
            420                 425                 430

Lys Lys Cys Ser Gly Thr Glu Ala Ser Val Val Ala Pro Pro Pro Val
        435                 440                 445

Val Leu Leu Pro Asp Val Glu Thr Pro Ser Glu Glu Asp Cys Met Phe
    450                 455                 460

Gly Asn Gly Lys Gly Tyr Arg Gly Lys Arg Ala Thr Thr Val Thr Gly
465                 470                 475                 480

Thr Pro Cys Gln Asp Trp Ala Ala Gln Glu Pro His Arg His Ser Ile
                485                 490                 495

Phe Thr Pro Glu Thr Asn Pro Arg Ala Gly Leu Glu Lys Asn Tyr Cys
            500                 505                 510

Arg Asn Pro Asp Gly Asp Val Gly Gly Pro Trp Cys Tyr Thr Thr Asn
        515                 520                 525

Pro Arg Lys Leu Tyr Asp Tyr Cys Asp Val Pro Gln Cys Ala Ala Pro
    530                 535                 540

Ser Phe Asp Cys Gly Lys Pro Gln Val Glu Pro Lys Lys Cys Pro Gly
545                 550                 555                 560

Arg Val Val Gly Gly Cys Val Ala His Pro His Ser Trp Pro Trp Gln
                565                 570                 575

Val Ser Leu Arg Thr Arg Phe Gly Met His Phe Cys Gly Gly Thr Leu
            580                 585                 590

Ile Ser Pro Glu Trp Val Leu Thr Ala Ala His Cys Leu Glu Lys Ser
        595                 600                 605

Pro Arg Pro Ser Ser Tyr Lys Val Ile Leu Gly Ala His Gln Glu Val
    610                 615                 620

Asn Leu Glu Pro His Val Gln Glu Ile Glu Val Ser Arg Leu Phe Leu
625                 630                 635                 640

Glu Pro Thr Arg Lys Asp Ile Ala Leu Leu Lys Leu Ser Ser Pro Ala
                645                 650                 655

Val Ile Thr Asp Lys Val Ile Pro Ala Cys Leu Pro Ser Pro Asn Tyr
            660                 665                 670

Val Val Ala Asp Arg Thr Glu Cys Phe Ile Thr Gly Trp Gly Glu Thr
        675                 680                 685

Gln Gly Thr Phe Gly Ala Gly Leu Leu Lys Glu Ala Gln Leu Pro Val
    690                 695                 700

Ile Glu Asn Lys Val Cys Asn Arg Tyr Glu Phe Leu Asn Gly Arg Val
705                 710                 715                 720

Gln Ser Thr Glu Leu Cys Ala Gly His Leu Ala Gly Gly Thr Asp Ser
                725                 730                 735

Cys Gln Gly Asp Ser Gly Gly Pro Leu Val Cys Phe Glu Lys Asp Lys
            740                 745                 750

Tyr Ile Leu Gln Gly Val Thr Ser Trp Gly Leu Gly Cys Ala Arg Pro
        755                 760                 765
```

```
Asn Lys Pro Gly Val Tyr Val Arg Val Ser Arg Phe Val Thr Trp Ile
    770                 775                 780

Glu Gly Val Met Arg Asn Asn
785                 790

<210> SEQ ID NO 2
<211> LENGTH: 812
<212> TYPE: PRT
<213> ORGANISM: Canis familiaris

<400> SEQUENCE: 2

Met Glu His Lys Glu Val Val Leu Leu Leu Leu Phe Leu Lys Ser
1               5                   10                  15

Gly His Gly Ser Leu Leu Asp Asp Tyr Val Asn Thr Gln Gly Ala Ser
                20                  25                  30

Val Phe Ser Leu Thr Lys Lys Gln Leu Ser Val Gly Ser Ile Glu Glu
                35                  40                  45

Cys Ala Ala Lys Cys Glu Glu Glu Thr Gly Phe Ile Cys Arg Ser Phe
            50                  55                  60

Gln Tyr His Ser Lys Glu Gln Gln Cys Val Ile Met Pro Glu Asn Ser
65                  70                  75                  80

Lys Ser Ser Ile Val Phe Arg Met Arg Asp Val Phe Leu Phe Glu Lys
                85                  90                  95

Arg Ile Tyr Leu Ser Glu Cys Lys Thr Gly Asn Gly Lys Thr Tyr Arg
            100                 105                 110

Gly Thr Met Ala Lys Thr Lys Asn Asp Val Ala Cys Gln Lys Trp Ser
            115                 120                 125

Asp Asn Ser Pro His Lys Pro Asn Tyr Thr Pro Glu Lys His Pro Leu
130                 135                 140

Glu Gly Leu Glu Glu Asn Tyr Cys Arg Asn Pro Asp Asn Asp Glu Asn
145                 150                 155                 160

Gly Pro Trp Cys Tyr Thr Thr Asn Pro Asp Val Arg Phe Asp Tyr Cys
                165                 170                 175

Asn Ile Pro Glu Cys Glu Glu Glu Cys Met His Cys Ser Gly Glu Asn
            180                 185                 190

Tyr Glu Gly Lys Ile Ser Lys Thr Lys Ser Gly Leu Glu Cys Gln Ala
            195                 200                 205

Trp Asn Ser Gln Thr Pro His Ala His Gly Tyr Ile Pro Ser Lys Phe
210                 215                 220

Pro Ser Lys Asn Leu Lys Met Asn Tyr Cys Arg Asn Pro Asp Gly Glu
225                 230                 235                 240

Pro Arg Pro Trp Cys Phe Thr Met Asp Pro Asn Lys Arg Trp Glu Phe
                245                 250                 255

Cys Asp Ile Pro Arg Cys Thr Thr Pro Pro Pro Ser Gly Pro Thr
            260                 265                 270

Tyr Gln Cys Leu Lys Gly Arg Gly Glu Ser Tyr Arg Gly Lys Val Ser
            275                 280                 285

Val Thr Val Ser Gly His Thr Cys Gln His Trp Ser Glu Gln Thr Pro
290                 295                 300

His Lys His Asn Arg Thr Pro Glu Asn Phe Pro Cys Lys Asn Leu Asp
305                 310                 315                 320

Glu Asn Tyr Cys Arg Asn Pro Asp Gly Glu Thr Ala Pro Trp Cys Tyr
                325                 330                 335

Thr Thr Asn Ser Glu Val Arg Trp Glu His Cys Gln Ile Pro Ser Cys
            340                 345                 350
```

-continued

```
Glu Ser Ser Pro Ile Thr Thr Glu Tyr Leu Asp Ala Pro Ala Ser Val
        355                 360                 365

Pro Pro Glu Gln Thr Pro Val Val Gln Glu Cys Tyr His Gly Asn Gly
370                 375                 380

Gln Ser Tyr Arg Gly Thr Ser Ser Thr Ile Thr Gly Arg Lys Cys
385                 390                 395                 400

Gln Ser Trp Ser Ser Met Thr Pro His Arg His Glu Lys Thr Pro Glu
                405                 410                 415

His Phe Pro Glu Ala Gly Leu Thr Met Asn Tyr Cys Arg Asn Pro Asp
                420                 425                 430

Ala Asp Lys Ser Pro Trp Cys Tyr Thr Thr Asp Pro Ser Val Arg Trp
        435                 440                 445

Glu Phe Cys Asn Leu Arg Lys Cys Leu Asp Pro Glu Ala Ser Ala Thr
450                 455                 460

Asn Ser Pro Ala Val Pro Gln Val Pro Ser Gly Gln Glu Pro Ser Ala
465                 470                 475                 480

Ser Asp Cys Met Phe Gly Asn Gly Lys Gly Tyr Arg Gly Lys Lys Ala
                485                 490                 495

Thr Thr Val Met Gly Ile Pro Cys Gln Glu Trp Ala Ala Gln Glu Pro
                500                 505                 510

His Arg His Ser Ile Phe Thr Pro Glu Thr Asn Pro Gln Ala Gly Leu
        515                 520                 525

Glu Lys Asn Tyr Cys Arg Asn Pro Asp Gly Asp Val Asn Gly Pro Trp
        530                 535                 540

Cys Tyr Thr Met Asn Gln Arg Lys Leu Phe Asp Tyr Cys Asp Val Pro
545                 550                 555                 560

Gln Cys Val Ser Thr Ser Phe Asp Cys Gly Lys Pro Gln Val Glu Pro
                565                 570                 575

Lys Lys Cys Pro Gly Arg Val Val Gly Gly Cys Val Ala Asn Pro His
            580                 585                 590

Ser Trp Pro Trp Gln Ile Ser Leu Arg Thr Arg Tyr Gly Lys His Phe
        595                 600                 605

Cys Gly Gly Thr Leu Ile Ser Pro Glu Trp Val Leu Thr Ala Ala His
        610                 615                 620

Cys Leu Glu Arg Ser Ser Arg Pro Ala Ser Tyr Lys Val Ile Leu Gly
625                 630                 635                 640

Ala His Lys Glu Val Asn Leu Glu Ser Asp Val Gln Glu Ile Glu Val
                645                 650                 655

Tyr Lys Leu Phe Leu Glu Pro Thr Arg Ala Asp Ile Ala Leu Leu Lys
                660                 665                 670

Leu Ser Ser Pro Ala Val Ile Thr Ser Lys Val Ile Pro Ala Cys Leu
        675                 680                 685

Pro Pro Pro Asn Tyr Val Val Ala Asp Arg Thr Leu Cys Tyr Ile Thr
690                 695                 700

Gly Trp Gly Glu Thr Gln Gly Thr Tyr Gly Ala Gly Leu Leu Lys Glu
705                 710                 715                 720

Ala Gln Leu Pro Val Ile Glu Asn Lys Val Cys Asn Arg Tyr Glu Tyr
                725                 730                 735

Leu Asn Gly Arg Val Lys Ser Thr Glu Leu Cys Ala Gly Asn Leu Ala
                740                 745                 750

Gly Gly Thr Asp Ser Cys Gln Gly Asp Ser Gly Gly Pro Leu Val Cys
        755                 760                 765
```

```
Phe Glu Lys Asp Lys Tyr Ile Leu Gln Gly Val Thr Ser Trp Gly Leu
770                 775                 780
Gly Cys Ala Arg Pro Asn Lys Pro Gly Val Tyr Val Arg Val Ser Arg
785                 790                 795                 800
Phe Val Thr Trp Ile Glu Gly Ile Met Arg Asn Asn
                805                 810

<210> SEQ ID NO 3
<211> LENGTH: 810
<212> TYPE: PRT
<213> ORGANISM: Pan troglodytes

<400> SEQUENCE: 3

Met Glu His Lys Glu Val Val Leu Leu Leu Leu Phe Leu Lys Ser
1               5                   10                  15

Gly Gln Gly Glu Pro Leu Asp Asp Tyr Val Asn Thr Gln Gly Ala Ser
                20                  25                  30

Leu Phe Ser Val Thr Lys Lys Gln Leu Gly Ala Gly Ser Ile Glu Glu
            35                  40                  45

Cys Ala Ala Lys Cys Glu Glu Asp Lys Glu Phe Thr Cys Arg Ala Phe
50                  55                  60

Gln Tyr His Ser Lys Glu Gln Gln Cys Val Ile Met Ala Glu Asn Arg
65                  70                  75                  80

Lys Ser Ser Ile Ile Ile Arg Met Arg Asp Val Val Leu Phe Glu Lys
                85                  90                  95

Lys Val Tyr Leu Ser Glu Cys Lys Thr Gly Asn Gly Lys Asn Tyr Arg
            100                 105                 110

Gly Thr Met Ser Lys Thr Lys Asn Gly Ile Thr Cys Gln Lys Trp Ser
        115                 120                 125

Ser Thr Ser Pro His Arg Pro Arg Phe Ser Pro Ala Thr His Pro Ser
    130                 135                 140

Glu Gly Leu Glu Glu Asn Tyr Cys Arg Asn Pro Asp Asn Asp Pro Gln
145                 150                 155                 160

Gly Pro Trp Cys Tyr Thr Thr Asp Pro Glu Lys Arg Tyr Asp Tyr Cys
                165                 170                 175

Asp Ile Leu Glu Cys Glu Glu Glu Cys Met His Cys Ser Gly Glu Asn
            180                 185                 190

Tyr Asp Gly Lys Ile Ser Lys Thr Met Ser Gly Leu Glu Cys Gln Ala
        195                 200                 205

Trp Asp Ser Gln Ser Pro His Ala His Gly Tyr Ile Pro Ser Lys Phe
    210                 215                 220

Pro Asn Lys Asn Leu Lys Lys Asn Tyr Cys Arg Asn Pro Asp Gly Glu
225                 230                 235                 240

Leu Arg Pro Trp Cys Phe Thr Thr Asp Pro Asn Lys Arg Trp Glu Leu
                245                 250                 255

Cys Asp Ile Pro Arg Cys Thr Thr Pro Pro Pro Ser Ser Gly Pro Thr
            260                 265                 270

Tyr Gln Cys Leu Lys Gly Thr Gly Glu Asn Tyr Arg Gly Asn Val Ala
        275                 280                 285

Val Thr Val Ser Gly His Thr Cys Gln His Trp Ser Ala Gln Thr Pro
    290                 295                 300

His Thr His Asn Arg Thr Pro Glu Asn Phe Pro Cys Lys Asn Leu Asp
305                 310                 315                 320

Glu Asn Tyr Cys Arg Asn Pro Asp Gly Lys Arg Ala Pro Trp Cys His
                325                 330                 335
```

```
Thr Thr Asn Ser Gln Val Arg Trp Glu Tyr Cys Lys Ile Pro Ser Cys
            340                 345                 350

Asp Ser Ser Leu Val Ser Thr Glu Gln Leu Ala Pro Thr Ala Pro Pro
            355                 360                 365

Glu Leu Thr Pro Val Val Gln Asp Cys Tyr His Gly Asp Gly Gln Ser
            370                 375                 380

Tyr Arg Gly Thr Ser Ser Thr Thr Thr Gly Lys Lys Cys Gln Ser
385                     390                 395                 400

Trp Ser Ser Met Thr Pro His Arg His Gln Lys Thr Pro Glu Asn Tyr
                405                 410                 415

Pro Asn Ala Gly Leu Thr Met Asn Tyr Cys Arg Asn Pro Asp Ala Asp
            420                 425                 430

Lys Gly Pro Trp Cys Phe Thr Thr Asp Pro Ser Val Arg Trp Glu Tyr
            435                 440                 445

Cys Asn Leu Lys Lys Cys Ser Gly Thr Glu Ala Ser Val Val Ala Pro
            450                 455                 460

Pro Pro Val Val Gln Leu Pro Asn Val Glu Thr Pro Ser Glu Glu Asp
465                     470                 475                 480

Cys Met Phe Gly Asn Gly Lys Gly Tyr Arg Gly Lys Arg Ala Thr Thr
                485                 490                 495

Val Thr Gly Thr Pro Cys Gln Asp Trp Ala Ala Gln Glu Pro His Arg
            500                 505                 510

His Ser Ile Phe Thr Pro Glu Thr Asn Pro Arg Ala Gly Leu Glu Lys
            515                 520                 525

Asn Tyr Cys Arg Asn Pro Asp Gly Asp Val Gly Gly Pro Trp Cys Tyr
            530                 535                 540

Thr Thr Asn Pro Arg Lys Leu Tyr Asp Tyr Cys Asp Val Pro Gln Cys
545                     550                 555                 560

Ala Ser Pro Ser Phe Asp Cys Gly Lys Pro Gln Val Glu Pro Lys Lys
                565                 570                 575

Cys Pro Gly Arg Val Val Gly Gly Cys Val Ala His Pro His Ser Trp
            580                 585                 590

Pro Trp Gln Val Ser Leu Arg Thr Arg Leu Gly Met His Phe Cys Gly
            595                 600                 605

Gly Thr Leu Ile Ser Pro Glu Trp Val Leu Thr Ala Ala His Cys Leu
            610                 615                 620

Glu Lys Ser Pro Arg Pro Ser Ser Tyr Lys Val Ile Leu Gly Ala His
625                     630                 635                 640

Gln Glu Val Lys Leu Glu Pro His Val Gln Glu Ile Glu Val Ser Arg
                645                 650                 655

Leu Phe Leu Glu Pro Thr Arg Thr Asp Ile Ala Leu Leu Lys Leu Ser
            660                 665                 670

Ser Pro Ala Ile Ile Thr Asp Lys Val Ile Pro Ala Cys Leu Pro Ser
            675                 680                 685

Pro Asn Tyr Val Val Ala Asp Arg Thr Glu Cys Phe Ile Thr Gly Trp
            690                 695                 700

Gly Glu Thr Gln Gly Thr Phe Gly Ala Gly Leu Leu Lys Glu Ala Gln
705                     710                 715                 720

Leu Pro Val Ile Glu Asn Lys Val Cys Asn Arg Asn Glu Phe Leu Asn
                725                 730                 735

Gly Arg Val Lys Ser Thr Glu Leu Cys Ala Gly His Leu Ala Gly Gly
            740                 745                 750
```

```
Thr Asp Ser Cys Gln Gly Asp Ser Gly Pro Leu Val Cys Phe Glu
            755                 760                 765
Lys Asp Lys Tyr Ile Leu Gln Gly Val Thr Ser Trp Gly Leu Gly Cys
    770                 775                 780
Ala Arg Pro Asn Lys Pro Gly Val Tyr Val Arg Val Ser Arg Phe Val
785                 790                 795                 800
Thr Trp Ile Glu Gly Val Met Arg Asn Asn
                805                 810

<210> SEQ ID NO 4
<211> LENGTH: 815
<212> TYPE: PRT
<213> ORGANISM: Pan troglodytes

<400> SEQUENCE: 4

Met Glu His Lys Glu Val Val Leu Leu Leu Leu Phe Leu Lys Ser
1               5                   10                  15
Gly Gln Gly Glu Pro Leu Asp Asp Tyr Val Asn Thr Gln Gly Ala Ser
                20                  25                  30
Leu Phe Ser Val Thr Lys Lys Gln Leu Gly Ala Gly Ser Ile Glu Glu
            35                  40                  45
Cys Ala Ala Lys Cys Glu Glu Asp Lys Glu Phe Thr Cys Arg Ala Phe
    50                  55                  60
Gln Tyr His Ser Lys Glu Gln Gln Cys Val Ile Met Ala Glu Asn Arg
65                  70                  75                  80
Lys Ser Ser Ile Ile Ile Arg Met Arg Asp Val Val Leu Phe Glu Lys
                85                  90                  95
Lys Val Tyr Leu Ser Glu Cys Lys Thr Gly Asn Gly Lys Asn Tyr Arg
            100                 105                 110
Gly Thr Met Ser Lys Thr Lys Asn Gly Ile Thr Cys Gln Lys Trp Ser
        115                 120                 125
Ser Thr Ser Pro His Arg Pro Arg Phe Ser Pro Ala Thr His Pro Ser
    130                 135                 140
Glu Gly Leu Glu Glu Asn Tyr Cys Arg Asn Pro Asp Asn Asp Pro Gln
145                 150                 155                 160
Gly Pro Trp Cys Tyr Thr Thr Asp Pro Glu Lys Arg Tyr Asp Tyr Cys
                165                 170                 175
Asp Ile Leu Glu Cys Glu Glu Cys Met His Cys Ser Gly Glu Asn
            180                 185                 190
Tyr Asp Gly Lys Ile Ser Lys Thr Met Ser Gly Leu Glu Cys Gln Ala
        195                 200                 205
Trp Asp Ser Gln Ser Pro His Ala His Gly Tyr Ile Pro Ser Lys Phe
    210                 215                 220
Pro Asn Lys Asn Leu Lys Lys Asn Tyr Cys Arg Asn Pro Asp Gly Glu
225                 230                 235                 240
Leu Arg Pro Trp Cys Phe Thr Thr Asp Pro Asn Lys Arg Trp Glu Leu
                245                 250                 255
Cys Asp Ile Pro Arg Cys Thr Thr Pro Pro Ser Ser Gly Pro Thr
            260                 265                 270
Tyr Gln Cys Leu Lys Gly Thr Gly Glu Asn Tyr Arg Gly Asn Val Ala
        275                 280                 285
Val Thr Val Ser Gly His Thr Cys Gln His Trp Ser Ala Gln Thr Pro
    290                 295                 300
His Thr His Asn Arg Thr Pro Glu Asn Phe Pro Cys Lys Asn Leu Asp
305                 310                 315                 320
```

-continued

Glu Asn Tyr Cys Arg Asn Pro Asp Gly Lys Arg Ala Pro Trp Cys His
              325                 330                 335
Thr Thr Asn Ser Gln Val Arg Trp Glu Tyr Cys Lys Ile Pro Ser Cys
              340                 345                 350
Asp Ser Ser Leu Val Ser Thr Glu Gln Leu Ala Pro Thr Ala Pro Pro
              355                 360                 365
Glu Leu Thr Pro Val Val Gln Asp Cys Tyr His Gly Asp Gly Gln Ser
          370                 375                 380
Tyr Arg Gly Thr Ser Ser Thr Thr Thr Gly Lys Lys Cys Gln Ser
385                 390                 395                 400
Trp Ser Ser Met Thr Pro His Arg His Gln Lys Thr Pro Glu Asn Tyr
                  405                 410                 415
Pro Asn Ala Gly Leu Thr Met Asn Tyr Cys Arg Asn Pro Asp Ala Asp
              420                 425                 430
Lys Gly Pro Trp Cys Phe Thr Thr Asp Pro Ser Val Arg Trp Glu Tyr
              435                 440                 445
Cys Asn Leu Lys Lys Cys Ser Gly Thr Glu Ala Ser Val Val Ala Pro
          450                 455                 460
Pro Pro Val Val Gln Leu Pro Asn Val Glu Thr Pro Ser Glu Glu Asp
465                 470                 475                 480
Cys Met Phe Gly Asn Gly Lys Gly Tyr Arg Gly Lys Arg Ala Thr Thr
                  485                 490                 495
Val Thr Gly Thr Pro Cys Gln Asp Trp Ala Ala Gln Glu Pro His Arg
              500                 505                 510
His Ser Ile Phe Thr Pro Glu Thr Asn Pro Arg Ala Gly Leu Glu Lys
              515                 520                 525
Asn Tyr Cys Arg Asn Pro Asp Gly Asp Val Gly Gly Pro Trp Cys Tyr
          530                 535                 540
Thr Thr Asn Pro Arg Lys Leu Tyr Asp Tyr Cys Asp Val Pro Gln Cys
545                 550                 555                 560
Ala Ser Pro Ser Phe Asp Cys Gly Lys Pro Gln Val Glu Pro Lys Lys
                  565                 570                 575
Cys Pro Gly Arg Val Val Gly Gly Cys Val Ala His Pro His Ser Trp
              580                 585                 590
Pro Trp Gln Val Ser Leu Arg Thr Ser Ser Asn Ile Ala Gly Lys Tyr
              595                 600                 605
Trp His Phe Cys Gly Gly Thr Leu Ile Ser Pro Glu Trp Val Leu Thr
          610                 615                 620
Ala Ala His Cys Leu Glu Lys Ser Pro Arg Pro Ser Ser Tyr Lys Val
625                 630                 635                 640
Ile Leu Gly Ala His Gln Glu Val Lys Leu Glu Pro His Val Gln Glu
                  645                 650                 655
Ile Glu Val Ser Arg Leu Phe Leu Glu Pro Thr Arg Thr Asp Ile Ala
              660                 665                 670
Leu Leu Lys Leu Ser Ser Pro Ala Ile Ile Thr Asp Lys Val Ile Pro
              675                 680                 685
Ala Cys Leu Pro Ser Pro Asn Tyr Val Val Ala Asp Arg Thr Glu Cys
          690                 695                 700
Phe Ile Thr Gly Trp Gly Glu Thr Gln Gly Thr Phe Gly Ala Gly Leu
705                 710                 715                 720
Leu Lys Glu Ala Gln Leu Pro Val Ile Glu Asn Lys Val Cys Asn Arg
                  725                 730                 735

```
Asn Glu Phe Leu Asn Gly Arg Val Lys Ser Thr Glu Leu Cys Ala Gly
                740                 745                 750

His Leu Ala Gly Gly Thr Asp Ser Cys Gln Gly Asp Ser Gly Gly Pro
            755                 760                 765

Leu Val Cys Phe Glu Lys Asp Lys Tyr Ile Leu Gln Gly Val Thr Ser
        770                 775                 780

Trp Gly Leu Gly Cys Ala Arg Pro Asn Lys Pro Gly Val Tyr Val Arg
785                 790                 795                 800

Val Ser Arg Phe Val Thr Trp Ile Glu Gly Val Met Arg Asn Asn
                805                 810                 815

<210> SEQ ID NO 5
<211> LENGTH: 800
<212> TYPE: PRT
<213> ORGANISM: Pan troglodytes

<400> SEQUENCE: 5

Met Leu Met Asp Tyr Glu Gly Gln Gly Glu Pro Leu Asp Asp Tyr Val
1               5                   10                  15

Asn Thr Gln Gly Ala Ser Leu Phe Ser Val Thr Lys Lys Gln Leu Gly
                20                  25                  30

Ala Gly Ser Ile Glu Glu Cys Ala Ala Lys Cys Glu Glu Asp Lys Glu
            35                  40                  45

Phe Thr Cys Arg Ala Phe Gln Tyr His Ser Lys Glu Gln Gln Cys Val
        50                  55                  60

Ile Met Ala Glu Asn Arg Lys Ser Ser Ile Ile Arg Met Arg Asp
65                  70                  75                  80

Val Val Leu Phe Glu Lys Lys Val Tyr Leu Ser Glu Cys Lys Thr Gly
                85                  90                  95

Asn Gly Lys Asn Tyr Arg Gly Thr Met Ser Lys Thr Lys Asn Gly Ile
                100                 105                 110

Thr Cys Gln Lys Trp Ser Ser Thr Ser Pro His Arg Pro Arg Phe Ser
            115                 120                 125

Pro Ala Thr His Pro Ser Glu Gly Leu Glu Glu Asn Tyr Cys Arg Asn
        130                 135                 140

Pro Asp Asn Asp Pro Gln Gly Pro Trp Cys Tyr Thr Thr Asp Pro Glu
145                 150                 155                 160

Lys Arg Tyr Asp Tyr Cys Asp Ile Leu Glu Cys Glu Glu Glu Cys Met
                165                 170                 175

His Cys Ser Gly Glu Asn Tyr Asp Gly Lys Ile Ser Lys Thr Met Ser
            180                 185                 190

Gly Leu Glu Cys Gln Ala Trp Asp Ser Gln Ser Pro His Ala His Gly
        195                 200                 205

Tyr Ile Pro Ser Lys Phe Pro Asn Lys Asn Leu Lys Lys Asn Tyr Cys
        210                 215                 220

Arg Asn Pro Asp Gly Glu Leu Arg Pro Trp Cys Phe Thr Thr Asp Pro
225                 230                 235                 240

Asn Lys Arg Trp Glu Leu Cys Asp Ile Pro Arg Cys Thr Thr Pro Pro
                245                 250                 255

Pro Ser Ser Gly Pro Thr Tyr Gln Cys Leu Lys Gly Thr Gly Glu Asn
            260                 265                 270

Tyr Arg Gly Asn Val Ala Val Thr Val Ser Gly His Thr Cys Gln His
        275                 280                 285

Trp Ser Ala Gln Thr Pro His Thr His Asn Arg Thr Pro Glu Asn Phe
        290                 295                 300
```

```
Pro Cys Lys Asn Leu Asp Glu Asn Tyr Cys Arg Asn Pro Asp Gly Lys
305                 310                 315                 320

Arg Ala Pro Trp Cys His Thr Thr Asn Ser Gln Val Arg Trp Glu Tyr
                325                 330                 335

Cys Lys Ile Pro Ser Cys Asp Ser Ser Leu Val Ser Thr Glu Gln Leu
            340                 345                 350

Ala Pro Thr Ala Pro Pro Glu Leu Thr Pro Val Val Gln Asp Cys Tyr
        355                 360                 365

His Gly Asp Gly Gln Ser Tyr Arg Gly Thr Ser Ser Thr Thr Thr Thr
    370                 375                 380

Gly Lys Lys Cys Gln Ser Trp Ser Ser Met Thr Pro His Arg His Gln
385                 390                 395                 400

Lys Thr Pro Glu Asn Tyr Pro Asn Ala Gly Leu Thr Met Asn Tyr Cys
                405                 410                 415

Arg Asn Pro Asp Ala Asp Lys Gly Pro Trp Cys Phe Thr Thr Asp Pro
            420                 425                 430

Ser Val Arg Trp Glu Tyr Cys Asn Leu Lys Lys Cys Ser Gly Thr Glu
        435                 440                 445

Ala Ser Val Val Ala Pro Pro Val Val Gln Leu Pro Asn Val Glu
    450                 455                 460

Thr Pro Ser Glu Glu Asp Cys Met Phe Gly Asn Gly Lys Gly Tyr Arg
465                 470                 475                 480

Gly Lys Arg Ala Thr Thr Val Thr Gly Thr Pro Cys Gln Asp Trp Ala
                485                 490                 495

Ala Gln Glu Pro His Arg His Ser Ile Phe Thr Pro Glu Thr Asn Pro
            500                 505                 510

Arg Ala Gly Leu Glu Lys Asn Tyr Cys Arg Asn Pro Asp Gly Asp Val
        515                 520                 525

Gly Gly Pro Trp Cys Tyr Thr Thr Asn Pro Arg Lys Leu Tyr Asp Tyr
    530                 535                 540

Cys Asp Val Pro Gln Cys Ala Ser Pro Ser Phe Asp Cys Gly Lys Pro
545                 550                 555                 560

Gln Val Glu Pro Lys Lys Cys Pro Gly Arg Val Val Gly Gly Cys Val
                565                 570                 575

Ala His Pro His Ser Trp Pro Trp Gln Val Ser Leu Arg Thr Arg Leu
            580                 585                 590

Gly Met His Phe Cys Gly Gly Thr Leu Ile Ser Pro Glu Trp Val Leu
        595                 600                 605

Thr Ala Ala His Cys Leu Glu Lys Ser Pro Arg Pro Ser Ser Tyr Lys
    610                 615                 620

Val Ile Leu Gly Ala His Gln Glu Val Lys Leu Glu Pro His Val Gln
625                 630                 635                 640

Glu Ile Glu Val Ser Arg Leu Phe Leu Glu Pro Thr Arg Thr Asp Ile
                645                 650                 655

Ala Leu Leu Lys Leu Ser Ser Pro Ala Ile Ile Thr Asp Lys Val Ile
            660                 665                 670

Pro Ala Cys Leu Pro Ser Pro Asn Tyr Val Val Ala Asp Arg Thr Glu
        675                 680                 685

Cys Phe Ile Thr Gly Trp Gly Glu Thr Gln Gly Thr Phe Gly Ala Gly
    690                 695                 700

Leu Leu Lys Glu Ala Gln Leu Pro Val Ile Glu Asn Lys Val Cys Asn
705                 710                 715                 720
```

```
Arg Asn Glu Phe Leu Asn Gly Arg Val Lys Ser Thr Glu Leu Cys Ala
                725                 730                 735

Gly His Leu Ala Gly Gly Thr Asp Ser Cys Gln Gly Asp Ser Gly Gly
            740                 745                 750

Pro Leu Val Cys Phe Glu Lys Asp Lys Tyr Ile Leu Gln Gly Val Thr
        755                 760                 765

Ser Trp Gly Leu Gly Cys Ala Arg Pro Asn Lys Pro Gly Val Tyr Val
    770                 775                 780

Arg Val Ser Arg Phe Val Thr Trp Ile Glu Gly Val Met Arg Asn Asn
785                 790                 795                 800

<210> SEQ ID NO 6
<211> LENGTH: 810
<212> TYPE: PRT
<213> ORGANISM: Macaca mulatta

<400> SEQUENCE: 6

Met Glu His Lys Glu Val Val Leu Leu Leu Leu Phe Leu Lys Ser
1               5                   10                  15

Gly Gln Gly Glu Pro Leu Asp Asp Tyr Val Asn Thr Lys Gly Ala Ser
                20                  25                  30

Leu Phe Ser Ile Thr Lys Lys Gln Leu Gly Ala Gly Ser Ile Glu Glu
            35                  40                  45

Cys Ala Lys Cys Glu Glu Glu Glu Phe Thr Cys Arg Ser Phe
50                  55                  60

Gln Tyr His Ser Lys Glu Gln Gln Cys Val Ile Met Ala Glu Asn Arg
65                  70                  75                  80

Lys Ser Ser Ile Val Phe Arg Met Arg Asp Val Val Leu Phe Glu Lys
                85                  90                  95

Lys Val Tyr Leu Ser Glu Cys Lys Thr Gly Asn Gly Lys Asn Tyr Arg
            100                 105                 110

Gly Thr Met Ser Lys Thr Arg Thr Gly Ile Thr Cys Gln Lys Trp Ser
        115                 120                 125

Ser Thr Ser Pro His Arg Pro Thr Phe Ser Pro Ala Thr His Pro Ser
130                 135                 140

Glu Gly Leu Glu Glu Asn Tyr Cys Arg Asn Pro Asp Asn Asp Gly Gln
145                 150                 155                 160

Gly Pro Trp Cys Tyr Thr Thr Asp Pro Glu Glu Arg Phe Asp Tyr Cys
                165                 170                 175

Asp Ile Pro Glu Cys Glu Asp Glu Cys Met His Cys Ser Gly Glu Asn
            180                 185                 190

Tyr Asp Gly Lys Ile Ser Lys Thr Met Ser Gly Leu Glu Cys Gln Ala
        195                 200                 205

Trp Asp Ser Gln Ser Pro His Ala His Gly Tyr Ile Pro Ser Lys Phe
210                 215                 220

Pro Asn Lys Asn Leu Lys Lys Asn Tyr Cys Arg Asn Pro Asp Gly Glu
225                 230                 235                 240

Pro Arg Pro Trp Cys Phe Thr Thr Asp Pro Asn Lys Arg Trp Glu Leu
                245                 250                 255

Cys Asp Ile Pro Arg Cys Thr Thr Pro Pro Ser Ser Gly Pro Thr
            260                 265                 270

Tyr Gln Cys Leu Lys Gly Thr Gly Glu Asn Tyr Arg Gly Asp Val Ala
        275                 280                 285

Val Thr Val Ser Gly His Thr Cys His Gly Trp Ser Ala Gln Thr Pro
290                 295                 300
```

```
His Thr His Asn Arg Thr Pro Glu Asn Phe Pro Cys Lys Asn Leu Asp
305                 310                 315                 320

Glu Asn Tyr Cys Arg Asn Pro Asp Gly Glu Lys Ala Pro Trp Cys Tyr
            325                 330                 335

Thr Thr Asn Ser Gln Val Arg Trp Glu Tyr Cys Lys Ile Pro Ser Cys
        340                 345                 350

Glu Ser Ser Pro Val Ser Thr Glu Pro Leu Asp Pro Thr Ala Pro Pro
            355                 360                 365

Glu Leu Thr Pro Val Val Gln Glu Cys Tyr His Gly Asp Gly Gln Ser
    370                 375                 380

Tyr Arg Gly Thr Ser Ser Thr Thr Thr Thr Gly Lys Lys Cys Gln Ser
385                 390                 395                 400

Trp Ser Ser Met Thr Pro His Trp His Glu Lys Thr Pro Glu Asn Phe
                405                 410                 415

Pro Asn Ala Gly Leu Thr Met Asn Tyr Cys Arg Asn Pro Asp Ala Asp
            420                 425                 430

Lys Gly Pro Trp Cys Phe Thr Thr Asp Pro Ser Val Arg Trp Glu Tyr
        435                 440                 445

Cys Asn Leu Lys Lys Cys Ser Gly Thr Glu Gly Ser Val Ala Ala Pro
    450                 455                 460

Pro Pro Val Ala Gln Leu Pro Asp Ala Glu Thr Pro Ser Glu Glu Asp
465                 470                 475                 480

Cys Met Phe Gly Asn Gly Lys Gly Tyr Arg Gly Lys Lys Ala Thr Thr
                485                 490                 495

Val Thr Gly Thr Pro Cys Gln Glu Trp Ala Ala Gln Glu Pro His Ser
            500                 505                 510

His Arg Ile Phe Thr Pro Glu Thr Asn Pro Arg Ala Gly Leu Glu Lys
        515                 520                 525

Asn Tyr Cys Arg Asn Pro Asp Gly Asp Val Gly Gly Pro Trp Cys Tyr
    530                 535                 540

Thr Thr Asn Pro Arg Lys Leu Phe Asp Tyr Cys Asp Val Pro Gln Cys
545                 550                 555                 560

Ala Ala Ser Ser Phe Asp Cys Gly Lys Pro Gln Val Glu Pro Lys Lys
                565                 570                 575

Cys Pro Gly Arg Val Val Gly Gly Cys Val Ala Tyr Pro His Ser Trp
            580                 585                 590

Pro Trp Gln Ile Ser Leu Arg Thr Arg Leu Gly Met His Phe Cys Gly
        595                 600                 605

Gly Thr Leu Ile Ser Pro Glu Trp Val Leu Thr Ala Ala His Cys Leu
    610                 615                 620

Glu Lys Ser Ser Arg Pro Ser Phe Tyr Lys Val Ile Leu Gly Ala His
625                 630                 635                 640

Arg Glu Val His Leu Glu Pro His Val Gln Glu Ile Glu Val Ser Lys
                645                 650                 655

Met Phe Ser Glu Pro Ala Arg Ala Asp Ile Ala Leu Leu Lys Leu Ser
            660                 665                 670

Ser Pro Ala Ile Ile Thr Asp Lys Val Ile Pro Ala Cys Leu Pro Ser
        675                 680                 685

Pro Asn Tyr Val Val Ala Asp Arg Thr Glu Cys Phe Ile Thr Gly Trp
    690                 695                 700

Gly Glu Thr Gln Gly Thr Tyr Gly Ala Gly Leu Leu Lys Glu Ala Arg
705                 710                 715                 720
```

-continued

Leu Pro Val Ile Glu Asn Lys Val Cys Asn Arg Tyr Glu Phe Leu Asn
                725                 730                 735

Gly Thr Val Lys Thr Thr Glu Leu Cys Ala Gly His Leu Ala Gly Gly
            740                 745                 750

Thr Asp Ser Cys Gln Gly Asp Ser Gly Gly Pro Leu Val Cys Phe Glu
        755                 760                 765

Lys Asp Lys Tyr Ile Leu Gln Gly Val Thr Ser Trp Gly Leu Gly Cys
    770                 775                 780

Ala Arg Pro Asn Lys Pro Gly Val Tyr Val Arg Val Ser Arg Phe Val
785                 790                 795                 800

Thr Trp Ile Glu Gly Val Met Arg Asn Asn
                805                 810

<210> SEQ ID NO 7
<211> LENGTH: 810
<212> TYPE: PRT
<213> ORGANISM: Pongo abelii

<400> SEQUENCE: 7

Met Glu His Lys Glu Val Val Leu Leu Leu Leu Phe Leu Lys Ser
1               5                   10                  15

Gly Gln Gly Glu Pro Leu Asp Asp Tyr Val Asn Thr Gln Gly Ala Ser
            20                  25                  30

Leu Phe Ser Val Thr Lys Lys Gln Leu Arg Ala Gly Ser Ile Glu Glu
        35                  40                  45

Cys Ala Ala Lys Cys Glu Glu Glu Lys Glu Phe Thr Cys Arg Ala Phe
    50                  55                  60

Gln Tyr His Ser Lys Glu Gln Gln Cys Val Ile Met Ala Glu Asn Arg
65                  70                  75                  80

Lys Ser Ser Ile Ile Ile Arg Met Arg Asp Val Val Leu Phe Glu Lys
                85                  90                  95

Lys Val Tyr Leu Ser Glu Cys Lys Thr Gly Asn Gly Lys Asn Tyr Arg
            100                 105                 110

Gly Thr Met Ser Lys Thr Lys Asn Gly Ile Thr Cys Gln Lys Trp Ser
        115                 120                 125

Ser Thr Ser Pro His Arg Pro Arg Phe Ser Pro Ala Thr His Pro Ser
    130                 135                 140

Glu Gly Leu Glu Glu Asn Tyr Cys Arg Asn Pro Asp Asn Asp Ala Gln
145                 150                 155                 160

Gly Pro Trp Cys Tyr Thr Thr Asp Pro Glu His Arg Tyr Asp Tyr Cys
                165                 170                 175

Asp Ile Pro Glu Cys Glu Glu Ala Cys Met His Cys Ser Gly Glu Asn
            180                 185                 190

Tyr Asp Gly Lys Ile Ser Lys Thr Met Ser Gly Leu Glu Cys Gln Ala
        195                 200                 205

Trp Asp Ser Gln Ser Pro His Ala His Gly Tyr Ile Pro Ser Lys Phe
    210                 215                 220

Pro Asn Lys Asn Leu Lys Lys Asn Tyr Cys Arg Asn Pro Asp Gly Glu
225                 230                 235                 240

Pro Arg Pro Trp Cys Phe Thr Thr Asp Pro Asn Lys Arg Trp Glu Leu
                245                 250                 255

Cys Asp Ile Pro Arg Cys Thr Thr Pro Pro Pro Ser Ser Gly Pro Thr
            260                 265                 270

Tyr Gln Cys Leu Lys Gly Thr Gly Glu Asn Tyr Arg Gly Asn Val Ala
        275                 280                 285

```
Val Thr Val Ser Gly His Thr Cys Gln Arg Trp Ser Ala Gln Thr Pro
    290                 295                 300

Gln Thr His Asn Arg Thr Pro Glu Asn Phe Pro Cys Lys Asn Leu Asp
305                 310                 315                 320

Glu Asn Tyr Cys Arg Asn Pro Asp Gly Glu Lys Ala Pro Trp Cys Tyr
                325                 330                 335

Thr Thr Asn Ser Gln Val Arg Trp Glu Tyr Cys Lys Ile Pro Ser Cys
            340                 345                 350

Gly Ser Ser Pro Val Ser Thr Glu Gln Leu Asp Pro Thr Ala Pro Pro
        355                 360                 365

Glu Leu Thr Pro Val Val Gln Asp Cys Tyr His Gly Asp Gly Gln Ser
370                 375                 380

Tyr Arg Gly Thr Ser Ser Thr Thr Thr Thr Gly Lys Lys Cys Gln Ser
385                 390                 395                 400

Trp Ser Ser Met Thr Pro His Trp His Gln Lys Thr Pro Glu Asn Tyr
                405                 410                 415

Pro Asp Ala Gly Leu Thr Met Asn Tyr Cys Arg Asn Pro Asp Ala Asp
            420                 425                 430

Lys Gly Pro Trp Cys Phe Thr Thr Asp Pro Ser Val Arg Trp Glu Tyr
        435                 440                 445

Cys Asn Leu Lys Lys Cys Ser Gly Thr Glu Gly Ser Val Val Ala Pro
450                 455                 460

Pro Pro Val Val Gln Leu Pro Asn Val Glu Thr Pro Ser Glu Glu Asp
465                 470                 475                 480

Cys Met Phe Gly Asn Gly Lys Gly Tyr Arg Gly Lys Arg Ala Thr Thr
                485                 490                 495

Val Thr Gly Thr Pro Cys Gln Glu Trp Ala Ala Gln Glu Pro His Arg
            500                 505                 510

His Ser Ile Phe Thr Pro Gln Thr Asn Pro Arg Ala Gly Leu Glu Lys
        515                 520                 525

Asn Tyr Cys Arg Asn Pro Asp Gly Asp Glu Gly Gly Pro Trp Cys Tyr
                530                 535                 540

Thr Thr Asn Pro Arg Lys His Tyr Asp Tyr Cys Asp Val Pro Gln Cys
545                 550                 555                 560

Ala Ser Ser Ser Phe Asp Cys Gly Lys Pro Gln Val Glu Pro Lys Lys
                565                 570                 575

Cys Pro Gly Arg Val Val Gly Gly Cys Val Ala Asn Ala His Ser Trp
            580                 585                 590

Pro Trp Gln Val Ser Leu Arg Thr Arg Phe Gly Thr His Phe Cys Gly
        595                 600                 605

Gly Thr Leu Ile Ser Pro Glu Trp Val Leu Thr Ala Ala His Cys Leu
610                 615                 620

Glu Lys Ser Pro Arg Pro Ser Ser Tyr Lys Val Ile Leu Gly Ala His
625                 630                 635                 640

Gln Glu Val Asn Leu Glu Pro His Val Gln Glu Ile Glu Val Ser Arg
                645                 650                 655

Leu Phe Leu Glu Pro Thr Arg Ala Asp Ile Ala Leu Leu Lys Leu Ser
            660                 665                 670

Ser Pro Ala Val Ile Thr Asp Lys Val Ile Pro Ala Cys Leu Pro Ser
        675                 680                 685

Pro Asn Tyr Val Val Ala Gly Arg Thr Glu Cys Phe Ile Thr Gly Trp
690                 695                 700
```

```
Gly Glu Thr Gln Gly Thr Phe Gly Ala Gly Leu Leu Lys Glu Ala Gln
705                 710                 715                 720

Leu Pro Val Ile Glu Asn Lys Val Cys Asn Arg Tyr Glu Phe Leu Asn
                725                 730                 735

Gly Arg Val Lys Ser Thr Glu Leu Cys Ala Gly His Leu Ala Gly Gly
            740                 745                 750

Thr Asp Ser Cys Gln Gly Asp Ser Gly Gly Pro Leu Val Cys Phe Glu
        755                 760                 765

Lys Asp Lys Tyr Ile Leu Gln Gly Val Thr Ser Trp Gly Leu Gly Cys
770                 775                 780

Ala Arg Pro Asn Lys Pro Gly Val Tyr Val Arg Val Ser Arg Phe Val
785                 790                 795                 800

Thr Trp Ile Glu Gly Val Met Arg Asn Asn
                805                 810

<210> SEQ ID NO 8
<211> LENGTH: 809
<212> TYPE: PRT
<213> ORGANISM: Sus scrofa

<400> SEQUENCE: 8

Met Asp His Lys Glu Val Val Leu Leu Leu Leu Phe Leu Lys Ser
1               5                   10                  15

Gly Leu Gly Asp Ser Leu Asp Asp Tyr Val Asn Thr Gln Gly Ala Phe
            20                  25                  30

Leu Phe Ser Leu Ser Arg Lys Gln Val Ala Ala Arg Ser Val Glu Glu
        35                  40                  45

Cys Ala Ala Lys Cys Glu Ala Glu Thr Asn Phe Ile Cys Arg Ala Phe
    50                  55                  60

Gln Tyr His Ser Lys Asp Gln Gln Cys Val Val Met Ala Glu Asn Ser
65                  70                  75                  80

Lys Thr Ser Pro Ile Ala Arg Met Arg Asp Val Val Leu Phe Glu Lys
                85                  90                  95

Arg Ile Tyr Leu Ser Glu Cys Lys Thr Gly Asn Gly Lys Asn Tyr Arg
            100                 105                 110

Gly Thr Thr Ser Lys Thr Lys Ser Gly Val Ile Cys Gln Lys Trp Ser
        115                 120                 125

Val Ser Ser Pro His Ile Pro Lys Tyr Ser Pro Glu Lys Phe Pro Leu
    130                 135                 140

Ala Gly Leu Glu Glu Asn Tyr Cys Arg Asn Pro Asp Asn Asp Glu Lys
145                 150                 155                 160

Gly Pro Trp Cys Tyr Thr Thr Asp Pro Glu Thr Arg Phe Asp Tyr Cys
                165                 170                 175

Asp Ile Pro Glu Cys Glu Asp Glu Cys Met His Cys Ser Gly Glu His
            180                 185                 190

Tyr Glu Gly Lys Ile Ser Lys Thr Met Ser Gly Ile Glu Cys Gln Ser
        195                 200                 205

Trp Gly Ser Gln Ser Pro His Ala His Gly Tyr Leu Pro Ser Lys Phe
    210                 215                 220

Pro Asn Lys Asn Leu Lys Met Asn Tyr Cys Arg Asn Pro Asp Gly Glu
225                 230                 235                 240

Pro Arg Pro Trp Cys Phe Thr Thr Asp Pro Asn Lys Arg Trp Glu Phe
                245                 250                 255

Cys Asp Ile Pro Arg Cys Thr Thr Pro Pro Pro Thr Ser Gly Pro Thr
            260                 265                 270
```

```
Tyr Gln Cys Leu Lys Gly Arg Gly Glu Asn Tyr Arg Gly Thr Val Ser
        275                 280                 285

Val Thr Ala Ser Gly His Thr Cys Gln Arg Trp Ser Ala Gln Ser Pro
290                 295                 300

His Lys His Asn Arg Thr Pro Glu Asn Phe Pro Cys Lys Asn Leu Glu
305                 310                 315                 320

Glu Asn Tyr Cys Arg Asn Pro Asp Gly Glu Thr Ala Pro Trp Cys Tyr
                325                 330                 335

Thr Thr Asp Ser Glu Val Arg Trp Asp Tyr Cys Lys Ile Pro Ser Cys
            340                 345                 350

Gly Ser Ser Thr Ser Thr Glu Tyr Leu Asp Ala Pro Val Pro Pro
                355                 360                 365

Glu Gln Thr Pro Val Ala Gln Asp Cys Tyr Arg Gly Asn Gly Glu Ser
        370                 375                 380

Tyr Arg Gly Thr Ser Ser Thr Thr Ile Thr Gly Arg Lys Cys Gln Ser
385                 390                 395                 400

Trp Val Ser Met Thr Pro His Arg His Glu Lys Thr Pro Gly Asn Phe
                405                 410                 415

Pro Asn Ala Gly Leu Thr Met Asn Tyr Cys Arg Asn Pro Asp Ala Asp
                420                 425                 430

Lys Ser Pro Trp Cys Tyr Thr Thr Asp Pro Arg Val Arg Trp Glu Tyr
            435                 440                 445

Cys Asn Leu Lys Lys Cys Ser Glu Thr Glu Gln Gln Val Thr Asn Phe
        450                 455                 460

Pro Ala Ile Ala Gln Val Pro Ser Val Glu Asp Leu Ser Glu Asp Cys
465                 470                 475                 480

Met Phe Gly Asn Gly Lys Arg Tyr Arg Gly Lys Arg Ala Thr Thr Val
                485                 490                 495

Ala Gly Val Pro Cys Gln Glu Trp Ala Ala Gln Glu Pro His Arg His
                500                 505                 510

Ser Ile Phe Thr Pro Glu Thr Asn Pro Arg Ala Gly Leu Glu Lys Asn
        515                 520                 525

Tyr Cys Arg Asn Pro Asp Gly Asp Asn Gly Pro Trp Cys Tyr Thr
        530                 535                 540

Thr Asn Pro Gln Lys Leu Phe Asp Tyr Cys Asp Val Pro Gln Cys Val
545                 550                 555                 560

Thr Ser Ser Phe Asp Cys Gly Lys Pro Lys Val Glu Pro Lys Lys Cys
                565                 570                 575

Pro Ala Arg Val Val Gly Gly Cys Val Ser Ile Pro His Ser Trp Pro
                580                 585                 590

Trp Gln Ile Ser Leu Arg His Arg Tyr Gly Gly His Phe Cys Gly Gly
        595                 600                 605

Thr Leu Ile Ser Pro Glu Trp Val Leu Thr Ala Lys His Cys Leu Glu
        610                 615                 620

Lys Ser Ser Ser Pro Ser Ser Tyr Lys Val Ile Leu Gly Ala His Glu
625                 630                 635                 640

Glu Tyr His Leu Gly Glu Gly Val Gln Glu Ile Asp Val Ser Lys Leu
                645                 650                 655

Phe Lys Glu Pro Ser Glu Ala Asp Ile Ala Leu Leu Lys Leu Ser Ser
                660                 665                 670

Pro Ala Ile Ile Thr Asp Lys Val Ile Pro Ala Cys Leu Pro Thr Pro
                675                 680                 685
```

```
Asn Tyr Val Val Ala Asp Arg Thr Ala Cys Tyr Ile Thr Gly Trp Gly
    690                 695                 700
Glu Thr Lys Gly Thr Tyr Gly Ala Gly Leu Leu Lys Glu Ala Arg Leu
705                 710                 715                 720
Pro Val Ile Glu Asn Lys Val Cys Asn Arg Tyr Glu Tyr Leu Gly Gly
                725                 730                 735
Lys Val Ser Pro Asn Glu Leu Cys Ala Gly His Leu Ala Gly Gly Ile
            740                 745                 750
Asp Ser Cys Gln Gly Asp Ser Gly Gly Pro Leu Val Cys Phe Glu Lys
        755                 760                 765
Asp Lys Tyr Ile Leu Gln Gly Val Thr Ser Trp Gly Leu Gly Cys Ala
770                 775                 780
Leu Pro Asn Lys Pro Gly Val Tyr Val Arg Val Ser Arg Phe Val Thr
785                 790                 795                 800
Trp Ile Glu Glu Ile Met Arg Arg Asn
                805

<210> SEQ ID NO 9
<211> LENGTH: 812
<212> TYPE: PRT
<213> ORGANISM: Bos Taurus

<400> SEQUENCE: 9

Met Leu Pro Ala Ser Pro Lys Met Glu His Lys Ala Val Val Phe Leu
1               5                   10                  15
Ile Leu Leu Phe Leu Lys Ser Gly Leu Gly Asp Leu Leu Asp Asp Tyr
            20                  25                  30
Val Asn Thr Gln Gly Ala Ser Leu Leu Ser Leu Ser Arg Lys Asn Leu
        35                  40                  45
Ala Gly Arg Ser Val Glu Asp Cys Ala Ala Lys Cys Glu Glu Glu Thr
    50                  55                  60
Asp Phe Val Cys Arg Ala Phe Gln Tyr His Ser Lys Glu Gln Gln Cys
65                  70                  75                  80
Val Val Met Ala Glu Asn Ser Lys Asn Thr Pro Val Phe Arg Met Arg
                85                  90                  95
Asp Val Ile Leu Tyr Glu Lys Arg Ile Tyr Leu Leu Glu Cys Lys Thr
            100                 105                 110
Gly Asn Gly Gln Thr Tyr Arg Gly Thr Thr Ala Glu Thr Lys Ser Gly
        115                 120                 125
Val Thr Cys Gln Lys Trp Ser Ala Thr Ser Pro His Val Pro Lys Phe
    130                 135                 140
Ser Pro Glu Lys Phe Pro Leu Ala Gly Leu Glu Glu Asn Tyr Cys Arg
145                 150                 155                 160
Asn Pro Asp Asn Asp Glu Asn Gly Pro Trp Cys Tyr Thr Thr Asp Pro
                165                 170                 175
Asp Lys Arg Tyr Asp Tyr Cys Asp Ile Pro Glu Cys Glu Asp Lys Cys
            180                 185                 190
Met His Cys Ser Gly Glu Asn Tyr Glu Gly Lys Ile Ala Lys Thr Met
        195                 200                 205
Ser Gly Arg Asp Cys Gln Ala Trp Asp Ser Gln Ser Pro His Ala His
    210                 215                 220
Gly Tyr Ile Pro Ser Lys Phe Pro Ser Lys Asn Leu Lys Met Asn Tyr
225                 230                 235                 240
Cys Arg Asn Pro Asp Gly Glu Pro Arg Pro Trp Cys Phe Thr Thr Asp
                245                 250                 255
```

-continued

```
Pro Gln Lys Arg Trp Glu Phe Cys Asp Ile Pro Arg Cys Thr Thr Pro
            260                 265                 270
Pro Pro Ser Ser Gly Pro Lys Tyr Gln Cys Leu Lys Gly Thr Gly Lys
        275                 280                 285
Asn Tyr Gly Gly Thr Val Ala Val Thr Glu Ser Gly His Thr Cys Gln
    290                 295                 300
Arg Trp Ser Glu Gln Thr Pro His Lys His Asn Arg Thr Pro Glu Asn
305                 310                 315                 320
Phe Pro Cys Lys Asn Leu Glu Glu Asn Tyr Cys Arg Asn Pro Asn Gly
                325                 330                 335
Glu Lys Ala Pro Trp Cys Tyr Thr Thr Asn Ser Lys Val Arg Trp Glu
            340                 345                 350
Tyr Cys Thr Ile Pro Ser Cys Glu Ser Ser Pro Leu Ser Thr Glu Arg
        355                 360                 365
Met Asp Val Pro Val Pro Pro Glu Gln Thr Pro Val Pro Gln Asp Cys
    370                 375                 380
Tyr His Gly Asn Gly Gln Ser Tyr Arg Gly Thr Ser Ser Thr Thr Ile
385                 390                 395                 400
Thr Gly Arg Lys Cys Gln Ser Trp Ser Ser Met Thr Pro His Arg His
                405                 410                 415
Leu Lys Thr Pro Glu Asn Tyr Pro Asn Ala Gly Leu Thr Met Asn Tyr
            420                 425                 430
Cys Arg Asn Pro Asp Ala Asp Lys Ser Pro Trp Cys Tyr Thr Thr Asp
        435                 440                 445
Pro Arg Val Arg Trp Glu Phe Cys Asn Leu Lys Lys Cys Ser Glu Thr
    450                 455                 460
Pro Glu Gln Val Pro Ala Ala Pro Gln Ala Pro Gly Val Glu Asn Pro
465                 470                 475                 480
Pro Glu Ala Asp Cys Met Ile Gly Met Gly Lys Ser Tyr Arg Gly Lys
                485                 490                 495
Lys Ala Thr Thr Val Ala Gly Val Pro Cys Gln Glu Trp Ala Ala Gln
            500                 505                 510
Glu Pro His His His Ser Ile Phe Thr Pro Glu Thr Asn Pro Gln Ser
        515                 520                 525
Gly Leu Glu Arg Asn Tyr Cys Arg Asn Pro Asp Gly Asp Val Asn Gly
    530                 535                 540
Pro Trp Cys Tyr Thr Met Asn Pro Arg Lys Leu Phe Asp Tyr Cys Asp
545                 550                 555                 560
Val Pro Gln Cys Glu Ser Ser Phe Asp Cys Gly Lys Pro Lys Val Glu
                565                 570                 575
Pro Lys Lys Cys Ser Gly Arg Ile Val Gly Gly Cys Val Ser Lys Pro
            580                 585                 590
His Ser Trp Pro Trp Gln Val Ser Leu Arg Arg Ser Ser Arg His Phe
        595                 600                 605
Cys Gly Gly Thr Leu Ile Ser Pro Lys Trp Val Leu Thr Ala Ala His
    610                 615                 620
Cys Leu Asp Asn Ile Leu Ala Leu Ser Phe Tyr Lys Val Ile Leu Gly
625                 630                 635                 640
Ala His Asn Glu Lys Val Arg Glu Gln Ser Val Gln Glu Ile Pro Val
                645                 650                 655
Ser Arg Leu Phe Arg Glu Pro Ser Gln Ala Asp Ile Ala Leu Leu Lys
            660                 665                 670
```

```
Leu Ser Arg Pro Ala Ile Ile Thr Lys Glu Val Ile Pro Ala Cys Leu
            675                 680                 685

Pro Pro Pro Asn Tyr Met Val Ala Ala Arg Thr Glu Cys Tyr Ile Thr
        690                 695                 700

Gly Trp Gly Glu Thr Gln Gly Thr Phe Gly Glu Gly Leu Leu Lys Glu
705                 710                 715                 720

Ala His Leu Pro Val Ile Glu Asn Lys Val Cys Asn Arg Asn Glu Tyr
                725                 730                 735

Leu Asp Gly Arg Val Lys Pro Thr Glu Leu Cys Ala Gly His Leu Ile
            740                 745                 750

Gly Gly Thr Asp Ser Cys Gln Gly Asp Ser Gly Gly Pro Leu Val Cys
        755                 760                 765

Phe Glu Lys Asp Lys Tyr Ile Leu Gln Gly Val Thr Ser Trp Gly Leu
770                 775                 780

Gly Cys Ala Arg Pro Asn Lys Pro Gly Val Tyr Val Arg Val Ser Pro
785                 790                 795                 800

Tyr Val Pro Trp Ile Glu Glu Thr Met Arg Arg Asn
                805                 810

<210> SEQ ID NO 10
<211> LENGTH: 811
<212> TYPE: PRT
<213> ORGANISM: Equus caballus

<400> SEQUENCE: 10

Met Glu His Gln Glu Val Val Phe Leu Leu Leu Leu Phe Leu Lys Ser
1               5                   10                  15

Gly His Gly Asp Ile Leu Asp Asp Tyr Val Thr Thr Gln Gly Ala Ser
            20                  25                  30

Leu Phe Thr Phe Thr Arg Lys Pro Leu Ser Ala Ser Ser Ile Glu Glu
        35                  40                  45

Cys Glu Ala Lys Cys Thr Glu Glu Thr Ala Phe Ile Cys Arg Ala Phe
    50                  55                  60

Gln Tyr His Ser Lys Glu Pro Arg Cys Val Leu Leu Ala Glu Asn Arg
65                  70                  75                  80

Lys Ser Ser Pro Val Met Arg Met Arg Asp Val Ile Leu Phe Glu Lys
                85                  90                  95

Arg Ile Tyr Leu Ser Glu Cys Lys Thr Gly Thr Gly Arg Ser Tyr Arg
            100                 105                 110

Gly Thr Thr Ser Lys Thr Lys Asn Gly Val Ser Cys Gln Lys Trp Ser
        115                 120                 125

Asp Thr Ser Pro His Ile Pro Lys Tyr Ser Pro Asp Lys Asn Pro Ser
    130                 135                 140

Glu Gly Leu Glu Glu Asn Tyr Cys Arg Asn Pro Asp Asn Asp Glu Lys
145                 150                 155                 160

Gly Pro Trp Cys Tyr Thr Thr Asp Pro Gly Thr Arg Phe Asp Tyr Cys
                165                 170                 175

Asp Ile Pro Glu Cys Glu Asp Glu Cys Met His Cys Ser Gly Glu Asn
            180                 185                 190

Tyr Glu Gly Lys Ile Ser Lys Thr Ile Ser Gly Leu Glu Cys Gln Pro
        195                 200                 205

Trp Ala Ser Gln Ser Pro His Ala His Gly Tyr Ile Pro Ser Lys Phe
    210                 215                 220

Pro Asn Lys Asn Leu Arg Met Asn Tyr Cys Arg Asn Pro Asp Gly Glu
225                 230                 235                 240
```

```
Pro Arg Pro Trp Cys Phe Thr Met Asp Pro Asp Lys Arg Trp Glu Phe
            245                 250                 255

Cys Asp Ile Pro Arg Cys Ser Thr Pro Pro Ser Ser Gly Pro Thr
        260                 265                 270

Tyr Gln Cys Leu Lys Gly Arg Gly Glu Asn Tyr Arg Gly Arg Val Ser
        275                 280                 285

Val Thr Gln Ser Gly Leu Thr Cys Gln Arg Trp Ser Glu Gln Thr Pro
    290                 295                 300

His Lys His Asn Arg Thr Pro Asp Asn Phe Pro Cys Lys Asn Leu Asp
305                 310                 315                 320

Glu Asn Tyr Cys Arg Asn Pro Asp Gly Glu Thr Ala Pro Trp Cys Tyr
                325                 330                 335

Thr Thr Ser Ser Glu Thr Arg Trp Glu Tyr Cys Asn Ile Pro Ser Cys
            340                 345                 350

Thr Ser Ser Ser Val Pro Thr Glu Ile Thr Asp Ala Ser Glu Pro Pro
        355                 360                 365

Glu Gln Thr Pro Val Val Gln Asp Cys Tyr Gln Asp Lys Gly Glu Ser
    370                 375                 380

Tyr Arg Gly Thr Ser Ser Ile Thr Val Thr Gly Lys Lys Cys Gln Ser
385                 390                 395                 400

Trp Ser Ser Met Thr Pro His Trp His Gln Lys Thr Pro Glu Lys Tyr
                405                 410                 415

Pro Asn Ala Asp Leu Thr Met Asn Tyr Cys Arg Asn Pro Asp Gly Asp
            420                 425                 430

Lys Gly Pro Trp Cys Tyr Thr Thr Asp Pro Ser Val Arg Trp Glu Phe
        435                 440                 445

Cys Asn Leu Arg Arg Cys Ser Glu Thr Gln Gln Ser Phe Ser Asn Ser
450                 455                 460

Ser Pro Thr Asp Thr Gln Val Pro Ser Val Gln Glu Pro Ser Glu Pro
465                 470                 475                 480

Asp Cys Met Leu Gly Ile Gly Lys Gly Tyr Gln Gly Lys Lys Ala Thr
                485                 490                 495

Thr Val Thr Gly Thr Arg Cys Gln Ala Trp Ala Ala Gln Glu Pro His
            500                 505                 510

Arg His Ser Ile Phe Thr Pro Glu Ala Asn Pro Trp Ala Asn Leu Glu
        515                 520                 525

Lys Asn Tyr Cys Arg Asn Pro Asp Gly Asp Val Asn Gly Pro Trp Cys
530                 535                 540

Tyr Thr Met Asn Pro Gln Lys Leu Phe Asp Tyr Cys Asp Val Pro Gln
545                 550                 555                 560

Cys Glu Ser Ser Pro Phe Asp Cys Gly Lys Pro Lys Val Glu Pro Lys
                565                 570                 575

Lys Cys Ser Gly Arg Ile Val Gly Gly Cys Val Ala Ile Ala His Ser
            580                 585                 590

Trp Pro Trp Gln Ile Ser Leu Arg Thr Arg Phe Gly His Phe Cys
        595                 600                 605

Gly Gly Thr Leu Ile Ser Pro Glu Trp Val Leu Thr Ala Ala His Cys
    610                 615                 620

Leu Glu Arg Ser Ser Arg Pro Ser Thr Tyr Lys Val Val Leu Gly Thr
625                 630                 635                 640

His His Glu Leu Arg Leu Ala Ala Gly Ala Gln Gln Ile Asp Val Ser
                645                 650                 655
```

```
Lys Leu Phe Leu Glu Pro Ser Arg Ala Asp Ile Ala Leu Leu Lys Leu
                660                 665                 670

Ser Ser Pro Ala Ile Ile Thr Gln Asn Val Ile Pro Ala Cys Leu Pro
            675                 680                 685

Pro Ala Asp Tyr Val Ala Asn Trp Ala Glu Cys Phe Val Thr Gly
        690                 695                 700

Trp Gly Glu Thr Gln Asp Ser Ser Asn Ala Gly Val Leu Lys Glu Ala
705                 710                 715                 720

Gln Leu Pro Val Ile Glu Asn Lys Val Cys Asn Arg Tyr Glu Tyr Leu
                725                 730                 735

Asn Gly Arg Val Lys Ser Thr Glu Leu Cys Ala Gly His Leu Val Gly
            740                 745                 750

Gly Val Asp Ser Cys Gln Gly Asp Ser Gly Gly Pro Leu Val Cys Phe
        755                 760                 765

Glu Lys Asp Lys Tyr Ile Leu Gln Gly Val Thr Ser Trp Gly Leu Gly
770                 775                 780

Cys Ala Arg Pro Asn Lys Pro Gly Val Tyr Val Arg Val Ser Ser Phe
785                 790                 795                 800

Ile Asn Trp Ile Glu Arg Ile Met Gln Ser Asn
                805                 810

<210> SEQ ID NO 11
<211> LENGTH: 812
<212> TYPE: PRT
<213> ORGANISM: Mus musculus

<400> SEQUENCE: 11

Met Asp His Lys Glu Val Ile Leu Leu Phe Leu Leu Leu Lys Pro
1               5                   10                  15

Gly Gln Gly Asp Ser Leu Asp Gly Tyr Ile Ser Thr Gln Gly Ala Ser
                20                  25                  30

Leu Phe Ser Leu Thr Lys Lys Gln Leu Ala Ala Gly Gly Val Ala Asp
            35                  40                  45

Cys Leu Ala Lys Cys Glu Gly Glu Thr Asp Phe Val Cys Arg Ser Phe
        50                  55                  60

Gln Tyr His Ser Lys Glu Gln Gln Cys Val Ile Met Ala Glu Asn Ser
65                  70                  75                  80

Lys Thr Ser Ser Ile Ile Arg Met Arg Asp Val Ile Leu Phe Glu Lys
                85                  90                  95

Arg Val Tyr Leu Ser Glu Cys Lys Thr Gly Ile Gly Asn Ser Tyr Arg
                100                 105                 110

Gly Thr Met Ser Arg Thr Lys Ser Gly Val Ala Cys Gln Lys Trp Gly
            115                 120                 125

Ala Thr Phe Pro His Val Pro Asn Tyr Ser Pro Ser Thr His Pro Asn
        130                 135                 140

Glu Gly Leu Glu Glu Asn Tyr Cys Arg Asn Pro Asp Asn Asp Glu Gln
145                 150                 155                 160

Gly Pro Trp Cys Tyr Thr Thr Asp Pro Asp Lys Arg Tyr Asp Tyr Cys
                165                 170                 175

Asn Ile Pro Glu Cys Glu Glu Cys Met Tyr Cys Ser Gly Glu Lys
                180                 185                 190

Tyr Glu Gly Lys Ile Ser Lys Thr Met Ser Gly Leu Asp Cys Gln Ala
            195                 200                 205

Trp Asp Ser Gln Ser Pro His Ala His Gly Tyr Ile Pro Ala Lys Phe
        210                 215                 220
```

```
Pro Ser Lys Asn Leu Lys Met Asn Tyr Cys Arg Asn Pro Asp Gly Glu
225                 230                 235                 240

Pro Arg Pro Trp Cys Phe Thr Thr Asp Pro Thr Lys Arg Trp Glu Tyr
            245                 250                 255

Cys Asp Ile Pro Arg Cys Thr Thr Pro Pro Pro Pro Ser Pro Thr
        260                 265                 270

Tyr Gln Cys Leu Lys Gly Arg Gly Glu Asn Tyr Arg Gly Thr Val Ser
        275                 280                 285

Val Thr Val Ser Gly Lys Thr Cys Gln Arg Trp Ser Glu Gln Thr Pro
    290                 295                 300

His Arg His Asn Arg Thr Pro Glu Asn Phe Pro Cys Lys Asn Leu Glu
305                 310                 315                 320

Glu Asn Tyr Cys Arg Asn Pro Asp Gly Glu Thr Ala Pro Trp Cys Tyr
                325                 330                 335

Thr Thr Asp Ser Gln Leu Arg Trp Glu Tyr Cys Glu Ile Pro Ser Cys
            340                 345                 350

Glu Ser Ser Ala Ser Pro Asp Gln Ser Asp Ser Ser Val Pro Pro Glu
            355                 360                 365

Glu Gln Thr Pro Val Val Gln Glu Cys Tyr Gln Ser Asp Gly Gln Ser
370                 375                 380

Tyr Arg Gly Thr Ser Ser Thr Thr Ile Thr Gly Lys Lys Cys Gln Ser
385                 390                 395                 400

Trp Ala Ala Met Phe Pro His Arg His Ser Lys Thr Pro Glu Asn Phe
                405                 410                 415

Pro Asp Ala Gly Leu Glu Met Asn Tyr Cys Arg Asn Pro Asp Gly Asp
            420                 425                 430

Lys Gly Pro Trp Cys Tyr Thr Thr Asp Pro Ser Val Arg Trp Glu Tyr
            435                 440                 445

Cys Asn Leu Lys Arg Cys Ser Glu Thr Gly Gly Ser Val Val Glu Leu
        450                 455                 460

Pro Thr Val Ser Gln Glu Pro Ser Gly Pro Ser Asp Ser Glu Thr Asp
465                 470                 475                 480

Cys Met Tyr Gly Asn Gly Lys Asp Tyr Arg Gly Lys Thr Ala Val Thr
                485                 490                 495

Ala Ala Gly Thr Pro Cys Gln Gly Trp Ala Ala Gln Glu Pro His Arg
            500                 505                 510

His Ser Ile Phe Thr Pro Gln Thr Asn Pro Arg Ala Gly Leu Glu Lys
        515                 520                 525

Asn Tyr Cys Arg Asn Pro Asp Gly Asp Val Asn Gly Pro Trp Cys Tyr
    530                 535                 540

Thr Thr Asn Pro Arg Lys Leu Tyr Asp Tyr Cys Asp Ile Pro Leu Cys
545                 550                 555                 560

Ala Ser Ala Ser Ser Phe Glu Cys Gly Lys Pro Gln Val Glu Pro Lys
            565                 570                 575

Lys Cys Pro Gly Arg Val Val Gly Gly Cys Val Ala Asn Pro His Ser
            580                 585                 590

Trp Pro Trp Gln Ile Ser Leu Arg Thr Arg Phe Thr Gly Gln His Phe
            595                 600                 605

Cys Gly Gly Thr Leu Ile Ala Pro Glu Trp Val Leu Thr Ala Ala His
            610                 615                 620

Cys Leu Glu Lys Ser Ser Arg Pro Glu Phe Tyr Lys Val Ile Leu Gly
625                 630                 635                 640
```

```
Ala His Glu Glu Tyr Ile Arg Gly Ser Asp Val Gln Glu Ile Ser Val
                645                 650                 655

Ala Lys Leu Ile Leu Glu Pro Asn Asn Arg Asp Ile Ala Leu Leu Lys
            660                 665                 670

Leu Ser Arg Pro Ala Thr Ile Thr Asp Lys Val Ile Pro Ala Cys Leu
        675                 680                 685

Pro Ser Pro Asn Tyr Met Val Ala Asp Arg Thr Ile Cys Tyr Ile Thr
    690                 695                 700

Gly Trp Gly Glu Thr Gln Gly Thr Phe Gly Ala Gly Arg Leu Lys Glu
705                 710                 715                 720

Ala Gln Leu Pro Val Ile Glu Asn Lys Val Cys Asn Arg Val Glu Tyr
            725                 730                 735

Leu Asn Asn Arg Val Lys Ser Thr Glu Leu Cys Ala Gly Gln Leu Ala
        740                 745                 750

Gly Gly Val Asp Ser Cys Gln Gly Asp Ser Gly Gly Pro Leu Val Cys
    755                 760                 765

Phe Glu Lys Asp Lys Tyr Ile Leu Gln Gly Val Thr Ser Trp Gly Leu
770                 775                 780

Gly Cys Ala Arg Pro Asn Lys Pro Gly Val Tyr Val Arg Val Ser Arg
785                 790                 795                 800

Phe Val Asp Trp Ile Glu Arg Glu Met Arg Asn Asn
                805                 810

<210> SEQ ID NO 12
<211> LENGTH: 812
<212> TYPE: PRT
<213> ORGANISM: Rattus norvegicus

<400> SEQUENCE: 12

Met Asp His Lys Glu Ile Ile Leu Leu Phe Leu Leu Phe Leu Lys Pro
1               5                   10                  15

Gly Gln Gly Asp Ser Leu Asp Gly Tyr Val Ser Thr Gln Gly Ala Ser
            20                  25                  30

Leu His Ser Leu Thr Lys Lys Gln Leu Ala Ala Gly Ser Ile Ala Asp
        35                  40                  45

Cys Leu Ala Lys Cys Glu Gly Glu Thr Asp Phe Ile Cys Arg Ser Phe
    50                  55                  60

Gln Tyr His Ser Lys Glu Gln Gln Cys Val Ile Met Ala Glu Asn Ser
65                  70                  75                  80

Lys Thr Ser Ser Ile Ile Arg Met Arg Asp Val Ile Leu Phe Glu Lys
                85                  90                  95

Arg Val Tyr Leu Ser Glu Cys Lys Thr Gly Ile Gly Lys Gly Tyr Arg
            100                 105                 110

Gly Thr Met Ser Lys Thr Lys Thr Gly Val Thr Cys Gln Lys Trp Ser
        115                 120                 125

Asp Thr Ser Pro His Val Pro Lys Tyr Ser Pro Ser Thr His Pro Ser
    130                 135                 140

Glu Gly Leu Glu Glu Asn Tyr Cys Arg Asn Pro Asp Asn Asp Glu Gln
145                 150                 155                 160

Gly Pro Trp Cys Tyr Thr Thr Asp Pro Asp Gln Arg Tyr Glu Tyr Cys
                165                 170                 175

Asn Ile Pro Glu Cys Glu Glu Glu Cys Met Tyr Cys Ser Gly Glu Lys
            180                 185                 190

Tyr Glu Gly Lys Ile Ser Lys Thr Met Ser Gly Leu Asp Cys Gln Ser
        195                 200                 205
```

```
Trp Asp Ser Gln Ser Pro His Ala His Gly Tyr Ile Pro Ala Lys Phe
    210                 215                 220
Pro Ser Lys Asn Leu Lys Met Asn Tyr Cys Arg Asn Pro Asp Gly Glu
225                 230                 235                 240
Pro Arg Pro Trp Cys Phe Thr Thr Asp Pro Asn Lys Arg Trp Glu Tyr
                245                 250                 255
Cys Asp Ile Pro Arg Cys Thr Thr Pro Pro Pro Pro Gly Pro Thr
            260                 265                 270
Tyr Gln Cys Leu Lys Gly Arg Gly Glu Asn Tyr Arg Gly Thr Val Ser
        275                 280                 285
Val Thr Ala Ser Gly Lys Thr Cys Gln Arg Trp Ser Glu Gln Thr Pro
    290                 295                 300
His Arg His Asn Arg Thr Pro Glu Asn Phe Pro Cys Lys Asn Leu Glu
305                 310                 315                 320
Glu Asn Tyr Cys Arg Asn Pro Asp Gly Glu Thr Ala Pro Trp Cys Tyr
                325                 330                 335
Thr Thr Asp Ser Gln Leu Arg Trp Glu Tyr Cys Glu Ile Pro Ser Cys
            340                 345                 350
Gly Ser Ser Val Ser Pro Asp Gln Ser Asp Ser Ser Val Leu Pro Glu
        355                 360                 365
Gln Thr Pro Val Val Gln Glu Cys Tyr Gln Gly Asn Gly Lys Ser Tyr
    370                 375                 380
Arg Gly Thr Ser Ser Thr Thr Asn Thr Gly Lys Lys Cys Gln Ser Trp
385                 390                 395                 400
Val Ser Met Thr Pro His Ser His Ser Lys Thr Pro Ala Asn Phe Pro
                405                 410                 415
Asp Ala Gly Leu Glu Met Asn Tyr Cys Arg Asn Pro Asp Asn Asp Gln
            420                 425                 430
Arg Gly Pro Trp Cys Phe Thr Thr Asp Pro Ser Val Arg Trp Glu Tyr
        435                 440                 445
Cys Asn Leu Lys Arg Cys Ser Glu Thr Gly Gly Val Ala Glu Ser
    450                 455                 460
Ala Ile Val Pro Gln Val Pro Ser Ala Pro Gly Thr Ser Glu Thr Asp
465                 470                 475                 480
Cys Met Tyr Gly Asn Gly Lys Glu Tyr Arg Gly Lys Thr Ala Val Thr
                485                 490                 495
Ala Ala Gly Thr Pro Cys Gln Glu Trp Ala Ala Gln Glu Pro His Ser
            500                 505                 510
His Arg Ile Phe Thr Pro Gln Thr Asn Pro Arg Ala Gly Leu Glu Lys
        515                 520                 525
Asn Tyr Cys Arg Asn Pro Asp Gly Asp Val Asn Gly Pro Trp Cys Tyr
530                 535                 540
Thr Met Asn Pro Arg Lys Leu Tyr Asp Tyr Cys Asn Ile Pro Leu Cys
545                 550                 555                 560
Ala Ser Leu Ser Ser Phe Glu Cys Gly Lys Pro Gln Val Glu Pro Lys
                565                 570                 575
Lys Cys Pro Gly Arg Val Val Gly Gly Cys Val Ala Asn Pro His Ser
            580                 585                 590
Trp Pro Trp Gln Ile Ser Leu Arg Thr Arg Phe Ser Gly Gln His Phe
        595                 600                 605
Cys Gly Gly Thr Leu Ile Ser Pro Glu Trp Val Leu Thr Ala Ala His
    610                 615                 620
```

```
Cys Leu Glu Lys Ser Ser Arg Pro Glu Phe Tyr Lys Val Ile Leu Gly
625                 630                 635                 640

Ala His Glu Glu Arg Ile Leu Gly Ser Asp Val Gln Gln Ile Ala Val
            645                 650                 655

Thr Lys Leu Val Leu Glu Pro Asn Asp Ala Asp Ile Ala Leu Leu Lys
            660                 665                 670

Leu Ser Arg Pro Ala Thr Ile Thr Asp Asn Val Ile Pro Ala Cys Leu
            675                 680                 685

Pro Ser Pro Asn Tyr Val Val Ala Asp Arg Thr Leu Cys Tyr Ile Thr
690                 695                 700

Gly Trp Gly Glu Thr Lys Gly Thr Pro Gly Ala Gly Arg Leu Lys Glu
705                 710                 715                 720

Ala Gln Leu Pro Val Ile Glu Asn Lys Val Cys Asn Arg Ala Glu Tyr
            725                 730                 735

Leu Asn Asn Arg Val Lys Ser Thr Glu Leu Cys Ala Gly His Leu Ala
            740                 745                 750

Gly Gly Ile Asp Ser Cys Gln Gly Asp Ser Gly Gly Pro Leu Val Cys
            755                 760                 765

Phe Glu Lys Asp Lys Tyr Ile Leu Gln Gly Val Thr Ser Trp Gly Leu
770                 775                 780

Gly Cys Ala Arg Pro Asn Lys Pro Gly Val Tyr Val Arg Val Ser Arg
785                 790                 795                 800

Tyr Val Asn Trp Ile Glu Arg Glu Met Arg Asn Asp
                805                 810

<210> SEQ ID NO 13
<211> LENGTH: 811
<212> TYPE: PRT
<213> ORGANISM: Erinaceus europaeus

<400> SEQUENCE: 13

Met Gln Arg Lys Glu Leu Val Leu Leu Phe Leu Leu Phe Leu Gln Pro
1               5                   10                  15

Gly His Gly Ile Pro Leu Asp Asp Tyr Val Thr Thr Gln Gly Ala Ser
            20                  25                  30

Leu Ser Ser Ser Thr Lys Lys Gln Leu Ser Val Gly Ser Thr Glu Glu
        35                  40                  45

Cys Ala Val Lys Cys Glu Lys Glu Thr Ser Phe Ile Cys Arg Ser Phe
    50                  55                  60

Gln Tyr His Ser Lys Glu Gln Gln Cys Val Ile Met Ala Glu Asn Ser
65                  70                  75                  80

Lys Ser Thr Pro Val Leu Arg Met Arg Asp Val Ile Leu Phe Glu Lys
                85                  90                  95

Lys Met Tyr Leu Ser Glu Cys Lys Val Gly Asn Gly Lys Tyr Tyr Arg
            100                 105                 110

Gly Thr Val Ser Lys Thr Lys Thr Gly Leu Thr Cys Gln Lys Trp Ser
            115                 120                 125

Ala Glu Thr Pro His Lys Pro Arg Phe Ser Pro Asp Glu Asn Pro Ser
        130                 135                 140

Glu Gly Leu Asp Gln Asn Tyr Cys Arg Asn Pro Asp Asn Asp Pro Lys
145                 150                 155                 160

Gly Pro Trp Cys Tyr Thr Met Asp Pro Glu Val Arg Tyr Glu Tyr Cys
                165                 170                 175

Glu Ile Ile Gln Cys Glu Asp Glu Cys Met His Cys Ser Gly Gln Asn
            180                 185                 190
```

Tyr Val Gly Lys Ile Ser Arg Thr Met Ser Gly Leu Glu Cys Gln Pro
            195                 200                 205
Trp Asp Ser Gln Ile Pro His Pro His Gly Phe Ile Pro Ser Lys Phe
210                 215                 220
Pro Ser Lys Asn Leu Lys Met Asn Tyr Cys Arg Asn Pro Asp Gly Glu
225                 230                 235                 240
Pro Arg Pro Trp Cys Phe Thr Met Asp Arg Asn Lys Arg Trp Glu Tyr
            245                 250                 255
Cys Asp Ile Pro Arg Cys Thr Thr Pro Pro Pro Ser Gly Pro Thr
            260                 265                 270
Tyr Gln Cys Leu Met Gly Asn Gly Glu His Tyr Gln Gly Asn Val Ala
            275                 280                 285
Val Thr Val Ser Gly Leu Thr Cys Gln Arg Trp Gly Glu Gln Ser Pro
            290                 295                 300
His Arg His Asp Arg Thr Pro Glu Asn Tyr Pro Cys Lys Asn Leu Asp
305                 310                 315                 320
Glu Asn Tyr Cys Arg Asn Pro Asp Gly Glu Pro Ala Pro Trp Cys Phe
                        325                 330                 335
Thr Thr Asn Ser Ser Val Arg Trp Glu Phe Cys Lys Ile Pro Asp Cys
            340                 345                 350
Val Ser Ser Ala Ser Glu Thr Glu His Ser Asp Ala Pro Val Ile Val
            355                 360                 365
Pro Pro Glu Gln Thr Pro Val Val Gln Glu Cys Tyr Gln Gly Asn Gly
            370                 375                 380
Gln Ser Tyr Arg Gly Thr Ser Ser Thr Thr Ile Thr Gly Lys Lys Cys
385                 390                 395                 400
Gln Pro Trp Thr Ser Met Arg Pro His Arg His Ser Lys Thr Pro Glu
            405                 410                 415
Asn Tyr Pro Asp Ala Asp Leu Thr Met Asn Tyr Cys Arg Asn Pro Asp
            420                 425                 430
Gly Asp Lys Gly Pro Trp Cys Tyr Thr Thr Asp Pro Ser Val Arg Trp
            435                 440                 445
Glu Phe Cys Asn Leu Lys Lys Cys Ser Gly Thr Glu Met Ser Ala Thr
            450                 455                 460
Asn Ser Ser Pro Val Gln Val Ser Ser Ala Ser Glu Ser Ser Glu Gln
465                 470                 475                 480
Asp Cys Ile Ile Asp Asn Gly Lys Gly Tyr Arg Gly Thr Lys Ala Thr
            485                 490                 495
Thr Gly Ala Gly Thr Pro Cys Gln Ala Trp Ala Ala Gln Glu Pro His
            500                 505                 510
Arg His Ser Ile Phe Thr Pro Glu Thr Asn Pro Arg Ala Asp Leu Gln
            515                 520                 525
Glu Asn Tyr Cys Arg Asn Pro Asp Gly Asp Ala Asn Gly Pro Trp Cys
            530                 535                 540
Tyr Thr Thr Asn Pro Arg Lys Leu Phe Asp Tyr Cys Asp Ile Pro His
545                 550                 555                 560
Cys Val Ser Pro Ser Ser Ala Asp Cys Gly Lys Pro Lys Val Glu Pro
            565                 570                 575
Lys Lys Cys Pro Gly Arg Val Val Gly Gly Cys Val Ala Asn Pro His
            580                 585                 590
Ser Trp Pro Trp Gln Val Ser Leu Arg Arg Phe Gly Gln His Phe Cys
            595                 600                 605

```
Gly Gly Thr Leu Ile Ser Pro Glu Trp Val Val Ala Ala His Cys
    610             615                 620

Leu Glu Lys Phe Ser Asn Pro Ala Ile Tyr Lys Val Val Leu Gly Ala
625                 630                 635                 640

His Gln Glu Thr Arg Leu Glu Arg Asp Val Gln Ile Lys Gly Val Thr
                645                 650                 655

Lys Met Phe Leu Glu Pro Tyr Arg Ala Asp Ile Ala Leu Leu Lys Leu
            660                 665                 670

Ser Ser Pro Ala Ile Ile Thr Asp Lys Ile Ile Pro Ala Cys Leu Pro
        675                 680                 685

Asn Ser Asn Tyr Met Val Ala Asp Arg Ser Leu Cys Tyr Ile Thr Gly
    690                 695                 700

Trp Gly Glu Thr Lys Gly Thr Tyr Gly Ala Gly Leu Leu Lys Glu Ala
705                 710                 715                 720

Gln Leu Pro Val Ile Glu Asn Lys Val Cys Asn Arg Gln Glu Leu Leu
                725                 730                 735

Asn Gly Arg Val Arg Ser Thr Glu Leu Cys Ala Gly His Leu Ala Gly
            740                 745                 750

Gly Val Asp Ser Cys Gln Gly Asp Ser Gly Gly Pro Leu Val Cys Phe
        755                 760                 765

Glu Lys Asp Arg Tyr Ile Leu Gln Gly Val Thr Ser Trp Gly Leu Gly
    770                 775                 780

Cys Ala Arg Pro Asn Lys Pro Gly Val Tyr Val Arg Val Ser Arg Tyr
785                 790                 795                 800

Val Ser Trp Leu Gln Asp Val Met Arg Asn Asn
                805                 810

<210> SEQ ID NO 14
<211> LENGTH: 780
<212> TYPE: PRT
<213> ORGANISM: Oryctolagus cuniculus

<400> SEQUENCE: 14

Met Glu Gln Arg Ala Val Val Leu Leu Leu Leu Leu Leu Lys Pro
1               5                   10                  15

Gly Gln Ala Glu Pro Leu Asp Asp Tyr Val Asn Thr Gln Gly Ala Ser
            20                  25                  30

Leu Phe Ser Phe Thr Lys Lys Gln Leu Gly Ala Ala Ser Ile Ala Glu
        35                  40                  45

Cys Ala Ala Arg Cys Glu Ala Glu Thr Glu Phe Thr Cys Arg Ser Phe
    50                  55                  60

Gln Tyr His Ser Lys Glu Gln Gln Cys Val Val Met Ala Glu Asn Ser
65                  70                  75                  80

Lys Ser Ser Ala Ile Ile Arg Arg Asp Val Val Leu Phe Glu Lys
                85                  90                  95

Arg Met Tyr Leu Ser Glu Cys Lys Ile Gly Asn Gly Arg Ser Tyr Arg
            100                 105                 110

Gly Thr Lys Ser Lys Thr Lys Thr Gly Phe Thr Cys Gln Lys Trp Ser
        115                 120                 125

Ser Ser Tyr Pro His Lys Pro Asn Phe Thr Pro Lys Lys Tyr Pro Ala
    130                 135                 140

Glu Gly Leu Glu Glu Asn Tyr Cys Arg Asn Pro Asp Asn Asp Glu Gln
145                 150                 155                 160

Gly Pro Trp Cys Tyr Thr Thr Asn Pro Asp Glu Arg Phe Asp Tyr Cys
                165                 170                 175
```

```
Asp Ile Pro Glu Cys Glu Asp Glu Cys Met His Cys Ser Gly Glu Asn
            180                 185                 190

Tyr Glu Gly Lys Ile Ser Lys Thr Met Ser Gly Ile Glu Cys Gln Ala
        195                 200                 205

Trp Asp Ser Gln Ser Pro His Ala His Gly Tyr Ile Pro Ser Lys Phe
210                 215                 220

Pro Asn Lys Asn Leu Lys Lys Asn Tyr Cys Arg Asn Pro Asp Gly Glu
225                 230                 235                 240

Pro Arg Pro Trp Cys Phe Thr Met Asp Pro Lys Lys Arg Trp Glu Leu
                245                 250                 255

Cys Asp Ile Pro Arg Cys Thr Thr Pro Pro Pro Ser Gly Pro Thr
            260                 265                 270

His Gln Cys Leu Lys Gly Arg Gly Glu Ser Tyr Arg Gly Lys Val Ala
        275                 280                 285

Arg Thr Lys Ser Gly Leu Thr Cys Gln Arg Trp Ser Glu Gln Thr Pro
290                 295                 300

His Leu His Asn Arg Thr Pro Glu Asn Phe Pro Cys Lys Asp Leu Asp
305                 310                 315                 320

Glu Asn Tyr Cys Arg Asn Pro Asp Gly Glu Ser Ala Pro Trp Cys Tyr
                325                 330                 335

Thr Thr Asp Ser Lys Val Arg Trp Glu His Cys Asp Ile Pro Ser Cys
            340                 345                 350

Ala Ser Ser Pro Thr Ser Val Glu Pro Leu Asp Ala Pro Ala Pro Pro
        355                 360                 365

Glu Glu Thr Pro Val Val Gln Glu Cys Tyr Gln Gly Asn Gly Gln Ser
        370                 375                 380

Tyr Arg Gly Thr Ser Ser Thr Thr Ile Thr Gly Arg Lys Cys Gln Ser
385                 390                 395                 400

Trp Leu Ser Met Thr Pro His Arg His Gln Arg Thr Pro Gln Asn Tyr
                405                 410                 415

Pro Asn Ala Asp Leu Thr Met Asn Tyr Cys Arg Asn Pro Asp Asp Asp
            420                 425                 430

Ile Arg Pro Trp Cys Tyr Thr Thr Asp Pro Ser Val Arg Trp Glu Tyr
        435                 440                 445

Cys Asn Leu Arg Arg Cys Ser Glu Pro Ala Ala Ser Pro Ala Ala Thr
450                 455                 460

Val Pro Thr Ala Gln Leu Pro Arg Pro Glu Ala Thr Phe Glu Pro Asp
465                 470                 475                 480

Cys Met Phe Gly Asn Gly Lys Gly Tyr Arg Gly Lys Lys Ala Thr Thr
                485                 490                 495

Ala Asp Gly Thr Pro Cys Gln Gly Trp Ala Ala Gln Glu Pro His Arg
            500                 505                 510

His Asn Ile Phe Thr Pro Glu Thr Asn Pro Arg Ala Gly Leu Glu Arg
        515                 520                 525

Asn Tyr Cys Arg Asn Pro Asp Gly Asp Thr Asn Gly Pro Trp Cys Tyr
        530                 535                 540

Thr Met Asn Pro Arg Lys Leu Tyr Asp Tyr Cys Asp Val Pro Gln Cys
545                 550                 555                 560

Ala Ser Ser Ser Tyr Asp Cys Gly Lys Pro Lys Val Glu Pro Lys
                565                 570                 575

Lys Cys Pro Gly Arg Val Val Gly Gly Cys Val Ala Asn Pro His Ser
            580                 585                 590
```

Trp Pro Trp Gln Ile Ser Leu Arg Thr Arg Thr Gly Gln His Phe Cys
            595                 600                 605

Gly Gly Thr Leu Ile Ala Pro Glu Trp Val Leu Thr Ala Ala His Cys
    610                 615                 620

Leu Glu Lys Tyr Pro Arg Pro Ser Ala Tyr Arg Val Ile Leu Gly Ala
625                 630                 635                 640

His Lys Glu Val Asn Leu Glu Leu Asp Val Gln Asp Ile Asp Val Ala
                645                 650                 655

Lys Leu Phe Leu Glu Pro Ser Arg Ala Asp Ile Ala Leu Met Lys Leu
            660                 665                 670

Ser Ser Leu Glu Trp Ala Trp Thr Tyr Gly Ala Gly Leu Leu Lys Glu
        675                 680                 685

Ala Gln Leu Pro Val Ile Glu Asn Lys Val Cys Asn Arg Phe Glu Tyr
    690                 695                 700

Leu Asn Gly Arg Val Arg Ser Thr Glu Leu Cys Ala Gly His Leu Ala
705                 710                 715                 720

Gly Gly Thr Asp Ser Cys Gln Gly Asp Ser Gly Gly Pro Leu Val Cys
                725                 730                 735

Phe Glu Lys Asp Lys Tyr Ile Leu Gln Gly Val Thr Ser Trp Gly Leu
            740                 745                 750

Gly Cys Ala Arg Pro Asn Lys Pro Gly Val Tyr Val Arg Val Ser Arg
        755                 760                 765

Phe Val Asp Trp Ile Glu Arg Thr Met Arg Asn Asn
    770                 775                 780

<210> SEQ ID NO 15
<211> LENGTH: 827
<212> TYPE: PRT
<213> ORGANISM: Pan troglodytes

<400> SEQUENCE: 15

Met Glu His Lys Glu Val Val Leu Leu Leu Leu Phe Leu Lys Ser
1               5                   10                  15

Gly Gln Gly Glu Pro Leu Asp Asp Tyr Val Asn Thr Gln Gly Ala Ser
            20                  25                  30

Leu Phe Ser Val Thr Lys Lys Gln Leu Gly Ala Gly Ser Ile Glu Glu
        35                  40                  45

Cys Ala Ala Lys Cys Glu Glu Asp Lys Glu Phe Thr Cys Arg Tyr Phe
    50                  55                  60

His Cys Arg Cys Thr Tyr Pro Glu Ile Cys Asn Ser Asp Gly Lys Ala
65                  70                  75                  80

Phe Gln Tyr His Ser Lys Glu Gln Gln Cys Val Ile Met Ala Glu Asn
                85                  90                  95

Arg Lys Ser Ser Ile Ile Arg Met Arg Asp Val Val Leu Phe Glu
            100                 105                 110

Lys Lys Val Tyr Leu Ser Glu Cys Lys Thr Gly Asn Gly Lys Asn Tyr
        115                 120                 125

Arg Gly Thr Met Ser Lys Thr Lys Asn Gly Ile Thr Cys Gln Lys Trp
    130                 135                 140

Ser Ser Thr Ser Pro His Arg Pro Arg Phe Ser Pro Ala Thr His Pro
145                 150                 155                 160

Ser Glu Gly Leu Glu Glu Asn Tyr Cys Arg Asn Pro Asp Asn Asp Pro
                165                 170                 175

Gln Gly Pro Trp Cys Tyr Thr Thr Asp Pro Glu Lys Arg Tyr Asp Tyr
            180                 185                 190

```
Cys Asp Ile Leu Glu Cys Glu Glu Cys Met His Cys Ser Gly Glu
        195                 200                 205

Asn Tyr Asp Gly Lys Ile Ser Lys Thr Met Ser Gly Leu Glu Cys Gln
210                 215                 220

Ala Trp Asp Ser Gln Ser Pro His Ala His Gly Tyr Ile Pro Ser Lys
225                 230                 235                 240

Phe Pro Asn Lys Asn Leu Lys Lys Asn Tyr Cys Arg Asn Pro Asp Gly
                245                 250                 255

Glu Leu Arg Pro Trp Cys Phe Thr Thr Asp Pro Asn Lys Arg Trp Glu
            260                 265                 270

Leu Cys Asp Ile Pro Arg Cys Thr Thr Pro Pro Ser Ser Gly Pro
        275                 280                 285

Thr Tyr Gln Cys Leu Lys Gly Thr Gly Glu Asn Tyr Arg Gly Asn Val
290                 295                 300

Ala Val Thr Val Ser Gly His Thr Cys Gln His Trp Ser Ala Gln Thr
305                 310                 315                 320

Pro His Thr His Asn Arg Thr Pro Glu Asn Phe Pro Cys Lys Asn Leu
                325                 330                 335

Asp Glu Asn Tyr Cys Arg Asn Pro Asp Gly Lys Arg Ala Pro Trp Cys
            340                 345                 350

His Thr Thr Asn Ser Gln Val Arg Trp Glu Tyr Cys Lys Ile Pro Ser
        355                 360                 365

Cys Asp Ser Ser Leu Val Ser Thr Glu Gln Leu Ala Pro Thr Ala Pro
370                 375                 380

Pro Glu Leu Thr Pro Val Val Gln Asp Cys Tyr His Gly Asp Gly Gln
385                 390                 395                 400

Ser Tyr Arg Gly Thr Ser Ser Thr Thr Thr Thr Gly Lys Lys Cys Gln
                405                 410                 415

Ser Trp Ser Ser Met Thr Pro His Arg His Gln Lys Thr Pro Glu Asn
            420                 425                 430

Tyr Pro Asn Ala Gly Leu Thr Met Asn Tyr Cys Arg Asn Pro Asp Ala
        435                 440                 445

Asp Lys Gly Pro Trp Cys Phe Thr Thr Asp Pro Ser Val Arg Trp Glu
450                 455                 460

Tyr Cys Asn Leu Lys Lys Cys Ser Gly Thr Glu Ala Ser Val Val Ala
465                 470                 475                 480

Pro Pro Pro Val Val Gln Leu Pro Asn Val Glu Thr Pro Ser Glu Glu
                485                 490                 495

Asp Cys Met Phe Gly Asn Gly Lys Gly Tyr Arg Gly Lys Arg Ala Thr
            500                 505                 510

Thr Val Thr Gly Thr Pro Cys Gln Asp Trp Ala Ala Gln Glu Pro His
        515                 520                 525

Arg His Ser Ile Phe Thr Pro Glu Thr Asn Pro Arg Ala Gly Leu Glu
530                 535                 540

Lys Asn Tyr Cys Arg Asn Pro Asp Gly Asp Val Gly Gly Pro Trp Cys
545                 550                 555                 560

Tyr Thr Thr Asn Pro Arg Lys Leu Tyr Asp Tyr Cys Asp Val Pro Gln
                565                 570                 575

Cys Ala Ser Pro Ser Phe Asp Cys Gly Lys Pro Gln Val Glu Pro Lys
            580                 585                 590

Lys Cys Pro Gly Arg Val Val Gly Gly Cys Val Ala His Pro His Ser
        595                 600                 605
```

```
Trp Pro Trp Gln Val Ser Leu Arg Thr Arg Leu Gly Met His Phe Cys
    610             615                 620

Gly Gly Thr Leu Ile Ser Pro Glu Trp Val Leu Thr Ala Ala His Cys
625                 630                 635                 640

Leu Glu Lys Ser Pro Arg Pro Ser Ser Tyr Lys Val Ile Leu Gly Ala
                645                 650                 655

His Gln Glu Val Lys Leu Pro His Val Gln Glu Ile Glu Val Ser
            660                 665                 670

Arg Leu Phe Leu Glu Pro Thr Arg Thr Asp Ile Ala Leu Leu Lys Leu
            675                 680                 685

Ser Ser Pro Ala Ile Ile Thr Asp Lys Val Ile Pro Ala Cys Leu Pro
690                 695                 700

Ser Pro Asn Tyr Val Val Ala Asp Arg Thr Glu Cys Phe Ile Thr Gly
705                 710                 715                 720

Trp Gly Glu Thr Gln Gly Thr Phe Gly Ala Gly Leu Leu Lys Glu Ala
                725                 730                 735

Gln Leu Pro Val Ile Glu Asn Lys Val Cys Asn Arg Asn Glu Phe Leu
                740                 745                 750

Asn Gly Arg Val Lys Ser Thr Glu Leu Cys Ala Gly His Leu Ala Gly
            755                 760                 765

Gly Thr Asp Ser Cys Gln Gly Asp Ser Gly Gly Pro Leu Val Cys Phe
770                 775                 780

Glu Lys Asp Lys Tyr Ile Leu Gln Gly Val Thr Ser Trp Gly Leu Gly
785                 790                 795                 800

Cys Ala Arg Pro Asn Lys Pro Gly Val Tyr Val Arg Val Ser Arg Phe
                805                 810                 815

Val Thr Trp Ile Glu Gly Val Met Arg Asn Asn
            820                 825

<210> SEQ ID NO 16
<211> LENGTH: 769
<212> TYPE: PRT
<213> ORGANISM: Ailuropoda melanoleuca

<400> SEQUENCE: 16

Phe Val Arg Arg Ser Phe Glu Tyr His Ser Lys Glu Gln Gln Cys Ala
1               5                   10                  15

Ile Met Ala Glu Asn Ser Lys Ser Ala Val Phe Arg Met Arg Asp
            20                  25                  30

Val Ile Leu Phe Gln Lys Arg Ile Tyr Leu Ser Glu Cys Lys Thr Gly
            35                  40                  45

Asn Gly Lys Thr Tyr Arg Gly Thr Met Ser Lys Thr Lys Asn Gly Val
50                  55                  60

Ala Cys Gln Lys Trp Ser Asp Thr Phe Pro His Lys Pro Asn Tyr Thr
65                  70                  75                  80

Pro Glu Lys His Pro Leu Glu Gly Leu Glu Glu Asn Tyr Cys Arg Asn
                85                  90                  95

Pro Asp Asn Asp Glu Lys Gly Pro Trp Cys Tyr Thr Thr Asp Pro Asn
                100                 105                 110

Gln Arg Phe Asp Tyr Cys Ser Ile Pro Gln Cys Glu Asp Glu Cys Met
            115                 120                 125

His Cys Ser Gly Glu Asn Tyr Glu Gly Lys Val Ser Lys Thr Lys Ser
130                 135                 140

Gly Leu Glu Cys Gln Ala Trp Asn Ser Gln Thr Pro His Ala His Gly
145                 150                 155                 160
```

```
Tyr Ile Pro Ser Lys Phe Pro Asn Lys Asn Leu Lys Met Asn Tyr Cys
                165                 170                 175
Arg Asn Pro Asp Gly Glu Pro Arg Pro Trp Cys Phe Thr Met Asp Pro
            180                 185                 190
Asn Lys Arg Trp Glu Phe Cys Asp Ile Pro Arg Cys Thr Thr Pro Pro
        195                 200                 205
Pro Pro Ser Gly Pro Thr Tyr Gln Cys Leu Lys Gly Lys Gly Glu Asn
    210                 215                 220
Tyr Arg Gly Lys Val Ser Val Thr Ala Ser Gly His Thr Cys Gln Arg
225                 230                 235                 240
Trp Ser Glu Gln Thr Pro His Lys His Asn Arg Thr Pro Glu Asn Phe
                245                 250                 255
Pro Cys Lys Asn Leu Asp Glu Asn Tyr Cys Arg Asn Pro Asp Gly Glu
            260                 265                 270
Ser Ala Pro Trp Cys Tyr Thr Thr Asp Ser Glu Val Arg Trp Glu His
        275                 280                 285
Cys Ser Ile Pro Ser Cys Glu Ser Ser Pro Leu Thr Leu Asp Ser Leu
    290                 295                 300
Asp Thr Pro Ala Ser Ile Pro Pro Glu Gln Thr Pro Val Val Gln Glu
305                 310                 315                 320
Cys Tyr Gln Gly Asn Gly Gln Thr Tyr Arg Gly Thr Ser Ser Thr Thr
                325                 330                 335
Ile Thr Gly Lys Lys Cys Gln Pro Trp Ser Ser Met Ser Pro His Arg
            340                 345                 350
His Glu Lys Thr Pro Glu Arg Phe Pro Asn Ala Gly Leu Thr Met Asn
        355                 360                 365
Tyr Cys Arg Asn Pro Asp Gly Asp Lys Ser Pro Trp Cys Tyr Thr Thr
    370                 375                 380
Asp Pro Ser Val Arg Trp Glu Phe Cys Asn Leu Lys Lys Cys Leu Asp
385                 390                 395                 400
Thr Glu Glu Ser Gly Thr Ser Ser Pro Thr Val Pro Gln Val Pro Ser
                405                 410                 415
Gly Glu Glu Pro Ser Glu Thr Asp Cys Met Phe Gly Asn Gly Lys Gly
            420                 425                 430
Tyr Arg Gly Lys Lys Ala Thr Thr Val Leu Gly Ile Pro Cys Gln Glu
        435                 440                 445
Trp Thr Ala Gln Glu Pro His Lys His Ser Ile Phe Thr Pro Glu Thr
    450                 455                 460
Asn Pro Arg Ala Glu His Leu Leu Cys Pro Thr Cys Leu Val Pro Ser
465                 470                 475                 480
Val Pro Thr Val Phe Phe Phe Phe Phe Phe Leu Phe Leu Asp
                485                 490                 495
Val Asn Gly Pro Trp Cys Tyr Thr Thr Asn Pro Arg Lys Leu Phe Asp
            500                 505                 510
Tyr Cys Asp Ile Pro Gln Cys Ala Ser Gly Ser Phe Asp Cys Gly Lys
        515                 520                 525
Pro Gln Val Glu Pro Lys Lys Cys Pro Gly Arg Val Val Gly Gly Cys
    530                 535                 540
Val Ala Asn Pro His Ser Trp Pro Trp Gln Ile Ser Leu Arg Thr Arg
545                 550                 555                 560
Phe Gly Gln His Phe Cys Gly Gly Thr Leu Ile Ser Pro Glu Trp Val
                565                 570                 575
```

```
Leu Thr Ala Ala His Cys Leu Glu Arg Ser Pro Arg Pro Ala Ala Tyr
                580                 585                 590

Lys Val Ile Leu Gly Ala His Arg Glu Phe Asn Leu Glu Ser Asp Val
            595                 600                 605

Gln Glu Ile Glu Val Ser Lys Leu Phe Leu Glu Pro Thr His Ala Asp
        610                 615                 620

Ile Ala Leu Ile Lys Leu Gln Ser Pro Ala Val Leu Thr Ser Lys Val
625                 630                 635                 640

Ile Pro Ala Cys Leu Pro Ser Pro Asn Tyr Val Val Ala Asp Arg Thr
                645                 650                 655

Leu Cys Tyr Ile Thr Gly Trp Gly Glu Thr Gln Gly Thr Phe Gly Val
            660                 665                 670

Gly Leu Leu Lys Glu Ala Gln Leu Pro Val Ile Glu Asn Lys Val Cys
        675                 680                 685

Asn Arg Tyr Glu Tyr Leu Asn Gly Lys Val Lys Ser Thr Glu Leu Cys
690                 695                 700

Ala Gly Asn Leu Ala Gly Gly Thr Asp Ser Cys Gln Gly Asp Ser Gly
705                 710                 715                 720

Gly Pro Leu Val Cys Phe Glu Lys Asp Lys Tyr Ile Leu Gln Gly Val
                725                 730                 735

Thr Ser Trp Gly Leu Gly Cys Ala Arg Pro Asn Lys Pro Gly Val Tyr
            740                 745                 750

Val Arg Val Ser Arg Phe Val Thr Trp Ile Glu Ile Met Arg Asn
        755                 760                 765

Asn

<210> SEQ ID NO 17
<211> LENGTH: 334
<212> TYPE: PRT
<213> ORGANISM: Papio hamadryas

<400> SEQUENCE: 17

Ile Arg Leu Asp Cys Met Phe Gly Asn Gly Lys Arg Tyr Arg Gly Lys
1               5                   10                  15

Lys Ala Thr Thr Val Thr Gly Thr Pro Cys Gln Glu Trp Ala Ala Lys
            20                  25                  30

Glu Pro His Ser His Leu Ile Phe Thr Pro Glu Thr Tyr Pro Arg Ala
        35                  40                  45

Gly Leu Glu Lys Asn Tyr Cys Arg Asn Pro Asp Gly Asp Val Gly Gly
    50                  55                  60

Pro Trp Cys Tyr Thr Thr Asn Pro Arg Lys Leu Tyr Asp Tyr Cys Asp
65                  70                  75                  80

Val Pro Gln Cys Ala Ser Ser Ser Phe Asp Cys Gly Lys Pro Gln Val
                85                  90                  95

Glu Pro Lys Lys Cys Pro Gly Arg Val Val Gly Gly Cys Val Ala His
            100                 105                 110

Ala His Ser Trp Pro Trp Gln Val Ser Leu Arg Thr Arg Phe Gly Met
        115                 120                 125

His Phe Cys Gly Gly Thr Leu Ile Ser Pro Glu Trp Val Leu Thr Ala
    130                 135                 140

Ala His Cys Leu Glu Lys Ser Pro Arg Pro Ser Phe Tyr Lys Val Ile
145                 150                 155                 160

Leu Gly Ala His Gln Glu Val Arg Leu Glu Pro His Val Gln Glu Ile
                165                 170                 175
```

```
Glu Val Ser Lys Met Phe Ser Glu Pro Ala Gly Ala Asp Ile Ala Leu
            180                 185                 190

Leu Lys Leu Ser Ser Pro Ala Ile Ile Thr Asp Lys Val Ile Pro Ala
        195                 200                 205

Cys Leu Pro Ser Pro Asn Tyr Val Val Ala Asp Arg Thr Glu Cys Phe
    210                 215                 220

Ile Thr Gly Trp Gly Glu Thr Gln Gly Thr Tyr Gly Ala Gly Leu Leu
225                 230                 235                 240

Lys Glu Ala Arg Leu Pro Val Ile Glu Asn Lys Val Cys Asn Arg Tyr
                245                 250                 255

Glu Phe Leu Asn Gly Arg Val Lys Ser Thr Glu Leu Cys Ala Gly His
            260                 265                 270

Leu Ala Gly Gly Thr Asp Ser Cys Gln Gly Asp Ser Gly Gly Pro Leu
        275                 280                 285

Val Cys Phe Glu Lys Asp Lys Tyr Ile Leu Gln Gly Val Thr Ser Trp
    290                 295                 300

Gly Leu Gly Cys Ala Arg Pro Asn Lys Pro Gly Val Tyr Val Arg Val
305                 310                 315                 320

Ser Arg Phe Val Thr Trp Ile Glu Gly Val Met Arg Asn Asn
                325                 330

<210> SEQ ID NO 18
<211> LENGTH: 343
<212> TYPE: PRT
<213> ORGANISM: Ovis aries

<400> SEQUENCE: 18

Ala Pro Gln Ala Pro Ser Val Glu Asn Pro Pro Glu Ala Asp Cys Met
1               5                   10                  15

Leu Gly Ile Gly Lys Gly Tyr Arg Gly Lys Lys Ala Thr Thr Val Ala
            20                  25                  30

Gly Val Pro Cys Gln Glu Trp Ala Ala Gln Glu Pro His Arg His Gly
        35                  40                  45

Ile Phe Thr Pro Glu Thr Asn Pro Arg Ala Gly Leu Glu Lys Asn Tyr
    50                  55                  60

Cys Arg Asn Pro Asp Gly Asp Val Asn Gly Pro Trp Cys Tyr Thr Thr
65                  70                  75                  80

Asn Pro Arg Lys Leu Phe Asp Tyr Cys Asp Ile Pro Gln Cys Glu Ser
                85                  90                  95

Ser Phe Asp Cys Gly Lys Pro Lys Val Glu Pro Lys Lys Cys Pro Ala
            100                 105                 110

Arg Val Val Gly Gly Cys Val Ala Thr Pro His Ser Trp Pro Trp Gln
        115                 120                 125

Val Ser Leu Arg Arg Arg Ser Arg Glu His Phe Cys Gly Gly Thr Leu
    130                 135                 140

Ile Ser Pro Glu Trp Val Leu Thr Ala Ala His Cys Leu Asp Ser Ile
145                 150                 155                 160

Leu Gly Pro Ser Phe Tyr Thr Val Ile Leu Gly Ala His Tyr Glu Met
                165                 170                 175

Ala Arg Glu Ala Ser Val Gln Glu Ile Pro Val Ser Arg Leu Phe Leu
            180                 185                 190

Glu Pro Ser Arg Ala Asp Ile Ala Leu Leu Lys Leu Ser Ser Pro Ala
        195                 200                 205

Val Ile Thr Asp Glu Val Ile Pro Ala Cys Leu Pro Ser Pro Asn Tyr
    210                 215                 220
```

```
Val Val Ala Asp Lys Thr Val Cys Tyr Ile Thr Gly Trp Gly Glu Thr
225                 230                 235                 240

Gln Gly Thr Phe Gly Val Gly Arg Leu Lys Glu Ala Arg Leu Pro Val
            245                 250                 255

Ile Glu Asn Lys Val Cys Asn Arg Tyr Glu Tyr Leu Asn Gly Arg Val
            260                 265                 270

Lys Ser Thr Glu Leu Cys Ala Gly Asp Leu Ala Gly Gly Thr Asp Ser
            275                 280                 285

Cys Gln Gly Asp Ser Gly Gly Pro Leu Val Cys Phe Glu Lys Asp Lys
            290                 295                 300

Tyr Ile Leu Gln Gly Val Thr Ser Trp Gly Leu Gly Cys Ala Arg Pro
305                 310                 315                 320

Asn Lys Pro Gly Val Tyr Val Arg Val Ser Thr Tyr Val Pro Trp Ile
            325                 330                 335

Glu Glu Thr Met Arg Arg Tyr
            340

<210> SEQ ID NO 19
<211> LENGTH: 249
<212> TYPE: PRT
<213> ORGANISM: Homo sapiens

<400> SEQUENCE: 19

Ala Pro Ser Phe Asp Cys Gly Lys Pro Gln Val Glu Pro Lys Lys Cys
1               5                   10                  15

Pro Gly Arg Val Val Gly Gly Cys Val Ala His Pro His Ser Trp Pro
            20                  25                  30

Trp Gln Val Ser Leu Arg Thr Arg Phe Gly Met His Phe Cys Gly Gly
            35                  40                  45

Thr Leu Ile Ser Pro Glu Trp Val Leu Thr Ala Ala His Cys Leu Glu
50                  55                  60

Lys Ser Pro Arg Pro Ser Ser Tyr Lys Val Ile Leu Gly Ala His Gln
65                  70                  75                  80

Glu Val Asn Leu Glu Pro His Val Gln Glu Ile Glu Val Ser Arg Leu
            85                  90                  95

Phe Leu Glu Pro Thr Arg Lys Asp Ile Ala Leu Leu Lys Leu Ser Ser
            100                 105                 110

Pro Ala Val Ile Thr Asp Lys Val Ile Pro Ala Cys Leu Pro Ser Pro
            115                 120                 125

Asn Tyr Val Val Ala Asp Arg Thr Glu Cys Phe Ile Thr Gly Trp Gly
            130                 135                 140

Glu Thr Gln Gly Thr Phe Gly Ala Gly Leu Leu Lys Glu Ala Gln Leu
145                 150                 155                 160

Pro Val Ile Glu Asn Lys Val Cys Asn Arg Tyr Glu Phe Leu Asn Gly
            165                 170                 175

Arg Val Gln Ser Thr Glu Leu Cys Ala Gly His Leu Ala Gly Gly Thr
            180                 185                 190

Asp Ser Cys Gln Gly Asp Ser Gly Gly Pro Leu Val Cys Phe Glu Lys
            195                 200                 205

Asp Lys Tyr Ile Leu Gln Gly Val Thr Ser Trp Gly Leu Gly Cys Ala
            210                 215                 220

Arg Pro Asn Lys Pro Gly Val Tyr Val Arg Val Ser Arg Phe Val Thr
225                 230                 235                 240

Trp Ile Glu Gly Val Met Arg Asn Asn
```

<210> SEQ ID NO 20
<211> LENGTH: 44
<212> TYPE: DNA
<213> ORGANISM: artificial sequence
<220> FEATURE:
<223> OTHER INFORMATION: oligonucleotide primer

<400> SEQUENCE: 20
gttcggtgct ggtctgttga acaggcaca attacctgtg attg                          44

<210> SEQ ID NO 21
<211> LENGTH: 44
<212> TYPE: DNA
<213> ORGANISM: artificial sequence
<220> FEATURE:
<223> OTHER INFORMATION: oligonucleotide primer

<400> SEQUENCE: 21
caatcacagg taattgtgcc tgtttcaaca gaccagcacc gaac                          44

<210> SEQ ID NO 22
<211> LENGTH: 768
<212> TYPE: DNA
<213> ORGANISM: artificial sequence
<220> FEATURE:
<223> OTHER INFORMATION: E138Q mutant microplasmin
<220> FEATURE:
<221> NAME/KEY: misc_feature
<222> LOCATION: (1)..(6)
<223> OTHER INFORMATION: XhoI restriction site
<220> FEATURE:
<221> NAME/KEY: misc_feature
<222> LOCATION: (7)..(12)
<223> OTHER INFORMATION: encoding KEX2 cleavage site
<220> FEATURE:
<221> NAME/KEY: misc_feature
<222> LOCATION: (763)..(768)
<223> OTHER INFORMATION: XbaI restriction site

<400> SEQUENCE: 22
ctcgagaaaa gagcaccttc attcgactgt ggtaagcctc aggtcgaacc taagaagtgt         60
ccaggtcgtg ttgtcggtgg ctgtgtggct catcctcatt cttggccttg gcaagtgtct        120
cttagaacta gatttggtat gcacttctgt ggtggcacct tgatctcacc tgaatgggtc        180
ttaaccgcag ctcattgtct ggagaagtca ccacgtccat cttcatacaa ggtcatcctt        240
ggcgcacatc aggaagtcaa tcttgagcct catgttcagg agatcgaagt ctctcgtttg        300
ttcttggaac caactcgtaa agacattgct cttctgaagc tgtcatctcc tgccgtgatt        360
accgacaagg taattcctgc ctgcttgcct agtcctaatt acgtcgttgc cgaccgtacc        420
gaatgcttca ttactggttg gggtgagact caaggtacgt tcggtgctgg tctgttgaaa        480
caggcacaat tacctgtgat tgagaacaag gtttgtaaca gatacgagtt cctgaatggt        540
cgtgttcagt ccactgagtt gtgtgcaggt caccttgcag tggtactga tagttgtcaa        600 ggtgattctg gtggaccact ggtgtgcttc gagaaggata agtacatctt acaaggtgtt        660
acgtcttggg gtcttggatg tgctcgtcct aacaagccag gtgtctacgt cagagtctcc        720
agattcgtaa cttggatcga aggtgtcatg cgtaacaact aatctaga                     768

<210> SEQ ID NO 23
<211> LENGTH: 253
<212> TYPE: PRT
<213> ORGANISM: artificial sequence
<220> FEATURE:
<223> OTHER INFORMATION: E138Q mutant microplasmin
<220> FEATURE:
<221> NAME/KEY: MISC_FEATURE
<222> LOCATION: (1)..(2)
<223> OTHER INFORMATION: encoded by XhoI restriction site nucleotides
<220> FEATURE:
<221> NAME/KEY: MISC_FEATURE
<222> LOCATION: (3)..(4)
<223> OTHER INFORMATION: KEX2 cleavage site

<400> SEQUENCE: 23

```
Leu Glu Lys Arg Ala Pro Ser Phe Asp Cys Gly Lys Pro Gln Val Glu
1               5                   10                  15

Pro Lys Lys Cys Pro Gly Arg Val Val Gly Gly Cys Val Ala His Pro
            20                  25                  30

His Ser Trp Pro Trp Gln Val Ser Leu Arg Thr Arg Phe Gly Met His
        35                  40                  45

Phe Cys Gly Gly Thr Leu Ile Ser Pro Glu Trp Val Leu Thr Ala Ala
50                  55                  60

His Cys Leu Glu Lys Ser Pro Arg Pro Ser Ser Tyr Lys Val Ile Leu
65                  70                  75                  80

Gly Ala His Gln Glu Val Asn Leu Glu Pro His Val Gln Glu Ile Glu
                85                  90                  95

Val Ser Arg Leu Phe Leu Glu Pro Thr Arg Lys Asp Ile Ala Leu Leu
            100                 105                 110

Lys Leu Ser Ser Pro Ala Val Ile Thr Asp Lys Val Ile Pro Ala Cys
        115                 120                 125

Leu Pro Ser Pro Asn Tyr Val Val Ala Asp Arg Thr Glu Cys Phe Ile
130                 135                 140

Thr Gly Trp Gly Glu Thr Gln Gly Thr Phe Gly Ala Gly Leu Leu Lys
145                 150                 155                 160

Gln Ala Gln Leu Pro Val Ile Glu Asn Lys Val Cys Asn Arg Tyr Glu
                165                 170                 175

Phe Leu Asn Gly Arg Val Gln Ser Thr Glu Leu Cys Ala Gly His Leu
            180                 185                 190

Ala Gly Gly Thr Asp Ser Cys Gln Gly Asp Ser Gly Gly Pro Leu Val
        195                 200                 205

Cys Phe Glu Lys Asp Lys Tyr Ile Leu Gln Gly Val Thr Ser Trp Gly
210                 215                 220

Leu Gly Cys Ala Arg Pro Asn Lys Pro Gly Val Tyr Val Arg Val Ser
225                 230                 235                 240

Arg Phe Val Thr Trp Ile Glu Gly Val Met Arg Asn Asn
                245                 250
```

<210> SEQ ID NO 24
<211> LENGTH: 768
<212> TYPE: DNA
<213> ORGANISM: artificial sequence
<220> FEATURE:
<223> OTHER INFORMATION: E138Q K147E mutant microplasmin
<220> FEATURE:
<221> NAME/KEY: misc_feature
<222> LOCATION: (1)..(6)
<223> OTHER INFORMATION: XhoI restriction site
<220> FEATURE:
<221> NAME/KEY: misc_feature
<222> LOCATION: (7)..(12)
<223> OTHER INFORMATION: encoding KEX2 cleavage site
<220> FEATURE:
<221> NAME/KEY: misc_feature
<222> LOCATION: (763)..(768)
<223> OTHER INFORMATION: XbaI restriction site

<400> SEQUENCE: 24

```
ctcgagaaaa gagcaccttc attcgactgt ggtaagcctc aggtcgaacc taagaagtgt      60
ccaggtcgtg ttgtcggtgg ctgtgtggct catcctcatt cttggccttg caagtgtct     120 cttagaacta gatttggtat gcacttctgt ggtggcacct tgatctcacc tgaatgggtc    180
ttaaccgcag ctcattgtct ggagaagtca ccacgtccat cttcatacaa ggtcatcctt    240
ggcgcacatc aggaagtcaa tcttgagcct catgttcagg agatcgaagt ctctcgtttg    300
ttcttggaac caactcgtaa agacattgct cttctgaagc tgtcatctcc tgccgtgatt    360
accgacaagg taattcctgc ctgcttgcct agtcctaatt acgtcgttgc cgaccgtacc    420
gaatgcttca ttactggttg gggtgagact caaggtacgt tcggtgctgg tctgttgaaa    480
caggcacaat tacctgtgat tgagaacgaa gtgtgtaaca gatacgagtt cctgaatggt    540
cgtgttcagt ccactgagtt gtgtgcaggt caccttgcag gtggtactga tagttgtcaa    600
ggtgattctg gtggaccact ggtgtgcttc gagaaggata agtacatctt acaaggtgtt    660
acgtcttggg gtcttggatg tgctcgtcct aacaagccag gtgtctacgt cagagtctcc    720
agattcgtaa cttggatcga aggtgtcatg cgtaacaact aatctaga                 768
```

<210> SEQ ID NO 25
<211> LENGTH: 253
<212> TYPE: PRT
<213> ORGANISM: artificial sequence
<220> FEATURE:
<223> OTHER INFORMATION: E138Q K147E mutant microplasmin
<220> FEATURE:
<221> NAME/KEY: MISC_FEATURE
<222> LOCATION: (1)..(2)
<223> OTHER INFORMATION: encoded by XhoI restriction site nucleotides
<220> FEATURE:
<221> NAME/KEY: MISC_FEATURE
<222> LOCATION: (3)..(4)
<223> OTHER INFORMATION: KEX2 cleavage site

<400> SEQUENCE: 25

```
Leu Glu Lys Arg Ala Pro Ser Phe Asp Cys Gly Lys Pro Gln Val Glu
1               5                   10                  15

Pro Lys Lys Cys Pro Gly Arg Val Val Gly Gly Cys Val Ala His Pro
            20                  25                  30

His Ser Trp Pro Trp Gln Val Ser Leu Arg Thr Arg Phe Gly Met His
        35                  40                  45

Phe Cys Gly Gly Thr Leu Ile Ser Pro Glu Trp Val Leu Thr Ala Ala
    50                  55                  60

His Cys Leu Glu Lys Ser Pro Arg Pro Ser Ser Tyr Lys Val Ile Leu
65                  70                  75                  80

Gly Ala His Gln Glu Val Asn Leu Glu Pro His Val Gln Glu Ile Glu
                85                  90                  95

Val Ser Arg Leu Phe Leu Glu Pro Thr Arg Lys Asp Ile Ala Leu Leu
            100                 105                 110

Lys Leu Ser Ser Pro Ala Val Ile Thr Asp Lys Val Ile Pro Ala Cys
        115                 120                 125

Leu Pro Ser Pro Asn Tyr Val Val Ala Asp Arg Thr Glu Cys Phe Ile
    130                 135                 140
```

```
Thr Gly Trp Gly Glu Thr Gln Gly Thr Phe Gly Ala Gly Leu Leu Lys
145                 150                 155                 160

Gln Ala Gln Leu Pro Val Ile Glu Asn Glu Val Cys Asn Arg Tyr Glu
                165                 170                 175

Phe Leu Asn Gly Arg Val Gln Ser Thr Glu Leu Cys Ala Gly His Leu
            180                 185                 190

Ala Gly Gly Thr Asp Ser Cys Gln Gly Asp Ser Gly Gly Pro Leu Val
        195                 200                 205

Cys Phe Glu Lys Asp Lys Tyr Ile Leu Gln Gly Val Thr Ser Trp Gly
    210                 215                 220

Leu Gly Cys Ala Arg Pro Asn Lys Pro Gly Val Tyr Val Arg Val Ser
225                 230                 235                 240

Arg Phe Val Thr Trp Ile Glu Gly Val Met Arg Asn Asn
                245                 250
```

<210> SEQ ID NO 26
<211> LENGTH: 768
<212> TYPE: DNA
<213> ORGANISM: artificial sequence
<220> FEATURE:
<223> OTHER INFORMATION: E138Q K147H R158H mutant microplasmin
<220> FEATURE:
<221> NAME/KEY: misc_feature
<222> LOCATION: (1)..(6)
<223> OTHER INFORMATION: XhoI restriction site
<220> FEATURE:
<221> NAME/KEY: misc_feature
<222> LOCATION: (7)..(12)
<223> OTHER INFORMATION: encoding KEX2 cleavage site
<220> FEATURE:
<221> NAME/KEY: misc_feature
<222> LOCATION: (763)..(768)
<223> OTHER INFORMATION: XbaI restriction site

<400> SEQUENCE: 26

```
ctcgagaaaa gagcaccttc attcgactgt ggtaagcctc aggtcgaacc taagaagtgt      60
ccaggtcgtg ttgtcggtgg ctgtgtggct catcctcatt cttggccttg caagtgtct     120 cttagaacta gatttggtat gcacttctgt ggtggcacct tgatctcacc tgaatgggtc    180
ttaaccgcag ctcattgtct ggagaagtca ccacgtccat cttcatacaa ggtcatcctt    240
ggcgcacatc aggaagtcaa tcttgagcct catgttcagg agatcgaagt ctctcgtttg    300
ttcttggaac caactcgtaa agacattgct cttctgaagc tgtcatctcc tgccgtgatt    360
accgacaagg taattcctgc ctgcttgcct agtcctaatt acgtcgttgc cgaccgtacc    420
gaatgcttca ttactggttg gggtgagact caaggtacgt tcggtgctgg tctgttgaaa    480
caggcacaat tacctgtgat tgagaaccac gtgtgtaaca gatacgagtt cctgaatgga    540
cacgtgcagt ccactgagtt gtgtgcaggt caccttgcag gtggtactga tagttgtcaa    600
ggtgattctg gtggaccact ggtgtgcttc gagaaggata gtacatcatt acaaggtgtt    660
acgtcttggg gtcttggatg tgctcgtcct aacaagccag gtgtctacgt cagagtctcc    720
agattcgtaa cttggatcga aggtgtcatg cgtaacaact aatctaga                  768
```

<210> SEQ ID NO 27
<211> LENGTH: 253
<212> TYPE: PRT
<213> ORGANISM: artificial sequence
<220> FEATURE:
<223> OTHER INFORMATION: E138Q K147H R158H mutant microplasmin

```
<220> FEATURE:
<221> NAME/KEY: MISC_FEATURE
<222> LOCATION: (1)..(2)
<223> OTHER INFORMATION: encoded by XhoI restriction site nucleotides
<220> FEATURE:
<221> NAME/KEY: MISC_FEATURE
<222> LOCATION: (3)..(4)
<223> OTHER INFORMATION: KEX2 cleavage site

<400> SEQUENCE: 27

Leu Glu Lys Arg Ala Pro Ser Phe Asp Cys Gly Lys Pro Gln Val Glu
1               5                   10                  15

Pro Lys Lys Cys Pro Gly Arg Val Val Gly Gly Cys Val Ala His Pro
            20                  25                  30

His Ser Trp Pro Trp Gln Val Ser Leu Arg Thr Arg Phe Gly Met His
        35                  40                  45

Phe Cys Gly Gly Thr Leu Ile Ser Pro Glu Trp Val Leu Thr Ala Ala
    50                  55                  60

His Cys Leu Glu Lys Ser Pro Arg Pro Ser Ser Tyr Lys Val Ile Leu
65                  70                  75                  80

Gly Ala His Gln Glu Val Asn Leu Glu Pro His Val Gln Glu Ile Glu
                85                  90                  95

Val Ser Arg Leu Phe Leu Glu Pro Thr Arg Lys Asp Ile Ala Leu Leu
                100                 105                 110

Lys Leu Ser Ser Pro Ala Val Ile Thr Asp Lys Val Ile Pro Ala Cys
            115                 120                 125

Leu Pro Ser Pro Asn Tyr Val Val Ala Asp Arg Thr Glu Cys Phe Ile
        130                 135                 140

Thr Gly Trp Gly Glu Thr Gln Gly Thr Phe Gly Ala Gly Leu Leu Lys
145                 150                 155                 160

Gln Ala Gln Leu Pro Val Ile Glu Asn His Val Cys Asn Arg Tyr Glu
                165                 170                 175

Phe Leu Asn Gly His Val Gln Ser Thr Glu Leu Cys Ala Gly His Leu
                180                 185                 190

Ala Gly Gly Thr Asp Ser Cys Gln Gly Asp Ser Gly Gly Pro Leu Val
            195                 200                 205

Cys Phe Glu Lys Asp Lys Tyr Ile Leu Gln Gly Val Thr Ser Trp Gly
        210                 215                 220

Leu Gly Cys Ala Arg Pro Asn Lys Pro Gly Val Tyr Val Arg Val Ser
225                 230                 235                 240

Arg Phe Val Thr Trp Ile Glu Gly Val Met Arg Asn Asn
                245                 250
```

PLASMINOGEN AND PLASMIN VARIANTS

CROSS-REFERENCE TO RELATED APPLICATIONS

This application is the National Stage of International Application Serial No. PCT/EP2012/050074, filed on Jan. 4, 2012, which claims the benefit of European Application No. 11150246.4 and U.S. Provisional Application No. 61/429,868, both filed on Jan. 5, 2011. The contents of all of the above-referenced applications are incorporated by reference in their entirety herein.

FIELD OF THE INVENTION

The invention relates to variants of plasminogen and plasmin comprising one or more point mutations in the catalytic domain which reduce or prevent autocatylic destruction of the protease activity of plasmin. Compositions, uses and methods of using said variants of plasminogen and plasmin are also disclosed.

BACKGROUND TO THE INVENTION

Activation of the zymogen plasminogen results in the formation of the fibrinolytically/thrombolytically active serine proteinase plasmin. Activation of endogenous plasminogen can be triggered or enhanced by the administration of a plasminogen activator such as urokinase, streptokinase, staphylokinase or tPA, or any variant thereof. Upon activation, the plasminogen protein is proteolytically cleaved into a heavy chain comprising the 5 kringle domains and a light chain comprising the catalytic domain. Both chains are held together via 2 disulfide bonds. After activation, an autolytic cleavage removes an N-terminal segment from the heavy chain (78 amino acids of human plasmin; 77 amino acids of bovine plasmin) and the bovine plasmin heavy chain can be further autocatalytically cleaved between kringles 3 and 4, hence giving rise to bovine midiplasmin (Christensen et al. 1995, Biochem J 305, 97-102). Activation of plasminogen to plasmin, triggered by the cleavage of the R561-V562 peptide bond in human plasminogen, induces a large conformational change in the light chain, said change resulting in the priming, or activation, of the catalytic triad within said light chain. Bacterial plasminogen activators such as streptokinase and staphylokinase form a complex with plasminogen and, without cleavage of the R561-V562 peptide bond of plasminogen, the catalytic site of plasminogen is activated due to conformational changes upon activator-plasminogen complex formation (plasminogen activation mechanisms are summarized in, e.g., the Introduction section of Terzyan et al. 2004; Proteins 56: 277-284).

Whereas plasminogen activators act as indirect thrombolytic agents, it has alternatively been suggested to use plasmin itself as a direct fibrinolytic/thrombolytic agent. Such direct use is, however, hampered by the fact that plasmin is, like many proteases, subject to autocatalytic proteolytic degradation which follows second order kinetics subject to product inhibition (Jespersen et al. 1986, Thrombosis Research 41, 395-404).

In the early 1960's it was established that plasmin can be stabilized at acidic pH, or alternatively at neutral pH provided an amino acid such as lysine is present. Nevertheless, autolytic cleavage after Lys104, Arg189 and Lys622 (numbering relative to Lys-plasmin) were reported even when plasmin is stored at pH 3.8 (WO 01/36608). When plasmin is stored at the even lower pH of 2.2, non-autolytic acid cleavage occurs between Asp-Pro (D-P) at positions Asp62, Asp154 and Asp346 (WO 01/36608). This illustrates that pH can be lowered to a point where no apparent autocatylic degradation occurs anymore but at which acid hydrolysis is becoming a factor of destabilization. No information is present in WO 01/36608 as to which peptide bonds in plasmin are vulnerable to (autocatalytic) hydrolysis at neutral pH. Known stabilizers of plasmin include glycerol, sufficiently high ionic strength, fibrinogen and ε-aminocaproic acid (EACA), as disclosed by Jespersen et al. (1986, Thromb Res 41, 395-404). Lysine and lysine-derivatives (such as EACA and tranexamic acid) and p-aminomethylbenzoic acid (PAMBA) are some further known stabilizers (Uehsima et al. 1996, Clin Chim Acta 245, 7-18; Verstraete 1985, Drugs 29, 236-261). U.S. Pat. No. 4,462,980 reported on the formation of plasmin aggregates contributing to plasmin degradation despite storage at acidic conditions. A solution to this problem was provided in U.S. Pat. No. 4,462,980 by means of adding a polyhydroxy compound. Other ways of stabilizing plasmin include the addition of oligopeptidic compounds (e.g. U.S. Pat. No. 5,879,923). Alternatively, the catalytic site of plasmin can be reversibly blocked by means of derivatization, e.g. acylation (EP 0009879). Pegylation of plasmin has also been suggested as a means to stabilize the enzyme (WO 93/15189).

A number of plasmin variants other than truncated forms of plasmin have been described and include a chimeric microplasmin (WO 2004/045558) and variants with a point mutation at the two-chain cleavage site (U.S. Pat. No. 5,087,572) or at a catalytic triad amino acid (Mhashilkar et al. 1993, Proc Natl Acad Sci USA 90, 5374-5377; Wang et al., 2001, J Mol Biol 295, 903-914). Wang et al. (1995, Protein Science 4, 1758-1767 and 1768-1779) reported an extensive series of microplasminogen mutants at amino acid positions 545, 548, 550, 555, 556, 558, 560-564, 585, 740 and 788. A double mutant wherein cysteines at amino acid positions 558 and 566 were substituted for serines was reported by Linde et al. (1998, Eur J Biochem 251, 472-479). Takeda-Shitaka et al. (1999, Chem Pharm Bull 47, 322-328) refer to a plasmin variant with reduced activity, the variation involving the substitution of alanine at amino acid position 601 to threonine. All amino acid positions referred to above are relative to Glu-plasminogen starting with Glu at amino acid position 1. A non-cleavable plasminogen variant (cleavage between heavy and light chain impaired) is described in WO 91/08297. Dawson et al. (1994, Biochemistry 33, 12042-12047) describe the reduced affinity for streptokinase of a Glu-plasminogen variant with a Glu instead of Arg at position 719 (R719E). Jespers et al. (1998, Biochemistry 37, 6380-6386) produced in an Ala-scan the series of phage-displayed microplasminogen single-site mutants H569A, R610A, K615A, D660A, Y672A, R712A, R719A, T782A, R789A, and found that arginine at position 719 is key for interaction with staphylokinase; the D660A mutant was not further characterized due to very low expression; only the R719A mutant was additionally produced in soluble form. None of the mutants showed a gross change in proteolytic activity (substrate S-2403). Jespers et al. (1998) also included an active site mutant S741A in their analysis; the crystal structure of this mutant is disclosed in Wang et al. (2000, J Mol Biol 295, 903-914). In further attempts to unravel the streptokinase/plasminogen interaction sites, Terzyan et al. (2004, Proteins 56, 277-284) reported a number of microplasminogen mutants (K698M, D740N, S741A) in an already mutated background (R561A), the latter prohibiting proteolytic activation of plasminogen and thus prohibiting formation of active microplasmin (which would complicate the study of the contact-activation mechanism of the streptokinase-microplasminogen complex). Terzyan et al. (2004) further mention an "inadvertent" triple mutant R561A/H569Y/K698M apparently functionally indifferent from the double mutant R561A/K698M. Wang et al. (2000, Eur J Biochem 267, 3994-4001), in studying streptokinase/plasmin(ogen) interaction, produced a set of microplasminogen (amino acids 530-791 of Glu-plasminogen) mutants in a Cys536Ala and Cys541Ser background. These mutants include the R561A mutation as described above (Terzyan et al. (2004)) as well as R561A/K698G, R561A/K698A and R561A/K698Q double mutants. In the same C536A/C541S background, single K698G and K698A mutations were introduced also, of which the K698G was not characterized further due to difficulties with purification. The above studies aimed at obtaining a better understanding of the characteristics of the plasminogen/plasmin molecule and did not report any clinical usefulness or benefit or putative clinical advantages of the plasminogen/plasmin mutants. Peisach et al. (1999, Biochemistry 38, 11180-11188) succeeded in determining the crystal structure of microplasminogen containing the M585Q, V673M and M788L mutations.

Nguyen & Chrambach (1981, Preparative Biochem 11, 159-172) reported the presence of "a minor and unidentified protein component" of 10.0 kDa based on reducing SDS-PAGE of a crude commercial preparation of urokinase-activated plasmin (Homolysin). The differences in autolysis of human plasmin depending on pH have been described in detail by Shi &Wu (1988, Thrombosis Research 51, 355-364). Ohyama et al. (2004, Eur J Biochem 271, 809-820) proposed the use of non-lysine analog plasminogen modulators in treatment of cancer due to the enhancement of plasmin autoproteolysis by such compounds which results in the enhanced formation of angiostatins (in the presence of the plasminogen activator urokinase). Table 3 of Ohyama et al. (2004) lists as many as 15 cleavage sites within plasmin subjected to autoproteolyis-enhancing compounds. In discussing their observations in view of prior investigations, it would seem that the autoproteolyis-enhancing compounds are more or less selectively enhancing proteolysis of the B/light-chain whereas minimum degradation of both A/heavy- and B-chain was found in the absence of the autoproteolyis-enhancing compounds.

It is clear that none of the above methods/variants solves the problem of providing a plasmin stabilized at the molecular level. The provision of a plasmin variant (or of a corresponding plasminogen variant from which plasmin can be derived) with a catalytic domain intrinsically resistant to autocatalytic degradation would be a significant step forward towards efficient and safe long-term storage as well as towards efficient and safe therapeutic use of plasmin such as in thrombolytic therapy or in the induction of posterior vitreous detachment or vitreous liquefaction in the eye.

SUMMARY OF THE INVENTION

The invention relates to isolated plasminogen variants or plasmins obtained from it, or to isolated plasmin variants, or to proteolytically active or reversible inactive derivatives of any of said plasmins characterized in that:
(i) they comprise in their catalytic domain a lysine or arginine at a position P and the mutation of at least one amino acid at a position [P+/−n], wherein n is 1, 2, 3, 4 or 5, and wherein the amino acid at position [P+/−n] is not a lysine and not an arginine; and
(ii) the mutation of (i) reduces the extent of autoproteolytic degradation of said plasmin variant compared to the extent of autoproteolytic degradation of wild-type plasmin, such as determined with a chromogenic or biological substrate activity assay.

The invention further relates to plasminogen variants, plasmin variants, or plasmin derivatives as described above comprising in their catalytic domain the mutation of at least two internal amino acids:
at positions [P+/−n] and [P+/−n']; wherein n and n' are 1, 2, 3, 4 or 5; wherein the amino acids at positions [P+/−n] and [P+/−n'] are not lysine and not arginine; and wherein n and n' are different from each other if both are either added to or subtracted from P; or
at positions [P+/−n] and [P'+/−n]; wherein P' is the greater value of P and P'; wherein the amino acid at position P' is a lysine or arginine; wherein n is 1, 2, 3, 4 or 5; wherein the amino acid at position [P'+/−n] is not a lysine and not an arginine; and wherein, if present, positions overlapping between [P+n] and [P'−n] are excluded;
and wherein the mutation of said at least two internal amino acids reduces the extent of autoproteolytic degradation of said plasmin variant compared to the extent of autoproteolytic degradation of wild-type plasmin, such as can be determined with a chromogenic or biological substrate activity assay.

Any of the above plasminogen variants, plasmin variants, or plasmin derivatives may further comprise the mutation of any one or more of the lysine or arginine amino acids of the catalytic domain, including the lysine or arginine amino acids at any of the positions P and P', into a non-lysine, non-arginine amino acid.

In any of the above plasminogens, plasmins, or plasmin derivatives a said internal amino acid at position P or P' may in particular be chosen from:
(i) lysine at position 137 of the human plasmin catalytic domain, or the corresponding lysine or arginine of a non-human plasmin catalytic domain;
(ii) lysine at position 147 of the human plasmin catalytic domain, or the corresponding lysine or arginine of a non-human plasmin catalytic domain; or
(iii) arginine at position 158 of the human plasmin catalytic domain, or the corresponding arginine or lysine of a non-human plasmin catalytic domain;
wherein said human plasmin catalytic domain is starting with the amino acid valine at position 1 which is the same valine amino acid occurring at position 562 of human Glu-plasminogen.

In particular, in the plasminogens, plasmins, or plasmin derivatives according to the invention, said amino acid at position [P+/−n] is the amino acid glutamate at position 138 of the human plasmin catalytic domain, or the corresponding amino acid residue of a non-human plasmin catalytic domain.

Any of the plasminogen variants, plasmin variants, or plasmin derivatives according to the invention may be characterized further in that its autolysis constant is at most 95% of the autolysis constant of wildtype plasmin. This feature may also serve as a definition of reduced autoproteolytic degradation of a plasminogen variant or plasmin variant as described above compared to autoproteolytic degradation of the corresponding wild-type plasminogen or plasmin.

Any of the plasminogen variants, plasmin variants, or plasmin derivatives according to the invention may be characterized further in that the catalytic constant $k_{cat}$ is in the range of 10% to 200% of the $k_{cat}$ of wildtype plasmin.

Any of the plasminogen variants, plasmin variants, or plasmin derivatives according to the invention may be characterized further in that its autolysis constant is at most 95% of the autolysis constant of wildtype plasmin and its catalytic constant $k_{cat}$ is in the range of 10% to 200% of the $k_{cat}$ of wildtype plasmin.

Without imposing any limitation, any of the above plasminogen variants, plasmin variants, or plasmin derivatives according to the invention may be one of Glu-plasminogen or Glu-plasmin, Lys-plasminogen or Lys-plasmin, midiplasminogen or midiplasmin, miniplasminogen or miniplasmin, microplasminogen or microplasmin, deltaplasminogen or deltaplasmin.

The invention further relates to the isolated plasminogen variants, plasmin variants, or plasmin derivatives as described above, or a combination of any thereof for use as a medicament.

The invention also relates to compositions comprising an isolated plasminogen variant, plasmin variant, or plasmin derivative as described above, or a combination of any thereof, and at least one of a pharmaceutically acceptable diluent, carrier or adjuvant. Such composition may optionally further comprise at least one of an anticoagulant, a thrombolytic agent, an anti-inflammatory agent, an antiviral agent, an antibacterial agent, an antifungal agent, an anti-angiogenic agent, an anti-mitotic agent, an antihistamine or an anaesthetic.

The invention also includes any beneficial application of an isolated plasminogen variant, plasmin variant, or plasmin derivative as described above. Without imposing any limitation, these include: inducing or promoting lysis of a pathological fibrin deposit in a subject, inducing posterior vitreous detachment in the eye and/or for inducing liquefaction of the vitreous in the eye, facilitating surgical vitrectomy in the eye in a subject, enzymatic debridement of injured tissue of a subject, reducing circulating fibrinogen in a subject, reducing α2-antiplasmin levels in a subject, reducing the risk of pathological fibrin deposition.

The invention further relates to methods for screening for autoproteolytically stable plasmin variants, said methods comprising the steps of:
(i) mutating an amino acid at a position [P+/−n], wherein the amino acid at position P is an arginine or lysine, and wherein n is 1, 2, 3, 4 or 5;
(ii) determining the autoproteolytic stability of the mutant obtained from (i), such as determined with a chromogenic or biological substrate activity assay;
(iii) comparing the autoproteolytic stability of the mutant determined in (ii) with the autoproteolytic stability of wild-type plasmin; and
(iv) selecting from (iii) a mutant that is autoproteolytically more stable than wild-type plasmin as the autoproteolytically stable variant.

In the above method, the amino acid at position [P+/−n] preferably is not a lysine and not an arginine.

In an alternative method for screening for an autoproteolytically stable plasmin variants, said method is comprising the steps of:
(i) mutating the glutamate amino acids at positions 138 of the human plasmin catalytic domain, or of the corresponding amino acid residue of a non-human plasmin, into an amino acid different from the natural amino acid;
(ii) determining the autoproteolytic stability of the mutant obtained from (i), such as determined with a chromogenic or biological substrate activity assay, and
(iii) selecting from (ii) a mutant that is autoproteolytically stable as the autoproteolytically stable plasmin variant;

wherein said human plasmin catalytic domain is starting with the amino acid valine at position 1 which is the same valine amino acid occurring at position 562 of human Glu-plasminogen.

Any of the above screening methods may optionally further comprise a step wherein the proteolytic activity of the autoproteolytically stable plasmin variant is determined.

The invention further includes methods for enhancing long-term storage stability of a plasmin-comprising composition, said methods comprising the step of identifying an autoproteolytically stable plasmin variant capable of being stored over a long time without significant loss of proteolytic activity.

The invention further includes methods for producing a plasminogen variant according to the invention, said methods including the steps of:
(i) introducing a nucleic acid encoding a plasminogen according to the invention in a suitable host cell capable of expressing said plasminogen;
(ii) growing the host cell obtained in (i) under conditions and during a time sufficient for expression of said plasminogen in said host cell; and
(iii) harvesting the plasminogen expressed in (ii).

Such methods may optionally further include a step (iv) wherein the plasminogen harvested in (iii) is purified.

The invention likewise includes methods for producing a plasmin variant according to the invention, said methods including the steps of:
(i) introducing a nucleic acid encoding a plasminogen according to the invention in a suitable host cell capable of expressing said plasminogen;
(ii) growing the host cell obtained in (i) under conditions and during a time sufficient for expression of said plasminogen in said host cell;
(iii) harvesting the plasminogen expressed in (ii);
(iv) activating the plasminogen of (iii) to plasmin.

Such methods may further optionally comprise a step wherein the plasminogen harvested in (iii) is purified prior to activation in (iv). Further, in any method for producing a plasmin variant according to the invention, the active plasmin obtained in (iv) may optionally be purified. Yet further, the active plasmin variant produced according to a method of the invention may optionally be derivatized and/or reversibly inactivated.

Any of the plasminogen variants, plasmin variants, or plasmin derivatives according to the invention is preferentially obtained in free, or soluble, form, e.g. not attached to the surface of a host (such as in phage display).

The invention further relates to isolated nucleic acid sequences encoding a plasminogen variant or plasmin variant according to the invention. Recombinant vectors comprising such nucleic acids are also part of the invention, as are host cells transformed with such nucleic acid or recombinant vector.

FIGURE LEGENDS

FIG. 1. Amino acid sequence with double numbering of the amino acid positions of wild-type human Glu-plasminogen (1 to 791) and of the plasmin catalytic domain (1 to 230, amino acid sequence and numbering in bold). Microplasminogen as used for demonstrating the invention starts at amino acid position 543 (numbering relative to Glu-plasminogen). Kringle domains (as derived from the information included in GenBank accession number AAA36451) are boxed and their amino acid sequences typed alternating in normal and italic letters. The catalytic triad amino acids are circled.

Figure 2C:
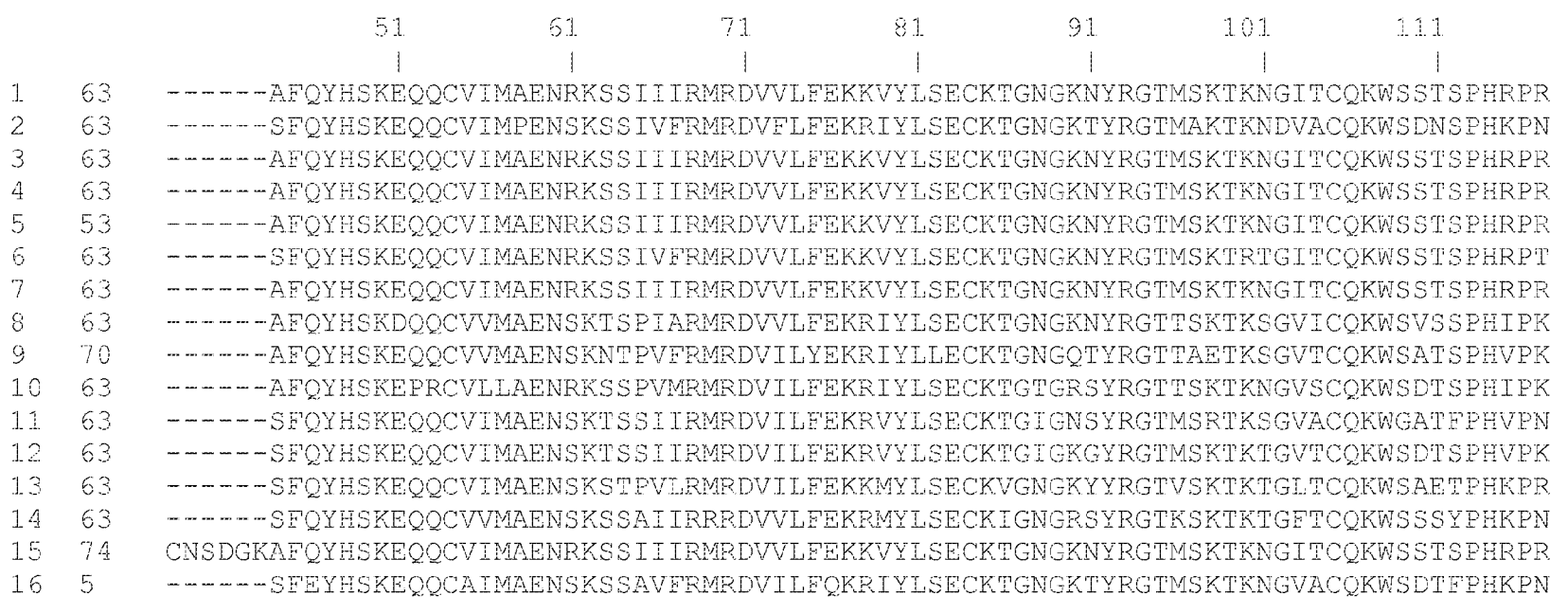

FIGS. 2A-2L. Amino acid sequence alignment of mammalian plasminogen proteins retrieved from GenBank. The sequence alignment was run with the COBALT software (Constraint-based Multiple Alignment Tool; Papadopoulos & Agarwala, Bioinformatics 23:1073-79, 2007) available through the National Center for Biotechnology Information (NCBI) website with default settings. ▼: indication of start of Glu-plasminogen. The amino acid numbering is relative to human plasminogen.

FIG. 3. Reducing SDS-PAGE analysis of exemplary microplasmin variant E138Q. Left lane: molecular weight ladder, with indication of molecular weights. Lane 1: microplasminogen E138Q prior to activation. Lane 2: microplasmin E138Q, same material as in lane 1 but after activation. The gel was stained with Coomassie Brilliant Blue.

DETAILED DESCRIPTION OF THE INVENTION

The current invention is based on the results of studying the mechanisms underlying the unforced auto-inactivation of the proteolytic activity of plasmin at neutral pH, a study for which the inventor chose to focus on microplasmin which consists mainly of the catalytic domain of plasmin. Peptide bonds susceptible to cleavage by plasmin are located at the C-terminus of lysine or arginine (Weinstein & Doolittle, 1972, Biochim Biophys Acta 258, 577-590). Nearly 10% (22 out of 230) of the amino acids of the plasmin catalytic domain (starting at amino acid position 562, a valine, in human Glu-plasminogen) are lysines or arginines. Theoretically all peptide bonds C-terminal of these lysines and arginines, independent of the structure of the amino acid C-terminal of said lysine or arginine, in one plasmin molecule can be proteolytically cleaved by another plasmin molecule. Further theoretically, the mutation of any one or more of these lysines or arginines into a non-lysine non-arginine amino acid would render a plasmin molecule more resistant to autoproteolytic degradation. This theory was proven to be correct, as described in International Patent Application No. PCT/EP2010/059902 (WO 2011/004011). Basis for the current invention is the unexpected observation that mutation of a wild-type amino acid adjacent to a lysine or arginine in the plasmin catalytic domain into a non wild-type amino acid, and this without necessarily mutating the said lysine or arginine, also greatly increases the resistance of the resulting mutant plasmin to autoproteolytic degradation.

One aspect of the invention thus relates to plasmin molecules and to plasminogen molecules, in particular plasminogen molecules that are activatable/can potentially be activated to plasmin, comprising in their catalytic domain one or more mutations of amino acids such that peptide bonds vulnerable to autoproteolytic degradation in wild-type plasmin or plasminogen are less or not vulnerable to autoproteolytic degradation in the plasmin and plasminogen molecules subject of the invention.

The invention in other words relates to isolated plasminogen variants or plasmins obtained from it, or to isolated plasmin variants, or to proteolytically active or reversible inactive derivatives of any of said plasmins characterized in that:
(i) they comprise in their catalytic domain a lysine or arginine at a position P and the mutation of at least one amino acid at position [P+n] or [P−n] (further annotated as [P+/−n]) into a non wild-type amino acid (or into an amino acid different from the natural amino acid or naturally occurring amino acids), wherein n is 1, 2, 3 or 4 and wherein the amino acid at position [P+/−n] is not a lysine and not an arginine; and (ii) the (presence of the) mutation of (i) reduces the extent of (or sensitivity to, or susceptibility to, or vulnerability to) autoproteolytic degradation of said plasmin variant compared to the extent of autoproteolytic degradation of wild-type plasmin, such as can be determined with e.g. a chromogenic or biological substrate activity assay (see further).

The purpose of the invention thus is to provide isolated plasmin variants (such as obtained from a plasminogen variants), or a proteolytically active or reversible inactive derivatives of any of said plasmins, characterized in that said plasmin variants or derivatives thereof have a higher resistance/are more resistant to autoproteolysis compared to wild-type plasmin. Some considerations concerning the determination of autoproteolytic resistance/susceptibility follow further.

A mutation of an amino acid at a given position into a "non wild-type amino acid", or into an "amino acid different from the natural amino acid", is considered to be a change of the amino acid at said given position of a wild-type plasminogen or plasmin into any amino acid different from the wild-type or natural amino acid at that said given position of that said wild-type plasminogen or plasmin. Some considerations concerning the choice of the mutations follow further.

In particular, said internal amino acid at position P is a lysine or arginine. As reference used herein (unless stated otherwise), the catalytic domain of plasmin (also referred to in the literature as "light chain" or "B-chain") will be numbered relative to human plasmin, which is starting with the valine at position P=1 which is the same as the valine at position 562 of human Glu-plasminogen (see FIG. 1). Reference can also be made herein to two different amino acid positions in the plasmin catalytic domain, which are then termed [P+/−n] (with lysine or arginine at position P) and [P'+/−n] (with lysine or arginine at position P'), respectively. For the sake of clarity, the positions P, P', [P+/−n], [P'+/−n], etc., are integers. A position [P+n], [P'+n], etc., has the integer value of P, P', etc. increased with the value of n (with n being 1, 2, 3, 4, or 5); a position [P−n], [P'−n], etc., has the integer value of P, P', etc. decreased with the value of n (with n being 1, 2, 3, 4, or 5); a position [P+/−n], [P'+/−n], etc., has the integer value of P, P', etc. increased (+) or decreased (−) with the value of n (with n being 1, 2, 3, 4, or 5). Thus, if e.g. [P+1]=20, then P=19, and [P−2]=17; or if e.g. P'=49, then [P'−5]=44, and [P'+3]=52. The two different amino acid positions in the plasmin catalytic domain can also be defined as e.g. [P+/−n] and [P+/−n'], wherein both n and n' have the value of 1, 2, 3, 4, or 5; and wherein n and n' differ from each other in case n and n' are both either added (+) or subtracted (−). In the latter case if P is e.g. 19; if n and n' are both to be added, with e.g. n=1 and n'=3; then [P+n]=20 and [P+n']=22. Or if n is to be subtracted and n' to be added, with e.g. n=n'=1, then [P−n]=18 and [P+n']=20.

The invention further relates to plasminogen variants, plasmin variants, or plasmin derivatives as described above comprising in their catalytic domain the mutation into non wild-type amino acids (or into amino acids different from the natural amino acids or from the naturally occurring amino acids) of at least two internal amino acids:
 at positions [P+/−n] and [P+/−n']; wherein n and n' are 1, 2, 3, 4 or 5; wherein the amino acids at positions [P+/−n] and [P+/−n'] are not lysine and not arginine; and wherein n and n' are different from each other if both are either added to or subtracted from P; or
 at positions [P+/−n] and [P'+/−n]; wherein P' is the greater value of P and P'; wherein the amino acid at position P' is a lysine or arginine; wherein n is 1, 2, 3, 4 or 5; wherein the amino acid at position [P'+/−n] is not a lysine and not an arginine; and wherein, if present, positions overlapping between [P+n] and [P'−n] are excluded;
and wherein the (presence of the) mutation of said at least two internal amino acids reduces the extent of autoproteolytic degradation of said plasmin variant compared to the extent of autoproteolytic degradation of wild-type plasmin, such as can be determined with a chromogenic or biological substrate activity assay.

Alternatively, the plasminogen variant, plasmin variant, or plasmin derivative according to the invention thus may comprise in its catalytic domain the mutation of any lysine or arginine at any position, including at one or more of the positions P, P', P''', etc., into a non-lysine, non-arginine amino acid.

A person skilled in the art will be able to decide easily into which other amino acid a wild-type amino acid can be mutated. Such decision may, but must not necessarily imply, criteria such as amino acid size, amino acid charge, amino acid polarity, and/or amino acid hydropathy index (see Table 1). Moreover, the availability of the crystal structure of plasminogen and microplasmin (MMDB ID: 12717; PDB ID: 1DDJ; Wang et al., 2001, J Mol Biol 295, 903-914) is of great value in helping identifying the mutant amino acids such that the resulting mutant plasmin or plasminogen molecule retains proteolytic activity. Furthermore, it can be expected that mutation of a wild-type amino acid at a given position [P+/−n], and optionally additionally at one or more of a given position P, P', P''', etc., into either one of the amino acids of a given group will yield similar results. Based on Table 1, said given groups can be defined as follows:
hydrophobic aliphatic amino acids: Met, Ile, Leu and Val
hydrophobic aromatic amino acids: Phe
hydrophilic acidic amino acids: Asp, Glu, Asn and Gln
hydrophilic basic amino acids: Arg, Lys and His
moderately hydrophobic aliphatic amino acids: Gly, Ala, Ser, Thr, Cys, Pro
moderately hydrophobic aromatic amino acids: Tyr and Trp.

Of these, and for the purpose of mutation, Cys and Pro may be less favorable substitute amino acids of wild-type plasmin or plasminogen amino acids due to the creation of possible free thiol-group by a Cys, or due to more extensive disturbance of the protein structure by a Pro. Other amino acid substitutions include the mutation of a wild-type amino acid at a position [P+/−n], and optionally additionally at one or more of a position P, P', P''', etc., of a plasmin(ogen) catalytic domain into a non-natural or noncanonical amino acid, or into amino acid analogs, such as norleucine, norvaline, ornithine or citrulline (for more extensive list see, e.g., Hendrickson et al. 2004, Annu Rev Biochem 73, 147-176).

TABLE 1

Characteristics of amino acids.

| Amino Acid | | | Side chain polarity | Side chain charge (at pH 7) | Hydropathy index |
| --- | --- | --- | --- | --- | --- |
| Alanine | Ala | A | nonpolar | neutral | 1.8 |
| Arginine | Arg | R | polar | positive | −4.5 |
| Asparagine | Asn | N | polar | neutral | −3.5 |
| Aspartic acid | Asp | D | polar | negative | −3.5 |
| Cysteine | Cys | C | nonpolar | neutral | 2.5 |
| Glutamic acid | Glu | E | polar | negative | −3.5 |
| Glutamine | Gln | Q | polar | neutral | −3.5 |
| Glycine | Gly | G | nonpolar | neutral | −0.4 |
| Histidine | His | H | polar | positive | −3.2 |
| Isoleucine | Ile | I | nonpolar | neutral | 4.5 |
| Leucine | Leu | L | nonpolar | neutral | 3.8 |

TABLE 1-continued

Characteristics of amino acids.

| Amino Acid | | | Side chain polarity | Side chain charge (at pH 7) | Hydropathy index |
| --- | --- | --- | --- | --- | --- |
| Lysine | Lys | K | polar | positive | −3.9 |
| Methionine | Met | M | nonpolar | neutral | 1.9 |
| Phenylalanine | Phe | F | nonpolar | neutral | 2.8 |
| Proline | Pro | P | nonpolar | neutral | −1.6 |
| Serine | Ser | S | polar | neutral | −0.8 |
| Threonine | Thr | T | polar | neutral | −0.7 |
| Tryptophan | Trp | W | nonpolar | neutral | −0.9 |
| Tyrosine | Tyr | Y | polar | neutral | −1.3 |
| Valine | Val | V | nonpolar | neutral | 4.2 |

Under the test conditions (unforced autoproteolytic degradation at neutral pH) as described in International Patent Application No. PCT/EP2010/059902, a limited number of autoproteolytic cleavages occur within the plasmin catalytic domain. These cleavages occurred at lysine 137 of human plasmin catalytic domain, at lysine 147 of the human plasmin catalytic domain and at arginine 158 of the human plasmin catalytic domain. This, however, does not exclude the possibility for the existence of other peptide bonds that are autoproteolytically scissile.

Thus, in relation to the plasminogen variants, plasmin variants, or plasmin derivates according to the invention, said internal amino acid at position P or P' may be chosen from:
(i) lysine at position 137 of the human plasmin catalytic domain, or the corresponding lysine or arginine of a non-human plasmin;
(ii) lysine at position 147 of the human plasmin catalytic domain, or the corresponding lysine or arginine of a non-human plasmin; and/or
(iii) arginine at position 158 of the human plasmin catalytic domain, or the corresponding lysine or arginine of a non-human plasmin;
wherein said human plasmin catalytic domain is starting with the amino acid valine at position 1 which is the same valine amino acid occurring at position 562 of human Glu-plasminogen. To clarify the amino acid numbering in human plasminogen and the human plasmin catalytic domain, reference is made to FIG. 1 herein.

In particular, in the above, said at least one internal amino acid at position P is lysine at position 137 of the human plasmin catalytic domain, or the corresponding lysine or arginine of a non-human plasmin, and said internal amino acid at position [P+/−n] is the amino acid at position [P+1], i.e. the glutamate at position 138 of the human plasmin catalytic domain, or the corresponding amino acid residue of a non-human plasmin. Furthermore particular, the said glutamate is mutated into another hydrophilic acidic amino acid, e.g., aspartate, asparagine or glutamine.

The identification of an amino acid in a non-human plasmin(ogen) sequence which "corresponds to" (i.e. the identification of a "corresponding" amino acid) an amino acid in the human plasmin(ogen) first implies the alignment of both amino acid sequences. Such alignment may require some optimization, such as introduction of minor gaps in one or both of the aligned sequences, to result in the highest identity and homology. Secondly, the amino acid in the non-human plasmin(ogen) aligning with the amino acid in the human plasmin(ogen) is identified and is herein referred to as the "corresponding" amino acid. FIGS. 2A-2L herein depict such an alignment of publicly available mammalian plasminogen protein sequences, and highlight the amino acids of particular interest to the current invention in the human plasminogen sequence (line 1) together with the corresponding amino acids in the non-human plasminogen sequences (lines 2-18). The amino acids P, P', etc., of particular interest are Lys at position 698 (position 137 in the catalytic domain, see FIG. 1), Lys at position 708 (position 147 in the catalytic domain, see FIG. 1) and Arg at position 719 (position 158 in the catalytic domain, see FIG. 1).

"Plasmin", also known as fibrinolysin or lysofibrin, is a serine-type protease which results from the activation of the zymogen plasminogen. Activation is the result of a proteolytic cleavage between amino acids 561 and 562 (numbering relative to human Glu-plasminogen). Plasmin carries a heavy chain comprising 5 kringle domains and a light chain comprising the catalytic domain. Plasminogen can be enriched from blood plasma, e.g., via lysine affinity-chromatography (Deutsch & Mertz, 1970, Science 170, 1095-1096). Truncation of the plasmin molecule (outside and/or inside the plasmin catalytic domain) is possible as long as the catalytic domain remains functional, such truncation thus results in the formation of a "proteolytically active derivative" of plasmin. As such, one or more of the 5 kringle domains can be deleted wholly or partially. Truncated plasmins lacking one or more kringle domains and/or lacking parts of one or more kringle domains therefore are envisaged by the current invention as examples of proteolytically active derivatives of plasmin. Examples of truncated variants of plasmin include, but are not limited to, "midiplasmin", "miniplasmin", "microplasmin", and "delta-plasmin". Midiplasmin is basically lacking kringle domains 1 to 3 (e.g. Christensen et al., 1995, Biochem J 305, 97-102). Miniplasmin was originally obtained by limited digestion of plasmin with elastase and is basically lacking kringle domains 1 to 4 (e.g. Christensen et al., 1979, Biochim Biophys Acta 567, 472-481; Powell & Castellino, 1980, J Biol Chem 255, 5329). Miniplasmin has subsequently been produced recombinantly (WO 2002/050290). Microplasmin was originally obtained by incubation of plasmin at elevated pH and is basically lacking all kringle domains (e.g. WO 89/01336). Whereas the microplasmin obtained from incubation of plasmin at elevated pH is containing the 30-31 carboxy-terminal amino acids of the heavy chain, a recombinantly produced microplasmin variant is containing the 19 carboxy-terminal amino acids of the heavy chain (WO 2002/050290). This illustrates the allowed molecular variability within a given plasmin genus such as the microplasmin genus (e.g. multiple species form the microplasmin genus). Delta-plasmin is a recombinant version of plasmin in which kringle domain 1 or kringle domain 4 is linked directly with the catalytic domain (WO 2005/105990). The above described truncated variants of plasmin are obtained by activation of "midiplasminogen", "miniplasminogen", "microplasminogen" and "delta-plasminogen", respectively. In order to be activatable, a truncated plasminogen needs to comprise a minimum number of amino acids of the linker between the kringle domain (such as kringle 5 domain in miniplasmin) and the catalytic domain, or C-terminal of the catalytic domain in case of a kringle-less truncated plasmin (see, e.g., Wang et al., 1995, Protein Science 4, 1758-1767). In the context of the present invention it may be desired that the plasminogen comprises an "intact activation site", which implies that at least amino acids 561 and 562 (relative to human Glu-plasminogen; or the corresponding amino acids in non-human plasminogen) are present and are present in a molecular context such that activation/conversion of plasminogen to plasmin can occur, albeit possibly with different kinetics, as it occurs in wild-type plasmin. As alternative to plasmin or an active truncated variant thereof, an activatable plasminogen or a truncated variant thereof can be used in the context of the current invention (see, e.g. EP 0480906; U.S. Pat. No. 5,304,383; EP 0631786; U.S. Pat. Nos. 5,520,912; 5,597,800; 5,776,452). "Plasminogen" refers to any form of plasminogen e.g. Glu-plasminogen or Lys-plasminogen (starting with Arg at position 68 or Lys at positions 77 or 78). When using activatable plasminogen or an activatable truncated variant thereof, the activation to plasmin may be delayed and will typically occur after contacting it with an organ, tissue or body fluid, i.e. after administration to a subject. In yet another alternative, the plasmin or an active truncated variant thereof can be substituted in the context of the current invention for an activatable plasminogen or an activatable truncated variant thereof in conjunction with a plasminogen activator (such as tissue plasminogen activator (tPA), urokinase, streptokinase or staphylokinase, or any variant thereof; see, e.g. U.S. Pat. Nos. 6,733,750; 6,585,972; 6,899,877; WO 03/33019). In yet a further alternative, a mixture of any of (i) plasmin or derivative thereof, (ii) activatable plasminogen or an activatable derivative thereof, and, optionally (iii) a plasminogen activator can be used in the context of the current invention (see, e.g. US 2004/0081643). In order to ensure stability of the plasmin (or plasminogen), it will generally be stored at lowered temperatures (e.g. +4 degrees Celsius or −20 degrees Celsius). The storage composition may be a stabilizing composition such as a low pH composition (pH 4 or lower; obtained by e.g. 1 mM to 250 mM of an acid such as citric acid, see, e.g. Castellino & Sodetz, 1976, Methods Enzymol 45, 273-286; WO 01/36608; WO 01/36609; WO 01/36611) or a high glycerol content composition (30-50% v/v, e.g., Castellino & Sodetz, 1976, Methods Enzymol 45, 273-286), alternatively in or in conjunction with one or more further stabilizer compositions comprising e.g. an amino acid (e.g. lysine or an analogue thereof such as EACA or tranexamic acid), a sugar (e.g. mannitol) or any stabilizer as known in the art (e.g. dipeptides, WO 97/01631). Further included in the genus "plasmin" is any active derivative thereof (or of an active truncated plasmin variant), or similar derivative of activatable plasminogen (or of activatable truncated variant thereof). Such derivates include e.g. labeled plasmin or plasminogen (or truncated variants thereof) such as $Tc^{99}$-labeled plasmin (Deacon et al., 1980, Br J Radiol 53, 673-677) or pegylated or acylated plasmin or plasminogen (or truncated variants thereof; EP 9879, WO 93/15189). Any other label (radioactive, fluorescent, etc.) may also be used to produce a plasmin or plasminogen derivative. Said derivatives further include hybrid or chimeric plasmin or plasminogen molecules comprising e.g. a truncated plasmin or plasminogen according to the invention fused with e.g. a fibrin-binding molecule (such as kringle 2 of tPA, an apolipoprotein kringle, the finger domain of tPA or fibronectin or the Fab domain of a fibrin-binding antibody).

Comparison of the autoproteolytic resistance (i.e. stability) of wild-type plasmin and of plasmin variants or plasmin derivatives according to the invention can be performed in a similar way as as for comparing proteolytic activity, e.g., in a chromogenic activity assay or a biological substrate assay based on e.g. fibrin, fibrinogen, fibronectin, gelatin, laminin or collagen.

In order to determine autoproteolytic resistance, the autolysis rate constant can be determined. It is envisaged that the plasmin variants according to the invention, including the plasmins obtained from the plasminogen variants according to the invention, or any of the plasmin derivatives according to the invention may be characterized by an autolysis rate constant that is at least 5%, or at least 10%, 15%, 20%, 25%, 30%, 35%, 40%, 45%, 50%, 60%, 70%, 75%, 80%, 90%, 95%, 99% or 99.5% lower than the autolysis rate constant of wildtype plasmin, or, alternatively, by an autolysis rate constant that is at most 95%, or at most 0.5%, 1%, 5%, 10%, 15%, 20%, 25%, 30%, 35%, 40%, 45%, 50%, 60%, 70%, 75%, 80%, or 90% of the autolysis rate constant of wild-type plasmin. In order to determine the indicated percentage, the calculation can be done based on the absolute autolysis rate constant numbers. For example, an autolysis rate constant of 123 $M^{-1}s^{-1}$ was determined for wild-type microplasmin, whereas for the microplasmin variant E138Q an autolysis rate constant of 4 $M^{-1}s^{-1}$ was determined (see Example 1/Table 2). The autolysis rate constant of the E138Q variant therefore is 3.25% of the autolysis rate constant of wild-type microplasmin.

Further, any of the plasmin variants according to the invention, including the plasmins obtained from the plasminogen variants according to the invention, or derivatives of any of said plasmins may retain proteolytic activity different (higher or lower) from the proteolytic activity of wild-type plasmin, such as determined with e.g. a chromogenic activity assay or a biological substrate assay based on e.g. fibrin, fibrinogen, fibronectin, gelatin, laminin or collagen.

The proteolytic activities of the plasmin variants according to the invention, including the plasmins obtained from the plasminogen variants according to the invention, or any of the plasmin derivatives according to the invention may be compared to the proteolytic activity of wild-type plasmin by means of the catalytic constant $k_{cat}$ which is a measure of the number of substrate molecule each enzyme site converts to product per unit time. Thus, any of the plasmin variants according to the invention, including the plasmins obtained from the plasminogen variants according to the invention, or any of the plasmin derivatives according to the invention may be characterized by a $k_{cat}$ value which is in the range of +100% to −90%, or +50% to −50% of the $k_{cat}$ value of wild-type plasmin, i.e., characterized by a $k_{cat}$ value in the range of 10% to 200%, or 50% to 150% of the $k_{cat}$ value of wild-type plasmin. In order to determine the indicated percentage, the calculation is done on the absolute $k_{cat}$ numbers. For example, wild-type microplasmin has a $k_{cat}$ of 46 $s^{-1}$, whereas the microplasmin variant K137M has a $k_{cat}$ of $36s^{-1}$ (see Example 4/Table 3 of International Patent Application No. PCT/EP2010/059902). The $k_{cat}$ of the K137M variant therefore is 78.3% of the $k_{cat}$ of wild-type microplasmin.

Another way of comparing proteolytic activity of the plasmin variants according to the invention, including the plasmins obtained from the plasminogen variants according to the invention, or any of the plasmin derivatives according to the invention to proteolytic activity of wild-type plasmin includes comparing $k_{cat}/K_m$. Although higher, comparable or slightly lower $k_{cat}/K_m$ values may be preferred, an up to 1000-times or up to 500-times lower $k_{cat}/K_m$ of a plasmin variants according to the invention, including the plasmins obtained from the plasminogen variants according to the invention, or any of the plasmin derivatives according to the invention compared to the $k_{cat}/K_m$ of wild-type plasmin can still be acceptable (see further). By way of example, the $k_{cat}/K_m$ of the E138Q microplasmin variant was determined to be $9.5 \times 10^5$ whereas the $k_{cat}/K_m$ of wild-type plasmin was determined to be $6.9 \times 10^5$ (see Example 1/Table 2), i.e. the $k_{cat}/K_m$ value of E138Q microplasmin is 1.38 times higher than the $k_{cat}/K_m$ value of wild-type microplasmin.

Alternatively, any of the plasmin variants according to the invention, including the plasmins obtained from the plasminogen variants according to the invention, or any of the plasmin derivatives according to the invention may be compared to wild-type plasmin by combining autolytic rate constant data and $k_{cat}/K_m$ data. For example, a plasmin variant with a 20-times lower autolytic rate constant compared to wild-type plasmin, and with a 10-times lower $k_{cat}/K_m$ compared to wild-type plasmin will be 2-times better than the wild-type plasmin. Obviously depending on the ultimate use, a very stable plasmin (i.e. no or nearly no autoproteolytic degradation) with low proteolytic activity may be highly desired, e.g., in cases where low but prolonged plasmin activity is desired or even required to achieve the intended clinical effect. Such highly stable plasmin variants with low proteolytic activity would as such virtually equal slow-release formulations without the real need to actually use a slow-release carrier or adjuvant.

Yet another alternative to compare any of the plasmin variants according to the invention, including the plasmins obtained from the plasminogen variants according to the invention, or any of the plasmin derivatives according to the invention may be compared to wild-type plasmin by combining autolytic rate constant data and $k_{cat}$ data.

Further, any of the plasmin variants according to the invention, including the plasmins obtained from the plasminogen variants according to the invention, or any of the plasmin derivatives according to the invention may be characterized by any combination of the above-defined autolysis rate constant, catalytic constant $k_{cat}$ and/or $k_{cat}/K_m$.

Obviously, for any comparative measurements such as described above it is desirable to compare plasmin variants with their closest wild-type plasmin, e.g., to compare a microplasmin variant with wild-type microplasmin, or a miniplasmin variant with wild-type miniplasmin. Furthermore obvious, for any activity measurement, a reversibly inactivated derivative of a plasmin variant according to the invention should first be activated by removing the cause of reversible inactivation (e.g. acylation or non-optimal pH).

Any of the plasminogen variants according to the invention or plasmins obtained therefrom, of the plasmin variants according to the invention may be Glu-plasminogen of Glu-plasmin, Lys-plasminogen or Lys-plasmin, midiplasminogen or midiplasmin, miniplasminogen or miniplasmin, microplasminogen or microplasmin, deltaplasminogen or deltaplasmin.

Many assays exist to determine whether or not a plasmin species is proteolytically active. Easy and straightforward assays are based on the digestion of a chromogenic substrate by plasmin present in a sample; chromogenic substrates include S-2403 (Glu-Phe-Lys-pNA) and S-2251 (Val-Leu-Lys-pNA) which release p-nitroaniline (pNA) upon proteolytic cleavage. The amount of pNA formed can be measured by light absorbance at 405 nm. An alternative assay for determining plasmin activity is a potentiometric assay. Colorimetric (using a chromogenic substrate) and potentiometric assays are described in e.g., Castellino & Sodetz (1976, Methods Enzymol 45, 273-286). A further alternative assay for determining plasmin activity is a caseinolytic assay (e.g., Robbins & Summaria, 1970, Methods Enzymol 19, 184-199; Ruyssen & Lauwers, 1978, Chapter IX—Plasmin, In "Pharmaceutical Enzymes", Story-Scientia, Gent, Belgium, pp. 123-131). Yet another alternative assay for determining plasmin activity is a fibrinolytic assay (e.g., Astrup & Mullertz, 1952, Arch Biochem Biophys 40, 346-351). Further activity assays could be easily designed using other protein substrates. Clearly, such assays may also be used to follow disappearance of plasmin proteolytic activity over time due to autoproteolytic degradation of the enzyme. As an alternative for assessing stability of a plasmin variant or any active truncated variant or derivative thereof of the current invention, said plasmin variant may be incubated in the presence of wild-type plasmin and the resistance of the plasmin variant to digestion by wild-type plasmin can be monitored.

The use of plasmin in the removal of necrotic elements or debris from lesions, wounds, ulcerating wounds (such as ulcerating stitched wounds) etc. has been described in e.g. U.S. Pat. No. 3,208,908. Similarly, topical application of plasmin-comprising therapeutic preparations for the treatment of burns was disclosed in e.g. U.S. Pat. No. 4,122,158. Debridement refers to the removal of dead, damaged and/or infected tissue in order to improve or increase the healing of remaining healthy tissue. Such removal may be obtained by surgical, mechanical or chemical means, or by means of certain species of live maggots that selectively eat necrotic tissue (maggot therapy). Debridement may also be performed using enzymes or may be assisted by enzymes, a process referred to as enzymatic debridement. Debridement is an important aspect in the healing process of burns and other serious wounds and it is used as well in the treatment of some types of snake bites. The application of plasmin (or of any variant or derivative thereof or alternative therefore as described above) in enzymatic debridement (alone or in combination with other types of debridement) is particularly useful in promoting or facilitating wound healing and as an adjunct in surgical procedures such as skin grafting.

A more commonly known use of plasmin (or of any variant or derivative thereof or alternative therefore as described above) relates in general terms to the treatment of (a) pathological deposit(s) of fibrin. Fibrin deposits can result from a wide variety of pathological situations in the body. For example, fibrin-containing blood clots can form in vessels in tissue resulting in deep vein, coronary artery, cerebral artery or retinal vein occlusion or thrombosis. Small accumulations of fibrin precede, and may provide, warning of impending catastrophic thrombosis. Examples include unstable angina pectoris, which is considered a warning of impending coronary thrombosis and transient ischemic attacks, which may precede strokes. Fibrin is furthermore frequently deposited in tissue in association with inflammation associated with many disease processes including infection, autoimmune disease and cancer. Another situation where fibrin is deposited is around abscesses caused by infection with microorganisms. Fibrin deposits are furthermore frequently found associated with certain solid tumors. Fibrin deposition may also occur during the healing of any type of wound, including those resulting from surgical intervention, including e.g. trabeculectomy. Yet another situation of fibrin deposition is the accumulation of fibrin in a retinal vein, which can lead to retinal degeneration, disturbed vision or even loss of vision. The term pathological fibrin deposit further encompasses such deposits as formed or as present in or at the tip of a catheter, catheter device or other implant such as prosthetic vessels and grafts of synthetic, human or animal origin and effectively blocked by an occlusion comprising fibrin. The term "catheter device" refers to any catheter or tube-like device that may enter the body, including arterial catheters, cardiac catheters, central venous catheters, intravenous catheters, peripherally inserted central catheters, pulmonary artery catheters, tunneled central venous catheters and arterio-venous shunts.

Among the various factors encouraging the process of thrombosis, i.e. the formation of a thrombus or hemostatic plug, are: (1) damage to the endothelial cell lining of the affected blood vessel, (2) an increase in the clotting properties of the blood, and (3) stagnation of blood in the affected blood vessel. Thrombosis can start as a very small lump attached to the damaged part of the blood vessel lining. Its presence encourages further thrombosis to occur, and has the effect of causing a slow-down of blood flow by reducing the inner diameter of the vessel. Further growth of the initially small thrombus often leads to total or almost total blockage of the affected blood vessel. If thrombosis takes place in one of the arteries, the tissues supplied by that artery may be deprived of oxygen and nutrition, causing damage or death of the tissue (gangrene). The severity of the damage depends upon the position and size of the thrombosis, the speed at which it grows and whether the affected area has only one artery or is supplied by collateral blood vessels. If the vessel to a vital organ is affected, e.g. the heart or the brain, the person may be severely crippled or die. Sometimes a thrombus may contain infective organisms such as bacteria, and septic thrombosis may occur, with the formation of pus and infection of the surrounding tissues.

Further uses of plasmin (or of any variant or derivative thereof or alternative therefore as described above) include the reduction of the level of circulating fibrinogen (e.g. WO 93/07893) and its use as an α2-antiplasmin inhibitor (reported to reduce the size of cerebral infarct after ischemic stroke; WO 00/18436).

Yet another use of plasmin (or of any variant or derivative thereof or alternative therefore as described above) is related to the induction of posterior vitreous detachment (PVD) and/or vitreous liquefaction in the eye as an alternative for or as adjunct to mechanical vitrectomy (WO 2004/052228; U.S. Pat. Nos. 6,733,750; 6,585,972; 6,899,877; WO 03/33019; WO 2006/122249; WO 2007/047874; U.S. Pat. Nos. 5,304, 118; US 2006/0024349; US 2003/0147877). Vitrectomy and/or vitreous liquefaction is of benefit for a number of eye conditions such as vitreous floaters (motile debris/deposits of vitreous within the normally transparent vitreous humour which can impair vision), retinal detachment (a blinding condition which may be caused by vitreal traction), macular pucker (scar tissue on macula; macula is required for sharp, central vision; macular pucker is also known as epi- or pre-retinal membrane, cellophane maculopathy, retina wrinkle, surface wrinkling retinopathy, premacular fibrosis, or internal limiting membrane disease), diabetic retinopathy (proliferative or non-proliferative) which may result in vitreal hemorrhage and/or formation of fibrous scar tissue on the retina (which may cause retinal detachment), macular holes (hole in macula causing a blind spot and caused by vitreal traction, injury or a traumatic event), vitreous hemorrhage (caused by diabetic retinopathy, injuries, retinal detachment or retinal tears, subarachnoidal bleedings (Terson syndrome), or blocked vessels), subhyaloid hemorrhage (bleeding under the hyaloid membrane enveloping the vitreous), macular edema (deposition of fluid and protein on or under the macula of the eye) and macular degeneration (starting with the formation of drusen; occurs in dry and wet form; if correlated with age coined age-related macular degeneration). Other eye-applications of plasmin include the maintenance or rescue of a filtering bleb after trabeculectomy surgery (performed to reduce intra-ocular pressure), see e.g. WO 2011/023805.

Another further use of plasmin (or of any variant or derivative thereof or alternative therefore as described above) resides in diagnosis, more particularly appropriately labeled (e.g. Tc$^{99}$-labeled, see above) plasmin (or any variant or derivative thereof or alternative therefore as described above) may be applied for detecting pathological fibrin deposits. When applying a truncated plasmin or plasminogen variant according to the current invention in such diagnosis, care should be taken that said variant still comprises a fibrin-binding site (whether or not from plasmin itself or added to e.g. the plasmin catalytic domain by creating a hybrid molecule).

The plasmin or any variant or derivative thereof or alternative therefore according to the invention may be stored in a pharmaceutically acceptable carrier, diluent or adjuvant. Such carrier, diluent or adjuvant may consist of or comprise an acidic low buffer such as 1-100 mM acetate or citrate. When acidic, the pharmaceutically acceptable carrier, diluent or adjuvant may have a pH of 2.5 to 5.0, such as at pH of 2.5 to 4.0, or such as at a pH of 3.0 to 3.5, or such as a pH of 3.1 or 3.2 or 3.3 or 3.4. Useful acidic compounds include acetic acid, citric acid, hydrochloric acid, lactic acid, malic acid, tartaric acid or benzoic acid. Formic acid may be used but care should be taken that this compound is not inducing proteolytic cleavage at the C-terminus of Asp-residues. The pharmaceutically acceptable carrier, diluent or adjuvant, when either acidic, neutral or basic, may comprise one or more amino acids such as serine, threonine, methionine, glutamine, glycine, isoleucine, valine, alanine, aspartic acid, lysine, histidine or any derivatives or analogues thereof. The pharmaceutically acceptable carrier, diluent or adjuvant may comprise a carbohydrate such as a monosaccharide, disaccharide, polysaccharide or polyhydric alcohol. Examples include sugars such as sucrose, glucose, fructose, lactose, trehalose, maltose and mannose, sugar alcohols such as sorbitol and mannitol and polysaccharides such as dextrins, dextrans, glycogen, starches and celluloses. The pharmaceutically acceptable carrier, diluent or adjuvant may comprise compounds such as glycerol, niacinamide, glucosamine, thiamine, citrulline, inorganic salts (such as sodium chloride, potassium chloride, magnesium chloride, calcium chloride), benzyl alcohol or benzoic acid. The pharmaceutically acceptable carrier, diluents or adjuvant may comprise compounds such as c-aminocaproic acid (EACA) and/or tranexamic acid (see also above & Background section). Some of these compounds may be used as stabilizer of a plasmin or any variant or derivative thereof or alternative therefore as described above.

In view of the above, another aspect of the invention relates to the isolated plasminogen, plasmin, or any variant or derivative thereof or alternative therefore according to the invention, or a combination of any thereof for use as a medicament.

A further aspect of the invention relates to compositions comprising the isolated plasminogen, plasmin, or any variant or derivative thereof or alternative therefore according to the invention, or a combination of any thereof, and at least one of a pharmaceutically acceptable diluent, carrier or adjuvant. In a further embodiment, said composition may additionally comprise at least one of an anticoagulant, a further thrombolytic agent, an anti-inflammatory agent, an antiviral agent, an antibacterial agent, an antifungal agent, an anti-angiogenic agent, an anti-mitotic agent, an antihistamine or an anaesthetic.

In an embodiment to the above-described two aspects of the invention, the isolated plasminogen, plasmin, or any variant or derivative thereof or alternative therefore according to the invention, or of a combination of any thereof, or the composition according to the invention may be used in any clinically relevant setting such as for treating a pathological fibrin deposit, for inducing posterior vitreous detachment in the eye, for inducing liquefaction of the vitreous in the eye, as adjunct to and facilitating vitrectomy in the eye, for inducing posterior vitreous detachment, for resolving vitreomacular adhesion, for closing macular holes, for enzymatic debridement, for reducing circulating fibrinogen, for reducing α2-antiplasmin levels, or in conjunction with trabeculectomy.

In another embodiment to the above-described two aspects of the invention, the isolated plasminogen, plasmin, or any variant or derivative thereof or alternative therefore according to the invention, or of a combination of any thereof, or the composition according to the invention may be used for prophylactic purposes or in methods for prophylactic treatment. Prophylactic uses include reducing the risk of development of a pathological fibrin deposit in a mammal having an increased risk of developing it (such as an obese mammal, a mammal not doing sufficient physical exercise or a mammal scheduled to undergo a major surgical event or operation). Other prophylactic uses include the induction of posterior vitreous detachment and/or vitreous liquefaction in an apparent healthy eye of a mammal of which the companion eye is/was diagnosed to require induction of posterior vitreous detachment and/or vitreous liquefaction.

Alternatively, the invention relates to methods for treating, dissolving, loosening, macerating, lysing, inducing or promoting lysis of a pathological fibrin deposit in a subject, said methods comprising contacting said fibrin deposit with an effective amount of the isolated plasminogen, plasmin, or any variant or derivative thereof or alternative therefore according to the invention, or of a combination of any thereof, said contacting resulting in the treatment, dissolution, loosening, maceration, lysis, or induction or promotion of lysis of said pathological fibrin deposit.

The invention further relates to methods for inducing posterior vitreous detachment in the eye and/or for inducing liquefaction of the vitreous in the eye, or for facilitating surgical vitrectomy in the eye in a subject, said methods comprising contacting an eye of said subject in need of such treatment with an effective amount of the isolated plasminogen, plasmin, or any variant or derivative thereof or alternative therefore according to the invention or of a combination of any thereof, said contacting resulting in the induction of said posterior vitreous detachment and/or of said liquefaction of the vitreous, or in the facilitation of said surgical vitrectomy.

The invention also relates to methods for enzymatic debridement of injured tissue of a subject, said method comprising contacting said injured tissue with an effective amount of the isolated plasminogen, plasmin, or any variant or derivative thereof or alternative therefore according to the invention, or of a combination of any thereof, said contacting resulting in said enzymatic debridement of said injured tissue.

Other methods of the invention are treating or preventing any other clinically relevant indication, including methods for reducing circulating fibrinogen, or for reducing α2-antiplasmin levels in a subject, said methods comprising contacting a subject in need of such treatment with an effective amount of the isolated plasminogen, plasmin, or any variant or derivative thereof or alternative therefore according to the invention, or of a combination of any thereof, said contacting resulting in said reduction of circulating fibrinogen or of said α2-antiplasmin levels.

In general, the medicament or composition of the invention comprising a plasmin (or any variant or derivative thereof or alternative therefore) according to the invention may, depending on its ultimate use and mode of administration, comprise one or more further active ingredients such as an anticoagulant, a further thrombolytic agent, an anti-inflammatory agent, an antiviral agent, an antibacterial agent, an antifungal agent, an anti-angiogenic agent, an anti-mitotic agent, an antihistamine or anesthetic.

"Anticoagulants" include hirudins, heparins, coumarins, low-molecular weight heparin, thrombin inhibitors, platelet inhibitors, platelet aggregation inhibitors, coagulation factor inhibitors, anti-fibrin antibodies and factor VIII-inhibitors (such as those described in WO 01/04269 and WO 2005/016455).

"Thrombolytic agents" include wild-type plasmin, wild-type plasminogen, urokinase, streptokinase, tissue-type plasminogen activator (tPA or alteplase), urokinase-type plasminogen activator (uPA) and staphylokinase or any variant or derivative of any thereof such as APSAC (anisoylated plasminogen streptokinase activator complex), reteplase, tenecteplase, scuPA (single chain uPA), or a combination of any thereof.

"Anti-inflammatory agents" include steroids (e.g. prednisolone, methylprednisolone, cortisone, hydrocortisone, prednisone, triamcinolone, dexamethasone) and non-steroidal anti-inflammatory agents (NSAIDs; e.g. acetaminophren, ibuprofen, aspirin).

"Antiviral agents" include trifluridine, vidarabine, acyclovir, valacyclovir, famciclovir, and doxuridine.

"Antibacterial agents" or antibiotics include ampicillin, penicillin, tetracycline, oxytetracycline, framycetin, gatifloxacin, gentamicin, tobramycin, bacitracin, neomycin and polymyxin.

"Anti-mycotic/fungistatic/antifungal agents" include fluconazole, amphotericin, clotrimazole, econazole, itraconazole, miconazole, 5-fluorocytosine, ketoconazole and natamycin.

"Anti-angiogenic agents" include antibodies (or fragments thereof) such as anti-VEGF (vascular endothelial growth factor) or anti-P1GF (placental growth factor) antibodies and agents such as macugen (pegaptanib sodium), trypthophanyl-tRNA synthetase (TrpRS), anecortave acetate, combrestatin A4 prodrug, AdPEDF (adenovector capable of expressing pigment epithelium-derived factor), VEGF-trap, inhibitor of VEGF receptor-2, inhibitors of VEGF, P1GF or TGF-β, Sirolimus (rapamycin) and endostatin.

"Anti-mitotic agents" include mitomycin C and 5-fluorouracyl.

"Antihistamine" includes ketitofen fumarate and pheniramine maleate.

"Anesthetics" include benzocaine, butamben, dibucaine, lidocaine, oxybuprocaine, pramoxine, proparacaine, proxymetacaine, tetracaine and amethocaine.

"Contacting", when used herein, means any mode of administration that results in interaction between a composition such as a medicament and the tissue, body fluid, organ, organism, etc. with which said composition is contacted. The interaction between the composition and the tissue, body fluid, organ, organism, etc can occur starting immediately or nearly immediately with the administration of the composition, can occur over an extended time period (starting immediately or nearly immediately with the administration of the composition), or can be delayed relative to the time of administration of the composition.

Any method of contacting a pathological fibrin deposit that provides (either immediately, delayed or over an extended time period) an effective amount of a plasmin (or any variant or derivative thereof or alternative therefore) to such fibrin deposit can be utilized. If such fibrin deposit is associated with a blood clot, the plasmin (or any variant or derivative thereof or alternative therefore) can be delivered intra-arterially, intravenously, or locally (within short distance of the clot or even in the clot) by means of injection and/or infusion and/or a catheter.

When using plasmin (or any variant or derivative thereof or alternative therefore) in enzymatic debridement, it may be included in a gel-like composition capable of being applied topically, or may be applied in liquid form.

Any method of contacting the eye vitreous and/or aqueous humor that provides (either immediately, delayed or over an extended time period) an effective amount of a plasmin (or any variant or derivative thereof or alternative therefore) to the vitreous and/or aqueous humor can be utilized. One method of contacting the vitreous and/or aqueous humor is by one or more intraocular injections directly into the vitreous and/or aqueous humor. Alternatively, said contacting may involve subconjunctival, intramuscular or intravenous injections. A further alternative contacting method involves placing an intra-vitreal implantable device such as OCUSERT® (Alza Corp., Palo Alto, Calif.) or VITRASERT® (Bausch & Lomb Inc., Rochester, N.Y.). Contacting the vitreous and/or aqueous humor with an effective amount of a plasmin (or any variant or derivative thereof or alternative therefore) may be in a continuous fashion using a depot, sustained release formulation or any implantable device suitable thereto.

The term "effective amount" refers to the dosing regimen of the medicament according to the invention, in particular of the active ingredient of the medicament according to the invention, i.e., plasmin or an active truncated variant thereof (or any alternative therefore as described above). The effective amount will generally depend on and will need adjustment to the mode of contacting or administration and the condition to be treated. The effective amount of the medicament, more particular its active ingredient, is the amount required to obtain the desired clinical outcome or therapeutic or prophylactic effect without causing significant or unnecessary toxic effects. To obtain or maintain the effective amount, the medicament may be administered as a single dose or in multiple doses. The effective amount may further vary depending on the severity of the condition that needs to be treated or the expected severity of the condition that needs to be prevented; this may depend on the overall health and physical condition of the patient and usually the treating doctor's or physician's assessment will be required to establish what is the effective amount. The effective amount may further be obtained by a combination of different types of administration. The medicament may be administered as a solution (liquid or semi-liquid, e.g., gel-like or in dispersion or suspension, colloidal, in emulsion, nanoparticle suspension) or as a solid (e.g. tablet, minitablet, hard- or soft-shelled capsules).

For purposes of thrombolysis, plasmin dosage and duration of plasmin therapy will typically depend on the size and location of the blood clot as well as on the size, weight and age of the patient. If a clot is venous, treatment with plasmin may continue for days whereas only hours of plasmin therapy may be required if the clot is arterial. A myocardial infarction may be treated with a short single dose treatment whereas conditions such as thrombophlebitis and pulmonary embolism may require longer multiple dose treatment. Prolonged continuous and/or intermittent thrombolytic plasmin therapy may be applied to treat a coronary occlusion or in case of prophylactic therapy in order to reduce the risk of clot formation in subjects known to have an increased risk to develop clot formation. A further factor influencing plasmin dosage includes the circulating levels plasmin inhibitors such as α2-antiplasmin and/or α2-macroglobulin, the initial level of which being patient-dependent. It may be advisable to adjust the plasmin dosage such that no more than 15% of the total circulating α2-antiplasmin is remaining in order to achieve efficient thrombolytic therapy. For the purpose of inducing thrombolysis, a contacting method delivering a plasmin or any variant or derivative thereof or alternative therefore at a short distance proximal to a thrombus may be advantageous as the exposure to serum inhibitors is reduced. Such contacting method typically involves delivery via a catheter device. For use in thrombolysis, typical plasmin dosages range from 500 microgram/body weight to 10 milligram/kg body weight given as a single bolus or divided over 1 initial bolus injection followed by 1 or more repeat bolus injections. Plasmin may alternatively be administered over an extended time period, e.g. by infusion or by drug delivery micropump. Plasmin dosages for continued administration may range from 1 to 10 mg/kg/hour.

A typical plasmin dosage for inducing posterior vitreous detachment, vitreous liquefaction, clearance of vitreal blood or hemorrhages, or clearance of toxic materials or foreign substances from the vitreous cavity may be in the range of about 0.1 microgram to about 250 microgram per eye per dose, which can be delivered in a diluent or carrier volume of about 50 microliter to about 300 microliter per eye per dose. The diluent or carrier may e.g. be a sterile Balanced Salt Solution (BSS or BSS Plus), a physiologic saline solution or a solution containing 1-10 mM of an acid such as citric acid. In one embodiment plasmin is delivered to the eye in a dose of 125 microgram contained in 0.1 mL diluent or carrier. In the case of planned surgical vitrectomy, said plasmin may be delivered to the eye 15 to 300 minutes, or 15 to 120 minutes prior to the vitrectomy. Alternatively, the purpose of administering plasmin in the eye is to avoid surgical vitrectomy, or to facilitate subsequent surgical vitrectomy in case plasmin treatment itself would not be able to achieve full posterior vitreous detachment. When using plasminogen as an alternative source for plasmin (see "plasmin" definition), up to 250 microgram of plasminogen can be introduced per eye and said plasminogen may be accompanied by up to 2000 IU of urokinase or streptokinase as plasminogen activator or by up to 25 microgram of tPA. When used in the eye, plasmin or plasminogen administration may further be accompanied by administration of a gaseous adjuvant such as air, an expanding gas or liquefiable gas, or mixtures thereof, as long as it is non-toxic to the eye. Other suitable gaseous materials include SF6 (sulfur hexafluoride) and perfluorocarbons, such as C2F6 (hexafluoroethane), C3F8 (octafluoropropane), C4F8 (octafluorocyclobutane), oxygen, nitrogen, carbon dioxide, argon, and other inert gases. The volume of the gaseous material that is introduced into the eye can vary depending on the gaseous material, the patient, and the desired result. For example, the volume of air that is injected into the posterior chamber can range from about 0.5 mL to about 0.9 mL.

Other gaseous materials, such as SF6 and perfluorocarbon gases can range from about 0.3 mL to 0.5 mL. Preferably, the gaseous material is introduced into the posterior chamber of the eye in an amount sufficient to compress the vitreous against the posterior hyaloid and form a cavity in the vitreous without damaging the eye. In preferred embodiments, the gaseous adjuvant is introduced into the vitreous to form a cavity that fills about 40% to about 60% of the internal volume of the intraocular cavity.

The above recited dosages are indicative values not meant to be limiting in any way. Said dosages furthermore refer to wild-type plasmin or plasminogen or any active or activatable truncated variant thereof. When using a plasmin with increased stability according to the invention (or any variant or derivative thereof or alternative therefore), and depending on the ultimate stability and residual activity of a plasmin according to the invention, dosages may be similar, higher or lower to obtain the same or better overall clinical effect as obtained with wild-type plasmin. Dosage of a plasmin according to the invention may also depend on the rate of inhibition by endogenous inhibitors such as α2-antiplasmin.

In line with the work herein disclosed, the invention further relates to methods for screening for autoproteolytically stable plasmin variants, said methods comprising the steps of:
(i) mutating an amino acid at a position [P+/−n] into an amino acid different from the natural amino acid at position [P+/−n], wherein the amino acid at position P is an arginine or lysine, and wherein n is 1, 2, 3, 4 or 5;
(ii) determining the autoproteolytic stability of the mutant obtained from (i), such as determined as described above, e.g. by means of a chromogenic or biological substrate activity assay;
(iii) comparing the autoproteolytic stability of the mutant determined in (ii) with the autoproteolytic stability of wild-type plasmin; and
(iv) selecting from (iii) a mutant that is autoproteolytically more stable than wild-type plasmin as the autoproteolytically stable variant;
wherein said human plasmin catalytic domain is starting with the amino acid valine at position 1 which is the same valine amino acid occurring at position 562 of human Glu-plasminogen. In the above method, the amino acid at position [P+/−n] preferably is not a lysine and not an arginine.

The invention likewise relates to methods for screening for an autoproteolytically stable plasmin variant, said methods comprising:
(i) mutating the glutamate amino acids at positions 138 of the human plasmin catalytic domain, or of the corresponding glutamate of a non-human plasmin, into an amino acid different from the natural amino acid at said position 138;
(ii) determining the autoproteolytic stability of the mutant obtained from (i), such as determined or analyzed as described above, e.g. by means of a chromogenic or biological substrate activity assay; and
(iii) selecting from (ii) a mutant that is autoproteolytically stable as the autoproteolytically stable plasmin variant;
wherein said human plasmin catalytic domain is starting with the amino acid valine at position 1 which is the same valine amino acid occurring at position 562 of human Glu-plasminogen.

In any of the above screening methods, the said catalytic domain may further comprise a mutation of a wild-type lysine or arginine at one or more of the positions P, P', P", etc., into a non-lysine, nor-arginine amino acid.

The above screening methods may further comprise a step wherein the proteolytic activity of the autoproteolytically stable plasmin variant is determined.

Many products including medicines (here to be understood specifically as user-ready active ingredient, i.e. in the final formulation for administration to a patient) and bulk-stored active ingredients of medicines are usually stored for a considerable amount of time prior to use. It is of interest to extend the shelf-life of products as long as possible. With the shelf-life is meant the time during which the product can be used safely and during which the product retains it potent utility, i.e. its activity in the case of a medicine and/or its active ingredient. Typically, the shelf-life is indicated on a product or its package. Once the shelf-life has expired, the safe and potent utility of a product is no longer guaranteed. A further important aspect in storing products is the storage temperature at which the desired shelf-life can be achieved. For example, the shelf-life of a product stored at +4° C. or average refrigerator temperature may amount to 12 months whereas the shelf-life of the same product stored at −20° C. or average freezer temperature may amount to 36 months. Logistically, however, maintaining a cold chain at freezing temperatures, e.g. −20° C., is much more complex, difficult and expensive than maintaining a cold chain at +4° C. Thus, it may still be attractive to have a shorter, but sufficiently long shelf-life combined with the possibility to store a product at +4° C. The present invention offers a solution for extending, enhancing or increasing the shelf-life or long-term storage stability of plasmin or any active fragment or derivative thereof or of a composition comprising plasmin or any active derivative thereof. The solution resides in making available plasmin variants as herein described, said variants having an enhanced stability, which, intrinsically, increases, enhances or extends their shelf-life.

The invention likewise relates to methods for enhancing long-term storage stability of a plasmin-comprising composition, said methods comprising the step of identifying an autoproteolytically stable plasmin variant capable of being stored over a long time without significant loss of proteolytic activity. For determining long-term stability, a plasmin preparation according to the invention is aliquoted and activity measurements are performed repeatedly during the envisaged storage term. If the envisaged storage term is, e.g., 24 months, activity measurements can be performed, e.g. every month. The allowable loss of proteolytic activity at the end of the envisaged storage term will largely depend on the envisaged clinical application but typically may be no more than e.g. 10% to 15%.

The invention furthermore relates to methods for producing a plasminogen variant according to the invention, i.e. for producing a plasminogen comprising in its catalytic domain the mutation of at least one internal amino acid at position [P+/−n] (wherein is an integer selected from the group consisting of 1, 2, 3, 4 and 5) of which the peptide bond with internal amino acid at position P is prone to autoproteolysis into an amino acid of which the peptide bond with internal amino acid at position P is less or not prone to autoproteolysis. Such methods include the steps of:
(i) introducing in a suitable host cell a nucleic acid encoding a plasminogen variant according to the invention in a suitable host cell capable of expressing said plasminogen;
(ii) growing the host cell obtained in (i) under conditions and during a time sufficient for expression of said plasminogen in said host cell; and
(iii) harvesting the plasminogen expressed in (ii).

Eventually a step (iv) can be added to such methods which includes the purification of the plasminogen harvested in (iii).

Suitable host cells and methods for expression and production are disclosed in e.g. WO 90/13640 (insect cells), WO 2002/050290 and WO 03/066842 (yeast cells), WO 2008/054592 (bacterial cells/refolding process) and WO 2005/078109 (duckweed transgenic plants or transgenic plant cells).

The invention further encompasses methods for producing a plasmin variant according to the invention, i.e. for producing a plasmin comprising in its catalytic domain the mutation of at least one internal amino acid at position [P+/−n] (wherein is an integer selected from the group consisting of 1, 2, 3, 4 and 5) of which the peptide bond with internal amino acid at position P is prone to autoproteolysis into an amino acid of which the peptide bond with internal amino acid at position P is less or not prone to autoproteolysis. Such methods generally include the steps of producing a plasminogen according to the invention as described above and further comprise a step of activating the plasminogen according to the invention to a plasmin according to the invention using a suitable plasminogen activator (such as tPA, uPA, urokinase, streptokinase, staphylokinase or any variant thereof). Eventually one or more steps can be added wherein the plasminogen is purified prior to activation, activated plasmin is purified and/or active plasmin is derivatized as described above and/or reversibly inactivated and/or, optionally, brought to suitable storage conditions (such as stabilizing solution, lyophilized and/or low temperature).

In any of the above production methods, the said catalytic domain may further comprise a mutation of a wild-type lysine or arginine at one or more of the positions P, P', P", etc., into a non-lysine, nor-arginine amino acid.

Any of the plasminogen variants, plasmin variants, or plasmin derivatives as describe above are preferentially obtained in free, or soluble, form, e.g. not attached or bound to the surface of the expressing host (such as is the case in phage display).

The invention also relates to (an) isolated nucleic acid sequence(s) encoding a plasminogen variant or plasmin variant according to the invention. The invention also relates to (a) recombinant vector(s) comprising such nucleic acid. The invention also relates to (a) host cell(s) transformed with such nucleic acid or with such recombinant vector.

EXAMPLES

Example 1

Construction, Expression and Purification of Plasminogen Variants and Activation to Plasmin Expression Vector The pPICZαA secretion vector purchased from Invitrogen Corporation (Carlsbad, Calif.) was used to direct expression and secretion of recombinant human microplasminogen in *Pichia pastoris*.

This vector contains the secretion signal of the *Saccharomyces cerevisiae* α-factor prepropeptide. A XhoI recognition sequence is present at the COOH-terminus of the α-factor secretion signal, immediately upstream of the Lys-Arg site that is cleaved by Kex2 to remove the secretion signal from the mature protein. This XhoI restriction site may be used to clone the gene of interest flush with the Kex2 cleavage site by synthesizing the gene with the XhoI and Kex2 recognition sites at its 5' end. The recombinant gene of interest will then be expressed with the native $NH_2$-terminus. Engineered immediately downstream from the α-factor secretion signal in the pPICZαA vector is a multiple cloning site with recognition sites for the restriction enzymes EcoRI, SfiI, KpnI, SacII and XbaI to facilitate the cloning of heterologous genes.

Gene Synthesis

To improve expression of human microplasminogen in *Pichia pastoris*, genes encoding the human microplasminogen and variants thereof were synthesized de novo taking into account the preferred codon usage by *Pichia pastoris*.

To design the codon-optimized gene sequence, the human microplasminogen amino acid sequence (SEQ ID NO:19) was imported in the program Gene Designer which is developed by DNA2.0 (Menlo Park, Calif.) and is freely available on the internet. This sequence was backtranslated into DNA sequence using the *Pichia pastoris* codon usage table provided with the program. The nucleotide sequence was then checked manually and adjusted to better fit *Escherichia coli* codon usage. In addition, 6-base pair palindromic sequences and nucleotide repetitions were removed when possible. At the 5' end, a XhoI restriction site and the Kex2 cleavage site were added and at the 3' end, a XbaI restriction site was added. The resulting sequence is disclosed in International Patent Application No. PCT/EP2010/059902.

In order to change amino acid residues, mutations were introduced by site-directed mutagenesis using the QuikChange II Site Directed Mutagenesis Kit from Agilent (La Jolla, Calif.) in the wild-type microplasminogen sequence or in variant microplasminogen sequences in which specific autocatalytic cleavage sites were already changed (see International Patent Application No. PCT/EP2010/059902). The *E. coli* strain TOP10 (Invitrogen) was transformed with the site-directed mutagenesis mixture and ampicillin resistant clones were selected. Sequence determination of the resulting plasmid clones confirmed the precise mutagenesis of the targeted microplasminogen coding region, as well as the absence of unwanted mutations in the coding region.

The following primers were used for site-directed mutagenesis:

```
Glu138Gln mutation
                              (sense; SEQ ID NO: 20)
GTTCGGTGCTGGTCTGTTGAAACAGGCACAATTACCTGTGATTG
and
                           (antisense; SEQ ID NO: 21)
CAATCACAGGTAATTGTGCCTGTTTCAACAGACCAGCACCGAAC)
```

In a first variant, the glutamate at position 138 is substituted by a glutamine. Glu138 is encoded by the codon GAA at positions 481-483. The nucleotides GAA (positions 481-483) were changed into CAG, changing Glu138 into Gln in the microplasminogen protein (nucleotide sequence is in SEQ ID NO:22 and the deduced amino acid sequence in SEQ ID NO:23).

In the second variant, the glutamate at position 138 is substituted by a glutamine as above in a variant microplasminogen in which the lysine at position 147 had already been substituted by glutamate (nucleotide sequence is in SEQ ID NO:24 and the deduced amino acid sequence in SEQ ID NO:25).

In the third variant, the glutamate at position 138 is substituted by a glutamine as above in a variant microplasminogen in which the lysine at position 147 had already been substituted by histidine and the arginine at position 158 had already been substituted by histidine (nucleotide sequence is in SEQ ID NO:26 and the deduced amino acid sequence in SEQ ID NO:27).

Expression of Microplasminogen Variants and Activation to Plasmin

Prior to activation, the microplasminogen mutants were purified by immuno-affinity directly from the *Pichia pastoris* supernatants. A murine anti-human microplasmin antibody (raised in Balb/c mice using microplasmin as antigen; produced by hybridoma cell line 5D10A4, available at ThromboGenics N.V.) was coupled on sepharose beads according to the protocol n° 71500015AD from GE Healthcare. Following this protocol, 7.5 mL of immuno-affinity resin were prepared from 45 mg of antibody and packed in a XK 16/20 column. Crude supernatant 200-400 mL (0.2µ, filtered from *Pichia* culture/pH 6.0) was directly loaded on the 5D 10A4 affinity column. After a wash step (100 mM KH2PO4, 0.5 M NaCl, pH 6.2, 10 column volumes), the microplasminogen variant was eluted with a 0.2 M Glycine-HCl, pH 3.0 buffer and the eluate was neutralized and dialyzed against 25 mM Sodium Phosphate buffer, pH 7.2).

The microplasmin variants were activated essentially following the procedure as outlined in Example 2 of WO 02/50290.

By way of example, the above-described mutant microplasminogen E138Q and the corresponding activated microplasmin are shown in FIG. 3.

Amino acid sequences and nucleotide sequences of the above described wild-type and variant microplasminogen species are listed hereafter.

```
SEQ ID NO: 19 - Wild-type Human microplasminogen amino acid sequence
APSFDCGKPQVEPKKCPGRVVGGCVAHPHSWPWQVSLRTRFGMHFCGGTLISPEWVLT

AAHCLEKSPRPSSYKVILGAHQEVNLEPHVQEIEVSRLFLEPTRKDIALLKLSSPAVITDK

VIPACLPSPNYVVADRTECFITGWGETQGTFGAGLLKEAQLPVIENKVCNRYEFLNGRV

QSTELCAGHLAGGTDSCQGDSGGPLVCFEKDKYILQGVTSWGLGCARPNKPGVYVRVS

RFVTWIEGVMRNN

SEQ ID NO: 22 - Microplasminogen variant with the Glu138Gln substitution (mutated
codon in bold italics underlined, XhoI and XbaI underlined)
CTCGAGAAAAGAGCACCTTCATTCGACTGTGGTAAGCCTCAGGTCGAACCTAAGAA

GTGTCCAGGTCGTGTTGTCGGTGGCTGTGTGGCTCATCCTCATTCTTGGCCTTGGCAA

GTGTCTCTTAGAACTAGATTTGGTATGCACTTCTGTGGTGGCACCTTGATCTCACCTG

AATGGGTCTTAACCGCAGCTCATTGTCTGGAGAAGTCACCACGTCCATCTTCATACA

AGGTCATCCTTGGCGCACATCAGGAAGTCAATCTTGAGCCTCATGTTCAGGAGATCG

AAGTCTCTCGTTTGTTCTTGGAACCAACTCGTAAAGACATTGCTCTTCTGAAGCTGTC

ATCTCCTGCCGTGATTACCGACAAGGTAATTCCTGCCTGCTTGCCTAGTCCTAATTAC

GTCGTTGCCGACCGTACCGAATGCTTCATTACTGGTTGGGGTGAGACTCAAGGTACG

TTCGGTGCTGGTCTGTTGAAACAGGCACAATTACCTGTGATTGAGAACAAGGTTTGT

AACAGATACGAGTTCCTGAATGGTCGTGTTCAGTCCACTGAGTTGTGTGCAGGTCAC

CTTGCAGGTGGTACTGATAGTTGTCAAGGTGATTCTGGTGGACCACTGGTGTGCTTC

GAGAAGGATAAGTACATCTTACAAGGTGTTACGTCTTGGGGTCTTGGATGTGCTCGT
```

-continued

CCTAACAAGCCAGGTGTCTACGTCAGAGTCTCCAGATTCGTAACTTGGATCGAAGGT

GTCATGCGTAACAACTAA<u>TCTAGA</u>

SEQ ID NO: 23 - Deduced amino acid sequence of SEQ ID NO: 22 (the underlined N-
terminal amino acids "LEKR" are encoded by the introduced XhoI + Kex2 cleavage sites;
the introduced amino acid mutation is indicated in bold/italic and is underlined)
<u>LEKR</u>APSFDCGKPQVEPKKCPGRVVGGCVAHPHSWPWQVSLRTRFGMHFCGGTLISPE

WVLTAAHCLEKSPRPSSYKVILGAHQEVNLEPHVQEIEVSRLFLEPTRKDIALLKLSSPA

VITDKVIPACLPSPNYVVADRTECFITGWGETQGTFGAGLLK*Q*AQLPVIENKVCNRYEFL

NGRVQSTELCAGHLAGGTDSCQGDSGGPLVCFEKDKYILQGVTSWGLGCARPNKPGVY

VRVSRFVTWIEGVMRNN

SEQ ID NO: 24 - Microplasminogen variant with the Glu138Gln and Lys147Glu
substitutions (mutated codons in bold italics underlined, XhoI and XbaI underlined)
<u>CTCGAG</u>AAAAGAGCACCTTCATTCGACTGTGGTAAGCCTCAGGTCGAACCTAAGAA

GTGTCCAGGTCGTGTTGTCGGTGGCTGTGTGGCTCATCCTCATTCTTGGCCTTGGCAA

GTGTCTCTTAGAACTAGATTTGGTATGCACTTCTGTGGTGGCACCTTGATCTCACCTG

AATGGGTCTTAACCGCAGCTCATTGTCTGGAGAAGTCACCACGTCCATCTTCATACA

AGGTCATCCTTGGCGCACATCAGGAAGTCAATCTTGAGCCTCATGTTCAGGAGATCG

AAGTCTCTCGTTTGTTCTTGGAACCAACTCGTAAAGACATTGCTCTTCTGAAGCTGTC

ATCTCCTGCCGTGATTACCGACAAGGTAATTCCTGCCTGCTTGCCTAGTCCTAATTAC

GTCGTTGCCGACCGTACCGAATGCTTCATTACTGGTTGGGGTGAGACTCAAGGTACG

TTCGGTGCTGGTCTGTTAAA*<u>CAG</u>*GCACAATTACCTGTGATTGAGAAC*<u>GAA</u>*GTGTGT

AACAGATACGAGTTCCTGAATGGTCGTGTTCAGTCCACTGAGTTGTGTGCAGGTCAC

CTTGCAGGTGGTACTGATAGTTGTCAAGGTGATTCTGGTGGACCACTGGTGTGCTTC

GAGAAGGATAAGTACATCTTACAAGGTGTTACGTCTTGGGGTCTTGGATGTGCTCGT

CCTAACAAGCCAGGTGTCTACGTCAGAGTCTCCAGATTCGTAACTTGGATCGAAGGT

GTCATGCGTAACAACTAA<u>TCTAGA</u>

SEQ ID NO: 25 - Deduced amino acid sequence of SEQ ID NO: 24 (the underlined N-
terminal amino acids "LEKR" are encoded by the introduced XhoI + Kex2 cleavage sites;
the introduced amino acid mutations are indicated in bold italics underlined)
<u>LEKR</u>APSFDCGKPQVEPKKCPGRVVGGCVAHPHSWPWQVSLRTRFGMHFCGGTLISPE

WVLTAAHCLEKSPRPSSYKVILGAHQEVNLEPHVQEIEVSRLFLEPTRKDIALLKLSSPA

VITDKVIPACLPSPNYVVADRTECFITGWGETQGTFGAGLLK*<u>Q</u>*AQLPVIEN*<u>E</u>*VCNRYEFL

NGRVQSTELCAGHLAGGTDSCQGDSGGPLVCFEKDKYILQGVTSWGLGCARPNKPGVY

VRVSRFVTWIEGVMRNN

SEQ ID NO: 26 - Microplasminogen variant with the Glu138Gln, Lys147His and
Arg158His substitutions (mutated codons in bold italics underlined, XhoI and XbaI
underlined)
<u>CTC -continued
```
GTCGTTGCCGACCGTACCGAATGCTTCATTACTGGTTGGGGTGAGACTCAAGGTACG

TTCGGTGCTGGTCTGTTGAAACAGGCACAATTACCTGTGATTGAGAACCACGTGTGT

AACAGATACGAGTTCCTGAATGGACACGTGCAGTCCACTGAGTTGTGTGCAGGTCAC

CTTGCAGGTGGTACTGATAGTTGTCAAGGTGATTCTGGTGGACCACTGGTGTGCTTC

GAGAAGGATAAGTACATCTTACAAGGTGTTACGTCTTGGGGTCTTGGATGTGCTCGT

CCTAACAAGCCAGGTGTCTACGTCAGAGTCTCCAGATTCGTAACTTGGATCGAAGGT

GTCATGCGTAACAACTAATCTAGA
```

SEQ ID NO: 27 - Deduced amino acid sequence of SEQ ID NO: 26 (the underlined N-
terminal amino acids "LEKR" are encoded by the introduced XhoI + Kex2 cleavage sites;
the introduced amino acid mutations are indicated in bold italics underlined)

LEKRAPSFDCGKPQVEPKKCPGRVVGGCVAHPHSWPWQVSLRTRFGMHFCGGTLISPE

WVLTAAHCLEKSPRPSSYKVILGAHQEVNLEPHVQEIEVSRLFLEPTRKDIALLKLSSPA

VITDKVIPACLPSPNYVVADRTECFITGWGETQGTFGAGLLK*Q*AQLPVIEN*H*VCNRYEFL

NG*H*VQSTELCAGHLAGGTDSCQGDSGGPLVCFEKDKYILQGVTSWGLGCARPNKPGV

YVRVSRFVTWIEGVMRNN

Autolysis Rate Constants and Kinetic Parameters of Microplasmin Variants

The $k_{cat}$/Km and autolysis rate constant values obtained for various microplasmin mutants are listed in Table 2 hereunder. These values were obtained essentially following the methods described in Examples 3 and 4 of International Patent Application No. PCT/EP2010/059902.

TABLE 2

| Microplasmin Variant | Kinetic parameters $K_{cat}$/Km ($M^{-1}s^{-1}$) | Autolysis rate constant k ($M^{-1}s^{-1}$) |
|---|---|---|
| Wild-type | 6.9 × 10⁵ | 123 |
| K147E | 8.5 × 10⁵ | 24 |
| E138Q | 9.5 × 10⁵ | 4 |
| E138Q K147E | 10.9 × 10⁵ | 2 |
| E138Q K147H R158H | 5.5 × 10⁵ | 6 |

Example 2

Therapeutic Efficacy of Plasmin Variants in In Vitro or In Vivo Models 2.1 Effect of Plasmin Variants on Cerebral Infarct Size.

The efficacy of the plasmin variants of the invention in reducing cerebral infarct size can be performed in a murine cerebral infarct model such as described in Example 2 of WO 00/18436, or according to Welsh et al. (1987, J Neurochem 49, 846-851). The beneficial effect of wild-type plasmin on cerebral infarct size was demonstrated in Example 5 of WO 00/18436. A similar experiment is performed with any of the plasmin variants of the invention and the beneficial effect of these plasmin variants is measured and compared to the beneficial effect of wild-type plasmin.

2.2 In Vivo Thrombolytic Activity of Plasmin Variants

The rabbit extracorporeal loop thrombolysis model (Example 6 of WO 02/50290; Hotchkiss et al., 1987, Thromb Haemost 58, 107 —Abstract 377), the dog circumflex coronary artery copper coil-induced thrombosis model (Example 8 of WO 02/50290; Bergmann et al., 1983, Science 220, 1181-1183) or the rabbit jugular vein thrombosis model (Collen et al., 1983, J Clin Invest 71, 368-376) can be used to demonstrate in vivo thrombolytic activity of the plasmin variants of the invention. The beneficial effect of wild-type plasmin on thrombolysis was demonstrated with these models as described in Examples 7 and 9 of WO 00/18436 and by Collen et al. (1983). Similar experiments are performed with any of the plasmin variants of the invention and the beneficial effect of these plasmin variants is measured and compared to the beneficial effect of wild-type plasmin.

2.3 In Vitro Thrombolytic Activity of Plasmin Variants

An in vitro model of peripheral arterial occlusion (PAO) is described in Example 6 of WO 01/36609 and the thrombolytic efficacy of wild-type plasmin was demonstrated in this model. A similar experiment is performed with any of the plasmin variants of the invention and the beneficial effect of these plasmin variants on thrombolysis of peripheral arterial occlusions is measured and compared to the beneficial effect of wild-type plasmin.

2.4 Liquefaction of Eye Vitreous and Posterior Vitreous Detachment Induced by Plasmin Variants Example 5 of WO 2004/052228 discloses an assay for determining the efficacy, as well as the efficacy of microplasmin in liquefying the vitreous in post-mortem pig eyes. Example 6 of WO 2004/052228 discloses an assay for determining the efficacy, as well as the efficacy of microplasmin in inducing posterior vitreous detachment (PVD) in human post-mortem eyes. Induction of vitreous liquefaction and PVD by the plasmin variants of the invention is demonstrated in similar post-mortem models.

2.5 In Vivo PVD Induced by Plasmin Variants

Example 7 of WO 2004/052228 discloses an assay for determining the efficacy, as well as the efficacy of microplasmin in inducing PVD in an in vivo feline model. Induction of PVD by the plasmin variants of the invention is demonstrated in a similar in vivo model.

The invention claimed is:

1. A plasminogen variant, or a plasmin variant, or a proteolytically active or reversibly inactive derivative of a plasmin wherein:

the plasminogen variant, the plasmin variant, or the proteolytically active or reversibly inactive derivative of the plasmin comprises the catalytic domain of a human or a non-human plasmin, wherein if the catalytic domain is that of human plasmin, the catalytic domain comprises a substitution of the amino acid glutamate at position 138 of the human plasmin catalytic domain with a different amino acid, and wherein if the catalytic domain is that of a non-human plasmin, the catalytic domain comprises a substitution of the amino acid residue corresponding to position 138 of the human plasmin catalytic domain in the non-human plasmin catalytic domain with a different amino acid.

2. A plasminogen variant, or a plasmin variant, or a proteolytically active or reversibly inactive derivative of plasmin comprising the catalytic domain of a human or a non-human plasmin, wherein the catalytic domain comprises a lysine or arginine at an internal position P and a substitution of at least two internal amino acids:

at positions [P+/−n] and [P+/−n']; wherein n and n' are 1, 2, 3, 4 or 5; wherein the amino acids at positions [P+/−n] and [P+/−n'] are not lysine and not arginine; and wherein n and n' are different from each other if both are either added to or subtracted from P; or at positions [P+/−n] and [P'+/−n]; wherein P' is the greater value of P and P'; wherein the amino acid at position P' is a lysine or arginine; wherein n is 1, 2, 3, 4 or 5; wherein the amino acid at position [P'+/−n] is not a lysine and not an arginine; and wherein, if present, positions overlapping between [P+n] and [P'−n] are excluded.

3. The plasminogen variant, plasmin variant, or the proteolytically active or reversibly inactive derivative of the plasmin of claim 1 further comprising substitution of a lysine or arginine amino acid of the catalytic domain with an amino acid other than arginine or lysine.

4. The plasminogen variant, plasmin variant, or the proteolytically active or reversibly inactive derivative of the plasmin of claim 3, wherein the lysine or arginine is chosen from:
   (i) lysine at position 137 of the human plasmin catalytic domain, or the corresponding lysine or arginine of a non-human plasmin catalytic domain;
   (ii) lysine at position 147 of the human plasmin catalytic domain, or the corresponding lysine or arginine of a non-human plasmin catalytic domain; or
   (iii) arginine at position 158 of the human plasmin catalytic domain, or the corresponding arginine or lysine of a non-human plasmin catalytic domain.

5. The plasminogen variant, plasmin variant, or the proteolytically active or reversibly inactive derivative of the plasmin of claim 1, wherein the amino acid glutamate at position 138 of the human plasmin catalytic domain, or the corresponding amino acid residue of a non-human plasmin catalytic domain is substituted with an amino acid selected from the group consisting of glutamine, aspartate, and asparagine.

6. The plasmin variant, or the proteolytically active or reversibly inactive derivative of the plasmin of claim 1, wherein the autolysis constant of the plasmin variant or the proteolytically active or reversibly inactive derivative of the plasmin is at most 95% of the autolysis constant of wildtype plasmin.

7. The plasmin variant, or the proteolytically active or reversibly inactive derivative of the plasmin of claim 1, wherein the catalytic constant $k_{cat}$ of the plasmin variant or the proteolytically active or reversibly inactive derivative of the plasmin is in the range of 10% to 200% of the $k_{cat}$ of wildtype plasmin.

8. The plasmin variant, or the proteolytically active or reversibly inactive derivative of the plasmin of claim 1, wherein the autolysis constant of the plasmin variant or the proteolytically active or reversibly inactive derivative of the plasmin is at most 95% of the autolysis constant of wildtype plasmin and the catalytic constant $k_{cat}$ of the plasmin variant or the proteolytically active or reversibly inactive derivative of the plasmin is in the range of 10% to 200% of the $k_{cat}$ of wildtype plasmin.

9. The plasminogen variant, plasmin variant, or proteolytically active or reversibly inactive derivative of the plasmin of claim 1, wherein the plasminogen or plasmin is Glu-plasminogen or Glu-plasmin, Lys-plasminogen or Lys-plasmin, midiplasminogen or midiplasmin, miniplasminogen or miniplasmin, microplasminogen or microplasmin, deltaplasminogen or deltaplasmin.

10. A medicament comprising the plasminogen variant, plasmin variant, or proteolytically active or reversibly inactive derivative of the plasmin of claim 1, or any combination thereof.

11. A composition comprising the plasminogen variant, plasmin variant, or proteolytically active or reversibly inactive derivative of the plasmin of claim 1, or any combination thereof, and at least one of a pharmaceutically acceptable diluent, carrier, or adjuvant.

12. The composition of claim 11, further comprising at least one of an anticoagulant, a thrombolytic agent, an anti-inflammatory agent, an antiviral agent, an antibacterial agent, an antifungal agent, an anti-angiogenic agent, an anti-mitotic agent, an antihistamine, or an anesthetic.

13. A method for inducing or promoting lysis of a pathological fibrin deposit in a subject in need thereof; for inducing posterior vitreous detachment in the eye and/or for inducing liquefaction of the vitreous in the eye, or for facilitating surgical vitrectomy in the eye in a subject in need thereof; for enzymatic debridement of injured tissue of a subject in need thereof; for reducing circulating fibrinogen, or for reducing α2-antiplasmin levels in a subject in need thereof; for reducing the risk of pathological fibrin deposition in a subject in need thereof, for resolving vitreomacular adhesion in a subject in need thereof; for closing macular holes in a subject in need thereof; or in conjunction with trabeculectomy in a subject in need thereof, the method comprising administering to the subject the plasminogen variant, plasmin variant, or the proteolytically active or reversibly inactive derivative of the plasmin of claim 1.

14. A method for screening for an autoproteolytically stable plasmin variant, the method comprising:
   (i) providing a polypeptide comprising the catalytic domain of plasmin and preparing a mutant of the polypeptide comprising substituting an amino acid at a position [P+/−n] of the catalytic domain of plasmin, wherein the amino acid at position P is an arginine or lysine, and wherein n is 1, 2, 3, 4 or 5; (ii) determining the autoproteolytic stability of the mutant obtained from (i) with a chromogenic or biological substrate activity assay; (iii) comparing the autoproteolytic stability of the mutant determined in (ii) with the autoproteolytic stability of wild-type plasmin; and (iv) selecting from (iii) a mutant that is autoproteolytically more stable than wild-type plasmin as the autoproteolytically stable variant.

15. A method for screening for an autoproteolytically stable plasmin variant, the method comprising:
   (i) substituting the glutamate amino acid at position 138 of the human plasmin catalytic domain, or of the corresponding amino acid residue of a non-human plasmin catalytic domain, with an amino acid different from the amino acid occurring at position 138 in the wild type human plasmin catalytic domain or the wild type non-human plasmin catalytic domain,
   (ii) determining the autoproteolytic stability of the mutant obtained from (i), and
   (iii) selecting from (ii) a mutant that is autoproteolytically stable as the autoproteolytically stable plasmin variant;
   wherein the human plasmin catalytic domain refers to the polypeptide starting with the amino acid valine at position 1, which is the same valine amino acid occurring at position 562 of human Glu-plasminogen, and ending with the amino acid asparagine at position 230, which is the same asparagine amino acid occurring at position 791 of human Glu-plasminogen.

16. The method of claim 14 further comprising a step wherein the proteolytic activity of the autoproteolytically stable plasmin variant is determined.

17. A method for enhancing long-term storage stability of a plasmin-comprising composition, the method comprising the step of identifying an autoproteolytically stable plasmin variant of claim 1 that is capable of being stored over 24 months without significant loss of proteolytic activity.

18. A method for producing a plasminogen variant of claim 1, the method including the steps of:
   (i) introducing a nucleic acid encoding a plasminogen of claim 1 in a suitable host cell capable of expressing the plasminogen;

(ii) growing the host cell obtained in (i) under conditions and during a time sufficient for expression of the plasminogen in the host cell; and (iii) harvesting the plasminogen expressed in (ii).

19. The method of claim 18 further including a step (iv) wherein the plasminogen harvested in (iii) is purified.

20. A method for producing a plasmin variant of claim 1, the method including the steps of:
(i) introducing a nucleic acid encoding a plasminogen of claim 1 in a suitable host cell capable of expressing the plasminogen;
(ii) growing the host cell obtained in (i) under conditions and during a time sufficient for expression of the plasminogen in the host cell;
(iii) harvesting the plasminogen expressed in (ii);
(iv) activating the plasminogen of (iii) to plasmin.

21. The method of claim 20 wherein the plasminogen harvested in (iii) is purified prior to activation in (iv).

22. The method of claim 20 wherein the active plasmin obtained in (iv) is purified.

23. The method of claim 20 wherein the active plasmin is derivatized and/or reversibly inactivated.

24. The plasminogen variant, plasmin variant, or reversibly inactive derivative of the plasmin of claim 1, wherein the catalytic domain of plasmin comprising a substitution of the amino acid glutamate at position 138 of the human plasmin catalytic domain is the catalytic domain within the amino acid sequence set forth in SEQ ID NO:23.

25. The plasminogen variant, plasmin variant, or reversibly inactive derivative of the plasmin of claim 1, wherein the catalytic domain of plasmin comprising a substitution of the amino acid glutamate at position 138 of the human plasmin catalytic domain is the catalytic domain within the amino acid sequence set forth in SEQ ID NO:25.

26. The plasminogen variant, plasmin variant, or reversibly inactive derivative of the plasmin of claim 1, wherein the catalytic domain of plasmin comprising a substitution of the amino acid glutamate at position 138 of the human plasmin catalytic domain is the catalytic domain within the amino acid sequence set forth in SEQ ID NO:27.

27. A method for inducing or promoting lysis of a pathological fibrin deposit in a subject in need thereof; for inducing posterior vitreous detachment in the eye and/or for inducing liquefaction of the vitreous in the eye, or for facilitating surgical vitrectomy in the eye in a subject in need thereof; for enzymatic debridement of injured tissue of a subject in need thereof; for reducing circulating fibrinogen, or for reducing α2-antiplasmin levels in a subject in need thereof; for reducing the risk of pathological fibrin deposition in a subject in need thereof, for resolving vitreomacular adhesion in a subject in need thereof; for closing macular holes in a subject in need thereof; or in conjunction with trabeculectomy in a subject in need thereof, the method comprising administering to the subject the plasminogen variant, plasmin variant, or the proteolytically active or reversibly inactive derivative of the plasmin of claim 24.

28. A method for inducing or promoting lysis of a pathological fibrin deposit in a subject in need thereof; for inducing posterior vitreous detachment in the eye and/or for inducing liquefaction of the vitreous in the eye, or for facilitating surgical vitrectomy in the eye in a subject in need thereof; for enzymatic debridement of injured tissue of a subject in need thereof; for reducing circulating fibrinogen, or for reducing α2-antiplasmin levels in a subject in need thereof; for reducing the risk of pathological fibrin deposition in a subject in need thereof, for resolving vitreomacular adhesion in a subject in need thereof; for closing macular holes in a subject in need thereof; or in conjunction with trabeculectomy in a subject in need thereof, the method comprising administering to the subject the plasminogen variant, plasmin variant, or the proteolytically active or reversibly inactive derivative of the plasmin of claim 25.

29. A method for inducing or promoting lysis of a pathological fibrin deposit in a subject in need thereof; for inducing posterior vitreous detachment in the eye and/or for inducing liquefaction of the vitreous in the eye, or for facilitating surgical vitrectomy in the eye in a subject in need thereof; for enzymatic debridement of injured tissue of a subject in need thereof; for reducing circulating fibrinogen, or for reducing α2-antiplasmin levels in a subject in need thereof; for reducing the risk of pathological fibrin deposition in a subject in need thereof, for resolving vitreomacular adhesion in a subject in need thereof; for closing macular holes in a subject in need thereof; or in conjunction with trabeculectomy in a subject in need thereof, the method comprising administering to the subject the plasminogen variant, plasmin variant, or the proteolytically active or reversibly inactive derivative of the plasmin of claim 26.

30. A polypeptide comprising a catalytic domain of plasmin, wherein the catalytic domain of plasmin comprises:
(i) the catalytic domain of human plasmin with a substitution of the amino acid glutamate at position 138 of the human plasmin catalytic domain with a different amino acid, or
(ii) the catalytic domain of a non-human plasmin with a substitution of the amino acid residue of the non-human plasmin catalytic domain occurring at the position corresponding to position 138 of the human plasmin catalytic domain with a different amino acid.

31. The polypeptide of claim 30, wherein the catalytic domain of plasmin comprises the catalytic domain of human plasmin with a substitution of the amino acid glutamate at position 138 of the human plasmin catalytic domain.

32. The polypeptide of claim 31, further comprising a substitution of an amino acid occurring within one to five amino acids of lysine 147 of the human plasmin catalytic domain with a different amino acid.

33. The polypeptide of claim 31, further comprising a substitution of an amino acid occurring at position 146 or position 148 of the human plasmin catalytic domain with a different amino acid.

34. The polypeptide of claim 31, further comprising a substitution of an amino acid occurring within one to five amino acids of arginine 158 of the human plasmin catalytic domain with a different amino acid.

35. The polypeptide of claim 31, further comprising a substitution of an amino acid at position 157 or position 159 of the human plasmin catalytic domain with a different amino acid.

36. The polypeptide of claim 31, wherein the polypeptide can proteolyze a substrate selected from the group consisting of fibrin, fibrinogen, fibronectin, gelatin, laminin, and collagen.

37. The polypeptide of claim 31, wherein the polypeptide has an autolysis constant that is at most 95% of the autolysis constant of wild type plasmin.

38. The plasminogen variant, plasmin variant, or the proteolytically active or reversibly inactive derivative of the plasmin of claim 1, comprising the catalytic domain of human plasmin.

39. The plasminogen variant, plasmin variant, or the proteolytically active or reversibly inactive derivative of the plasmin of claim 2, wherein the presence of the substitution of the at least two internal amino acids reduces the extent of autoproteolytic degradation of the plasmin variant compared to the extent of autoproteolytic degradation of wild type plasmin, wherein the extent of autoproteolytic degradation is determined with a chromogenic or biological substrate activity assay.

40. The plasminogen variant, plasmin variant, or proteolytically active or reversibly inactive derivative of the plasmin of claim 2, wherein the plasminogen or plasmin is Glu-plasminogen or Glu-plasmin, Lys-plasminogen or Lys-plasmin, midiplasminogen or midiplasmin, miniplasminogen or miniplasmin, microplasminogen or microplasmin, deltaplasminogen or deltaplasmin.

41. A composition comprising the plasminogen variant, plasmin variant, or proteolytically active or reversibly inactive derivative of the plasmin of claim 2, or any combination thereof, and at least one of a pharmaceutically acceptable diluent, carrier, or adjuvant.

42. The plasminogen variant, plasmin variant, or the proteolytically active or reversibly inactive derivative of the plasmin of claim 2, comprising the catalytic domain of human plasmin.

43. A method for inducing or promoting lysis of a pathological fibrin deposit in a subject in need thereof; for inducing posterior vitreous detachment in the eye and/or for inducing liquefaction of the vitreous in the eye, or for facilitating surgical vitrectomy in the eye in a subject in need thereof; for enzymatic debridement of injured tissue of a subject in need thereof; for reducing circulating fibrinogen, or for reducing α2-antiplasmin levels in a subject in need thereof; for reducing the risk of pathological fibrin deposition in a subject in need thereof, for resolving vitreomacular adhesion in a subject in need thereof; for closing macular holes in a subject in need thereof; or in conjunction with trabeculectomy in a subject in need thereof, the method comprising administering to the subject the plasminogen variant, plasmin variant, or the proteolytically active or reversibly inactive derivative of the plasmin of claim 2.

44. The method of claim 13, wherein the subject is a human.

45. The method of claim 43, wherein the subject is a human.

* * * * *

UNITED STATES PATENT AND TRADEMARK OFFICE
CERTIFICATE OF CORRECTION

PATENT NO. : 9,121,014 B2  
APPLICATION NO. : 13/977836  
DATED : September 1, 2015  
INVENTOR(S) : Zwaal Page 1 of 1

It is certified that error appears in the above-identified patent and that said Letters Patent is hereby corrected as shown below:

On the title page item [57], Line 3: Delete "autocatylic" and insert -- autocatalytic --, therefor.

On the title page item [57], Line 4: After "activity" insert -- of --.

In the specification

Column 23, Line 29: In between the words "wherein" and "is" insert -- n --.

Column 23, Line 35: Delete "in a suitable host cell".

Column 23, Line 54: In between the words "wherein" and "is" insert -- n --.

Column 26, Line 19: Delete "0.2μ" and insert -- 0.2μm --, therefor.

Column 30, Line 52: Delete ", as well as the efficacy".

Signed and Sealed this  
Twenty-sixth Day of January, 2016

Michelle K. Lee  
*Director of the United States Patent and Trademark Office*

UNITED STATES PATENT AND TRADEMARK OFFICE
CERTIFICATE OF CORRECTION

PATENT NO.         : 9,121,014 B2                                    Page 1 of 1
APPLICATION NO.    : 13/977836
DATED              : September 1, 2015
INVENTOR(S)        : Zwaal It is certified that error appears in the above-identified patent and that said Letters Patent is hereby corrected as shown below:

In the claims

Column 111, In Claim 3, line 3, after "comprising" insert -- a --.

Signed and Sealed this
Twenty-fourth Day of May, 2016

Michelle K. Lee
*Director of the United States Patent and Trademark Office*